US006313375B1

(12) United States Patent
Jung et al.

(10) Patent No.: US 6,313,375 B1
(45) Date of Patent: Nov. 6, 2001

(54) MAIZE AQUAPORINS AND USES THEREOF

(75) Inventors: Rudolf Jung, Des Moines, IA (US); Francois Barrieu, Bordeaux (FR)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/372,422

(22) Filed: Aug. 11, 1999

Related U.S. Application Data

(60) Provisional application No. 60/098,692, filed on Aug. 13, 1998.

(51) Int. Cl.[7] ............................ C12N 5/04; C12N 15/09; C12N 15/29; C12N 15/82; A01H 5/10

(52) U.S. Cl. .......................... 800/278; 800/286; 800/295; 800/290; 800/298; 800/320; 800/320.1; 800/320.2; 800/320.3; 800/322; 800/306; 800/312; 800/314; 435/69.1; 435/468; 435/320.1; 435/419; 536/23.1; 536/23.6; 536/24.1; 536/24.5

(58) Field of Search .................................... 800/278, 286, 800/295, 290, 298, 320, 320.1, 320.2, 320.3, 322, 306, 314, 312; 435/69.1, 468, 320.1, 419; 536/23.1, 23.6, 24.1, 24.5

(56) References Cited

U.S. PATENT DOCUMENTS 5,850,020 * 12/1998 Bloksberg et al. .................. 800/205

OTHER PUBLICATIONS

Chevelier et al. Plant Mol. Biol. vol. 28, pp. 473–485, 1995.*

Zhu et al. Plant Physiolo. vol. 95, pp. 305–315, 1991.*

Kaldenhoff et al. The Plant J. vol. 7, No. 1, pp. 87–95, 1995.*

Liu et al. Plant Mol. Biol. vol.26, pp. 2003–2007, 1994.*

Hollenbach et al. Accession No. X76911, Deposited, Nov. 1995.*

Finkelstein et al. Accession No. X82633, Deposited, Aug. 1985.*

Brandazza et al. Accession No. Q04107, pp. 6–7, May 1992.*

Kuipers et al. Mol. Gen. Genet. vol. 246, pp. 745–755, 1995.*

Sandler et al. Plant Mol. Biol. vol. 11, pp. 301–310, 1988.*

Smith et al. Nature, vol. 334, pp. 724–726, Aug. 1988.*

Bird et al. Biotech and Genet. Eng. Rev., vol. 9, pp. 207–227, 1991.*

Agre, P., et al. (1998). The aquaporin, blueprints for cellular plumbing systems. *J. Biol. Chem.,* 273, 24, 14659–14662.

Barrieu, F., et al. (1998). High expression of the tonoplast aquaporin ZmTIP1 in epidermal and conducting tissues of maize. *Plant Physiol.* 117, 1153–1163.

Chaumont, F., et al. (1994) Truncated presequences of mitochondrial F1–ATPase β subunit from *Nicotiana plumbaginifolia* import CAT and GUS proteins into mitochondria of transgenic plants. *Plant Mol. Biol.* 24, 631–641.

Chaumont. F., et al. (1997). Expression of an Arabidopsis plasma membrane aquaporin in Dictyostelium results in hypoosmotic sensitivity and developmental abnormalities. *Proc. Natl Acad. Sci. USA.* 94, 6202–6209.

Chaumont, F., et al. (1998) Characterization of a maize tonoplast aquaporin expressed in zones of cell division and elongation. *Plant Physiol.* 117, 1143–1152.

Daniels, M., et al. (1994) The plasma membrane of *Arabidopsis thaliana* contains a mercury–insensitive aquaporin that is a homolog of the tonoplat water channel protein TIP. *Plant Physiol* 106: 1325–1333.

Daniels, M., et al. (1996) Characterization of a new vacuolar membrane aquaporin in Arabidopsis and identification of a unique mercury sensitivity site in aquaporins. *Plant Cell* 8: 587–599.

Gerbeau, P., et al. (1999) Aquaporin Nt–TIPa can account for the high permeability of tobacco cell vacuolar membrane to small neutral solutes. *Plant J.,* in press.

Johansson, I., et al. (1996) The major integral proteins of spinach leaf plasma membranes are putative aquaporins and are phosphorylated in response in CA2+ and apoplastic water potential. *Plant Cell,* 8, 1181–1191.

Johansson, I., et al. (1998). Water transport activity of the plasma membrane aquaporin PM28A is regulated by phosphorylation. *Plant Cell* 10:451–460.

Larsson, C., et al. (1994). Isolation of highly purified plasma membranes and the separation of inside–out and right–side–out vesicles. Methods Enzymol. 228, 451–469.

Maurel, C., et al. (1993). The vacuolar membrane protein—TIP creates water specific channels in *Zenopus oocytes. EMBO J* 12:2241–2247.

Maurel, C., et al. (1997). Aquaporins and water permeability of plant membranes. *Annual Rev Plant Physiol Plant Mol Biol* 48: 399–429.

Maurel, C., et al. (1997). Purified vesicles of tobacco cell vacuolar and plasma membranes exhibit dramatically different water permeability and water channel activity. *Proc Natl Acad Sci USA* 94:7103–7108.

Park, J., et al. (1996). Phylogenetic characterization of the MIP family of transmembrane channel proteins. *J Membr Biol* 153: 171–180.

Weig, A., et al. (1997). The major intrinsic protein family of Arabidopsis has 23 members that form three distinct groups with functional aquaporins in each group. *Plant Physiol* 114:1347–1357.

* cited by examiner

*Primary Examiner*—David T. Fox
*Assistant Examiner*—Medina A. Ibrahim
(74) *Attorney, Agent, or Firm*—Pioneer Hi-Bred International, Inc.

(57) ABSTRACT

The invention provides isolated maize aquaporin nucleic acids and their encoded proteins. The present invention provides methods and compositions relating to altering aquaporin concentration and/or composition of plants. The invention further provides recombinant expression cassettes, host cells, transgenic plants, and antibody compositions.

40 Claims, No Drawings

MAIZE AQUAPORINS AND USES THEREOF

CROSS-REFERENCE TO RELATED APPLICATIONS

This application claims the benefit of priority of U.S. Provisional Patent Application Serial No. 60/098,692 filed Aug. 13, 1998, which is herein incorporated by reference.

TECHNICAL FIELD

The present invention relates generally to plant molecular biology. More specifically, it relates to nucleic acids and methods for modulating their expression in plants.

BACKGROUND OF THE INVENTION

Aquaporins are water channel proteins present in the membranes of plants and animal cells and belong to a family of proteins known as the MIP (membrane intrinsic protein) family. Maurel et al, *J. Exp. Botany*, 48: Special Issue, 421–430, 1997. These proteins exhibit a typical structure of 24–28 kDa with six predicted transmembrane spanning domains and some perfectly conserved residues including an Asn-Pro-Ala motif, in both the first intra-cytoplasmic and third extracytoplasmic loops of the protein. Reizer et al., *Critical Reviews in Biochemistry and Molecular Biology*, 28: 235–57, 1993. Within the plant cell, aquaporins are found in both the vacuolar and plasma membranes.

Aquaporins are involved in: cell expansion and cell volume regulation, transcellular water flow, adjustments to water deficit, regulated water delivery, and adaptation to cold stress by osmotic adjustments. Some aquaporins have been shown to be desiccation and salt stress induced in plants. Yamaguchi-Shinozaki et al., *Plant Cell Physiol.*, 33: 217–224, 1992; Guerrero et al., *Plant Mol. Biol.*, 15: 11–26, 1990. Kaldenhoff et al., (*Plant J.*, 7: 87–95, (1995)) showed that the down-regulation of aquaporins in Arabidopsis plants that express antisense constructs results in a slower swelling and bursting of the isolated protoplasts.

Tonoplast Intrinsic Proteins (TIP) are MIP homologs that have been identified in seeds from a wide range of monocot and dicot species. Johnson et al., *Plant Physiology*, 91: 1006–13, 1989. Full or partial sequences have been determined in bean (Johnson et al., *Plant Cell*, 2: 525–32, 1990), *Arabidopsis thaliana* (Hofte et al., *Plant Physiology*, 99: 561–70, 1992), pumpkin (Cucurbita sp.) (Inoue et al., *Plant Molecular Biology*, 28: 1089–1101, 1995), and Norway spruce (*Picea abies*) (Oliviusson and Hakman, *Physiologia Plantarum*, 95: 288–95, 1995) and confirm the high conservation of these proteins in seeds. Full or partial sequences of more than 20 MIP homologs in Arabidopsis are reported to be available in the sequence data banks. Maurel et al., *J. Exp. Botany*, 48: Special Issue, 421–430, 1997.

An important parameter of crop plants is water use efficiency. Plants able to make better use of scarce water resources promise to make agriculture more sustainable in many areas of the U.S. and the world. Accordingly, what is needed in the art are plants which are desiccation-, salt-, cold-, or drought-tolerant. The present invention provides this and other advantages.

SUMMARY OF THE INVENTION

Generally, it is the object of the present invention to provide nucleic acids and proteins relating to maize aquaporins. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from the group consisting of (a) a polynucleotide which encodes a polypeptide of SEQ ID NOS: 2, 4, 6, 8, 10, 12, 14, 16, 18, 20, 22, 24, 26, 28, 30, 32, 34, 36, 38, 40, 42, 44, 46 and 48; (b) a polynucleotide comprising at least 25 contiguous bases of SEQ ID NOS; (c) a polynucleotide encoding a maize aquaporin; (d) a polynucleotide having at least 80% sequence identity to SEQ ID NOS: 1, 3, 5, 7, 9, 11, 13, 15, 17, 19, 21, 23, 25, 27, 29, 31, 33, 35, 37, 38, 39, 41, 43, 45, and 47; wherein the % sequence identity is based on the entire sequence and is determined by GAP analysis using Gap Weight of 50 and Length Weight of 3; (e) a polynucleotide comprising at least 25 nucleotides in length which hybridizes under stringent conditions to a polynucleotide having the sequence set forth in SEQ ID NOS: 1, 3, 5, 7, 9, 11, 13, 15, 17, 19, 21, 23, 25, 27, 29, 31, 33, 35, 37, 38, 39, 41, 43, 45, and 47; (g) a polynucleotide having the sequence set forth in SEQ ID NOS: 1, 3, 5, 7, 9, 11, 13, 15, 17, 19, 21, 23, 25, 27, 29, 31, 33, 35, 37, 38, 39, 41, 43, 45, and 47; (h) a polynucleotide complementary to a polynucleotide of (a) through (g). The isolated nucleic acid can be DNA.

In another aspect, the present invention relates to recombinant expression cassettes, comprising a nucleic acid as described, supra, operably linked to a promoter. In some embodiments, the nucleic acid is operably linked in antisense orientation to the promoter.

In another aspect, the present invention is directed to a host cell transfected with the recombinant expression cassette as described, supra. In some embodiments, the host cell is a corn, soybean, wheat, rice, alfalfa, barley, millet, sunflower, sorghum, canola or cotton cell.

In a further aspect, the present invention relates to an isolated protein comprising a polypeptide having 10 contiguous amino acids encoded by the isolated nucleic acid referred to, supra.

In another aspect, the present invention relates to an isolated nucleic acid comprising a polynucleotide of at least 25 contiguous bases which selectively hybridizes under stringent conditions to a nucleic acid of the present invention, or a complement thereof. In some embodiments, the isolated nucleic acid is operably linked to a promoter.

In yet another aspect, the present invention relates to an isolated nucleic acid comprising a polynucleotide, the polynucleotide having a specified sequence identity to an identical length of a nucleic acid of the present invention or a complement thereof.

In another aspect, the present invention relates to an isolated nucleic acid adducted to a second nucleic acid sequences encoding a DNA-binding domain.

In an additional aspect, the present invention is directed to an isolated nucleic acid comprising a polynucleotide encoding a polypeptide wherein: (a) a polypeptide comprising at least 10 contiguous amino acids of SEQ ID NOS: 2, 4, 6, 8, 10, 12, 14, 16, 18, 20, 22, 24, 26, 28, 30, 32, 34, 36, 38, 40, 42, 44, 46 and 48; (b) a polypeptide which is a maize aquaporin; (c) a polypeptide having at least 60% sequence similarity to SEQ ID NOS: 2, 4, 6, 8, 10, 12, 14, 16, 18, 20, 22, 24, 26, 28, 30, 32, 34, 36, 38, 40, 42, 44, 46 and 48; wherein the % sequence similarity is based on the entire sequence and is determined by GAP analysis using Gap Weight of 12 and Length Weight of 4; (d) a polypeptide encoded by a nucleic acid of claim 1; (e) a polypeptide encoded by a nucleic acid of SEQ ID NOS: 1, 3, 5, 7, 9, 11, 13, 15, 17, 19, 21, 23, 25, 27, 29, 31, 33, 35, 37, 38, 39, 41, 43, 45, and 47.

In yet another aspect, the present invention relates to a transgenic plant comprising a recombinant expression cassette comprising a plant promoter operably linked to any of the isolated nucleic acids of the present invention. In some embodiments, the transgenic plant is *Zea mays*. The present invention also provides transgenic seed from the transgenic plant.

In a further aspect, the present invention relates to a method of modulating expression of the genes encoding the proteins of the present invention in a plant, comprising the steps of (a) transforming a plant cell with the expression cassette of claim 4; (b) growing the plant cell under plant growing conditions to produce a regenerated plant; and (c) inducing expression of the polynucleotide for a time sufficient to modulate aquaporin in the plant. Expression of the genes encoding the proteins of the present invention can be increased or decreased relative to a non-transformed control plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, $F(ab)_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, Antibodies, A Laboratory Manual, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "aquaporin nucleic acid" is a nucleic acid of the present invention and means a nucleic acid comprising a polynucleotide of the present invention (a "aquaporin polynucleotide") encoding an aquaporin polypeptide. A "aquaporin gene" is a gene of the present invention and refers to a non-heterologous genomic form of a full-length aquaporin polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties*, 2nd ed., T. E. Creighton, W. H. Freeman and Company, New York (1993). Many detailed reviews are available on this subject, such as, for example, those provided by Wold, F., Post-translational Protein Modifications: Perspectives and Prospects, pp. 1–12 in *Posttranslational Covalent Modification of Proteins*, B. C. Johnson, Ed., Academic Press, New York (1983); Seifter et al., *Meth. Enzymol*. 182: 626–646 (1990) and Rattan et al., *Protein Synthesis: Posttranslational Modifications and Aging, Ann. N.Y. Acad. Sci*. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "aquaporin polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "aquaporin protein" is a protein of the present invention and comprises an aquaporin polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used o determine selective reactivity.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Hybridization times may range from four hours to sixteen hours and are not a factor in degree of stringency.

Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.*, 138: 267–284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about ° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-lnterscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif. GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, CABIOS 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-lnterscience, New York (1995).

Unless otherwise stated, sequence identity/similarity values provided herein refer to the value obtained using GAP v.10 using the following parameters: % identity using GAP Weight of 50 and Length Weight of 3; % similarity using Gap Weight of 12 and Length Weight of 4.

GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

As those of ordinary skill in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, inter alla, compositions and methods for modulating (i.e., increasing or decreasing) the level of polypeptides of the present invention in plants. In particular, the polypeptides of the present invention can be expressed at developmental stages, in tissues, and/or in quantities which are uncharacteristic of non-recombinantly engineered plants. Thus, the present invention provides utility in such exemplary applications as the engineering of plants which are desiccation-, salt-, cold-, or drought-tolerant.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of polypeptides of the present invention.

The isolated nucleic acids and proteins of the present invention can be used over a broad range of plant types, particularly monocots such as the species of the Family Graminiae including *Sorghum bicolor* and *Zea mays*. The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, and Triticum.

Nucleic Acids

The present invention provides, inter alia, isolated nucleic acids of RNA, DNA, and analogs and/or chimeras thereof, comprising a polynucleotide of the present invention.

A polynucleotide of the present invention is inclusive of:

(a) a polynucleotide which encodes a polypeptide of SEQ ID NOS: 2, 4, 6, 8, 10, 12, 14, 16, 18, 20, 22, 24, 26, 28, 30, 32, 34, 36, 38, 40, 42, 44, 46 and 48;

(b) a polynucleotide comprising at least 25 contiguous bases of SEQ ID NOS:

(c) a polynucleotide encoding a maize aquaporin;

(d) a polynucleotide having at least 80% sequence identity to SEQ ID NOS: 1, 3, 5, 7, 9, 11, 13, 15, 17, 19, 21, 23, 25, 27, 29, 31, 33, 35, 37, 38, 39, 41, 43, 45, and 47; wherein the % sequence identity is based on the entire sequence and is determined by GAP analysis using Gap Weight of 50 and Length Weight of 3;

(e) a polynucleotide comprising at least 25 nucleotides in length which hybridizes under stringent conditions to a polynucleotide having the sequence set forth in SEQ ID NOS: 1, 3, 5, 7, 9, 11, 13, 15, 17, 19, 21, 23, 25, 27, 29, 31, 33, 35, 37, 38, 39, 41, 43, 45, and 47;

(f) a polynucleotide having the sequence set forth in SEQ ID NOS: 1, 3, 5, 7, 9, 11, 13, 15, 17, 19, 21, 23, 25, 27, 29, 31, 33, 35, 37, 38, 39, 41, 43, 45, and 47;

(g) a polynucleotide complementary to a polynucleotide of (a) through (g).

A. Polynucleotides Encoding A Polypeptide of the Present Invention or Conservatively Modified or Polymorphic Variants Thereof As indicated in (a), supra, the present invention provides isolated nucleic acids comprising a polynucleotide of the present invention, wherein the polynucleotide encodes a polypeptide of the present invention, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 3, 5, 7, 9, 11, 13, 15, 17, 19, 21, 23, 25, 27, 29, 31, 33, 35, 37, 39, 41, 43, 45, and 47 and silent variations of polynucleotides encoding a polypeptide of SEQ ID NOS: 2, 4, 6, 8, 10, 12, 14, 16, 18, 20, 22, 24, 26, 28, 30, 32, 34, 36, 38, 40, 42, 44, 46, and 48. The present invention further provides isolated nucleic acids comprising polynucleotides encoding conservatively modified variants of a polypeptide of SEQ ID NOS: 2, 4, 6, 8, 10, 12, 14, 16, 18, 20, 22, 24, 26, 28, 30, 32, 34, 36, 38, 40, 42, 44, 46, and 48. Conservatively modified variants can be used to generate or select antibodies immunoreactive to the non-variant polypeptide. Additionally, the present invention further provides isolated nucleic acids comprising polynucleotides encoding one or more polymorphic (allelic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

As indicated in (b), supra, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28–38.); see also, U.S. Pat. No. 5,470,722, and *Current Protocols in Molecular Biology*, Unit 15.6, Ausubel, et al., Eds., Greene Publishing and Wiley-lnterscience, New York (1995); Frohman and Martin, *Techniques* 1:165 (1989).

C. Polynucleotides Which Selectively Hybridize to a Polynucleotide of (A) or (B)

As indicated in (c), supra, the present invention provides isolated nucleic acids comprising polynucleotides of the present invention, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), supra, the present invention provides isolated nucleic acids comprising polynucleotides of the present invention, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising polynucleotides of the present invention, wherein the polynucleotides encode a protein having a subsequence of contiguous amino acids from a prototype polypeptide of the present invention such as are provided in (a), supra. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), supra. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassay, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Preferably, the molecular weight is within 15% of a full length polypeptide of the present invention, more preferably within 10% or 5%, and most preferably within 3%, 2%, or 1% of a full length polypeptide of the present invention. Molecular weight determination of a protein can be conveniently performed by SDS-PAGE under denaturing conditions.

F. Polynucleotides Complementary to the Polynucleotides of (A)–(E)

As indicated in (f), supra, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), supra, the present invention provides isolated nucleic acids comprising polynucleotides which comprise at least 15 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype polypeptide sequence as provided in (a), supra, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is *Zea mays*.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res*., 18(19):5705–5711 (1990); Patanjali et al., *Proc. Natl. Acad. U.S.A*., 88:1943–1947 (1991); U.S. Pat. Nos. 5,482,685, and 5,637,685. In an exemplary method described by Soares et al, normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, Technique, 3(2):58–63 (1991); Sive and St. John, *Nucl. Acids Res*., 16(22):10937 (1988); *Current Protocols in Molecular Biology*, Ausubel, et al., Eds., Greene Publishing and Wiley-lnterscience, New York (1995); and, Swaroop et al., *Nucl. Acids Res*., 19)8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152*: Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol*. 68: 90–99 (1979); the phosphodiester method of Brown et al., *Meth. Enzymol*. 68: 109–151 (1979); the diethylphosphoramidite method of Beaucage et al., *Tetra. Lett*. 22: 1859–1862 (1981); the solid phase phosphoramidite triester method described by Beaucage and Caruthers, *Tetra. Letts*. 22(20): 1859–1862 (1981), e.g., using an automated synthesizer, e.g., as described in Needham-VanDevanter et al., *Nucleic Acids Res*., 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations. Preferred tissue-preferred promoters include the wheat peroxidase promoter (Hertig, et al., *Plant Mol. Biol.* 16 :171–174 (1991)); the rice bacilliform tungro viral promoter (Matsumura, T., and Tabayashi, N., *Semin Virol.* 6: 133–139 (1995)); and, the BET1 promoter (Hueros, et al., *Plant Cell* June 1995;7(6): 747–757 (1995).

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., The *Maize Handbook*, Chapters 114–115, Freeling and Walbot, Eds., Springer, N.Y. (1994); *Corn and Corn Improvement*, 3$^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, N.Y., (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptll gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., *Meth. In Enzymol.*, 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that antisense RNA inhibits gene expression by preventing the accumulation of mRNA which encodes the enzyme of interest, see, e.g., Sheehy et al., *Proc. Natl. Acad. Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al, *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,68, 1941.

Proteins

The isolated proteins of the present invention comprise a polypeptide having at least 10 amino acids encoded by any one of the polynucleotides of the present invention as discussed more fully, supra, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastors*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev*. 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J. Embryol. Exp. Morphol*. 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol*. 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in DNA *Cloning Vol. II a Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

Isolated nucleic acid acids of the present invention can be introduced into plants according techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al, *Ann. Rev. Genet*. 22: 421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J*. 3: 2717–2722 (1984). Electroporation techniques are described in Fromm et al., *Proc. Natl. Acad. Sci*. 82: 5824 (1985). Ballistic transformation techniques are described in Klein et al., *Nature* 327: 70–73 (1987).

*Agrobacterium tumefaciens*-meditated transformation techniques are well described in the scientific literature. See, for example Zhao, et al. (WO US98/01268); Horsch et al., *Science* 233: 496–498 (1984), and Fraley et al., *Proc. Natl. Acad. Sci*. 80: 4803 (1983). Although Agrobacterium is useful primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25: 1353, 1984), (3) the vortexing method (see, e.g., Kindle, *Proc. Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding genes can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology*. Vol 2: *Special Methods in Peptide Synthesis*, Part A.; Merrifield, etal., *J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purifcation*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al, *Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium from leaf explants can be achieved as described by Horsch et al., *Science*, 227: 1229–1231 (1985). In this procedure, transformants are grown in the presence of a selection agent and in a medium that induces the regeneration of shoots in the plant species being transformed as described by Fraley et al., *Proc. Nati. Acad. Sci. U.S.A.*, 80: 4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Com and Com Improvement*, 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

Modulating Polypeptide Levels and/or Composition

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology. A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res*.15:8125 (1987)) and the 7-methylguanosine cap structure (Drummond et al., *Nucleic Acids Res*. 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res*. 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.- H., et al. *Proc. Natl. Acad. Sci. USA* 94: 4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: In situ Hybridization, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz, M., and Kurz, K., A *Colorimetric Method for DNA Hybridization, Nucl. Acids Res*. 12: 3435–3444 (1984)) and synthetic oligonucleotides have been coupled directly with alkaline phosphatase (Jablonski, E., et al., *Preparation of Oligodeoxynucleotide-Alkaline Phosphatase Conjugates and Their Use as Hybridization Probes, Nuc. Acids. Res*. 14: 6115–6128 (1986); and Li P., et al., *Enzyme-linked Synthetic Oligonucleotide probes: Non-Radioactive Detection of Enterotoxigenic Escherichia Coli in Faeca Specimens, Nucl. Acids Res*. 15: 5275–5287 (1987)).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quartenary structure. Non-isolated polypeptides of the present invention can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., *Science* 246: 1275–1281 (1989); and Ward, et al., *Nature* 341: 544–546 (1989); and Vaughan et al., *Nature Biotechnology*, 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech*., 14: 845–851 (1996). Also, recombinant immunoglobulins may be produced. See, Cabilly, U.S. Pat. No. 4,816,567; and Queen etal., *Proc. Nat'l. Acad. Sci*. 86: 10029–10033 (1989).

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassaysm*, Price and Newman Eds., Stockton Press, NY (1991); and *Non-isotopic Immunoassays*, Ngo, Ed., Plenum Press, NY (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval, et al., *J. Immunol.* 111: 1401–1406 (1973), and Akerstrom, et al., *J. Immunol.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Noncompetitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for use in Immunoassays

A protein that specifically binds to or that is specifically immunoreactive with an antibody generated against a defined immunogen is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570–573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and calorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

The biological activity of aquaporins is usually determined with Xenopus oocyte swelling assays (Maurel et al, 1993). MIP cRNA is injected into oocytes and after a 3-day incubation the oocytes are shifted to a hypotonic medium. If water channel proteins are present in the plasma membrane, the oocytes swell and burst much faster than the control oocytes. In these conditions oocytes injected with the plasma membrane AtRD28 aquaporin (Daniels et al., 1994) or maize aquaporin cRNAs rapidly increase their volume, indicating the presence of a facilitated water-transport pathway. The osmotic water permeability coefficient (Pf) of the oocyte membrane increases 8-fold over the control. Mercurial compounds were characteristic inhibitors of many water-channel proteins. Water transport through maize aquaporins are inhibited 50% by 1 mM mercuric chloride and this inhibition is reversed by the reducing agent -mercaptoethanol.

The following examples are offered by way of illustration and not by way of limitation.

EXAMPLE 1

This example describes the construction of cDNA libraries.

Total RNA Isolation

Total RNA was isolated from corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+RNA Isolation

The selection of poly(A)+RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 $cm^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 $cm^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2nd Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire corn partial sequence database.
4. A Sal-A20 oligo nucleotide: TCG ACC CAC GCG TCC GAA AAA AAA AA AAA AAA AAA, (SEQ ID NO. 49) removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, S. F., et al., (1993) *J. Mol. Biol.* 215: 403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. (1993) *Nature Genetics* 3: 266–272) provided by the NCBI. In some cases, the sequencing data from two or more clones containing overlapping segments of DNA were used to construct contiguous DNA sequences. Table 1 shows the results of the homology search and the library number and tissue from which the library was made. JA=jasmonic acid; DAP=days after pollination.

TABLE 1

| SEQ. ID NO'S | GENE NAME (match to public database) | TISSUE TYPE AND TREATMENT |
|---|---|---|
| 1, 2 | *Z. mays* mRNA for transmembrane protein | Etiolated seedlings, 8 hr post infection |
| 3, 4 | *Z. mays* mRNA for transmembrane protein | Heat Shock recovery seedling (8 hr) |
| 5, 6 | *Z. mays* mRNA for transmembrane protein | Early Meiosis Tassels (16–18 cm) |
| 7, 8 | MipC [*Mesembryanthemum crystallinum*] | Green leaves, JA treated, normalized |
| 9, 10 | MipC [*Mesembryanthemum crystallinum*] | Green leaves, JA treated |
| 11, 12 | Aquaporin [*Atriplex canescens*] | Corn Root Worm infested roots |
| 13, 14 | MipC [*Mesembryanthemum crystallinum*] | Germinating Maize seeds, scutelar node |
| 15, 16 | MipC [*Mesembryanthemum* crystallinum] | Regeneration callus, 10 & 14 days |
| 17, 18 | *Z. mays* mRNA for transmembrande protein | Leaf |
| 19, 20 | Tonoplast intrinsic protein [*Arabidopsis thaliana*] | Leaf:induced resistance prior to genetic |
| 21, 22 | Integral membrane protein [*Antirrhinum majus*] | Root tips, <5 mm in length |
| 23, 24 | Integral membrane protein [*Antirrhinum majus*] | Germinating Maize seeds, 2 & 3 days, roots |
| 25, 26 | Complete cds [*Rattus norvegicus*] | Leaf |
| 27, 28 | Delta-tonoplast intrinsic protein [*Gossypium hirsutum*] | Leaf |
| 29, 30 | mucin 2 (intestinal mucin 2) (fragments). | Premeitoic > early uninucleate tassle |
| 31, 32 | Tonoplast intrinsic protein [*Arabidopsis thaliana*] | 40 DAP Endosperm |
| 33, 34 | Gamma-Tip [*Oryza sativa*] | Pollen at pollen shed |
| 35, 36 | Aquaporin [*Helianthus annuus*] | CM 45 Shoot Culture |
| 37, 38 | Major intrinsic protein [*Oryza sativa*] | Green leaves, JA treated |
| 39, 40 | Major intrinsic protein [*Oryza sativa*] | Leaf |
| 41, 42 | Nodulin-26 - soybean | 5 DAP Whole Kernels |
| 43, 44 | Putative membrane integral protein [*Nicotiana alata*] | CM 45 Shoot Culture |
| 45, 46 | Nodulin-26 - soybean | Premeitoic > early uninucleate tassle |
| 47, 48 | Aquaporin [*Helianthus annuus*] | Corn Root Worm infested roots |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated polynucleotide comprising a member selected from the group consisting of:

(a) a polynucleotide which encodes a polypeptide of SEQ ID NOS: 4, 8, 10, 12, 14, 16, 18, 20, 22, 24, 26, 28, 30, 32, 34, 36, 38, 40, 42, 44, 46, or 48;

(b) a polynucleotide having the sequence set forth in SEQ ID NOS: 3, 5, 7, 9, 11, 13, 15, 17, 19, 21, 23, 25, 27, 29, 31, 33, 35, 37, 39, 41, 43, 45, or 47; and (c) a polynucleotide complimentary to a polynucleotide of (a) or (b); wherein the polynucleotide of (c) encodes maize aquaporin.

2. The isolated nucleic acid of claim 1 adducted to a second nucleic acid sequence encoding a DNA-binding domain.

3. A vector comprising at least one nucleic acid of claim 1.

4. An expression cassette comprising at least one nucleic acid of claim 1 operably linked to a promoter.

5. The expression cassette of claim 4, wherein the nucleic acid is operably linked in antisense orientation to the promoter.

6. A host cell introduced with at least one expression cassette of claim 4.

7. The host cell of claim 6 which is a plant cell.

8. A transgenic plant comprising at least one expression cassette of claim 4.

9. The transgenic plant of claim 8, wherein the plant is corn, soybean, wheat, rice, alfalfa, barley, millet, sunflower, sorghum, non-vegetable brassica or cotton.

10. A seed from the transgenic plant of claim 8.

11. The seed of claim 10, wherein the seed is from corn, soybean, wheat, rice, alfalfa, barley, millet, sorghum, sunflower, canola or cotton.

12. An isolated ribonucleic acid sequence encoding a polypeptide comprising a member selected from the group consisting of:

(a) a polypeptide having at least 99% sequence similarity to SEQ ID NO:4 wherein the % sequence similarity is based on the entire sequence and is determined by GAP analysis using Gap Weight of 12 and Length Weight of 4;

(b) a polypeptide having at least 92% sequence similarity to SEQ ID NOS: 10 12, 14, 16, 18, 22, 24, or 48, wherein the % sequence similarity is based on the entire sequence and is determined by GAP analysis using Gap Weight of 12 and Length Weight of 4; and (c) a polypeptide having at least 84% sequence similarity to SEQ ID NOS: 8, 20, 26, 28, 30, 32, 34, 36, 38, 40, 42, 44, or 46, wherein the % sequence similarity is based on the entire sequence and is determined by GAP analysis using Gap Weight of 12 and Length Weight of 4; wherein the polypeptide of (a) or (b) is maize aquaporin.

13. A method of modulating the level of aquaporin in a plant, comprising:

(a) transforming a plant cell with the expression cassette of claim 4;

(b) growing the plant cell under plant growing conditions to produce a regenerated plant; and (c) inducing expression of the polynucleotide for a time sufficient to modulate aquaporin in the plant.

14. The method of claim 13, wherein the plant is corn, soybean, wheat, rice, alfalfa, barley, millet, sorghum, sunflower, non-vegetable brassica or cotton.

15. The method of claim 13, wherein the level of aquaporin is increased.

16. The method of claim 13, wherein the level of aquaporin is decreased.

17. An isolated polynucleotide comprising a member selected from the group consisting of:

(a) a polynucleotide comprising at least 50 contiguous bases of the encoding region of SEQ ID NOS: 9, 11, 17, 19, 21, 23, 25, 27, 29, 31, 33, 35, 37, 39, 41, 43, 45, or 47; and (b) a polynucleotide complimentary to a polynucleotide of (a), wherein (a) or (b) encodes maize aquaporin.

18. An isolated polynucleotide comprising a member selected from the group consisting of:

(a) a polynucleotide having at least:

(I) 99% sequence identity to SEQ ID NOS: 3 or 5, wherein the % sequence identity is based on the entire encoding region and is determined by GAP analysis using GAP Weight of 50 and Length Weight of 3; or (ii) 90% sequence identity to SEQ ID NOS: 9, 11, 13, 15, or 17, wherein the % sequence identity is based on the entire encoding region and is determined by GAP analysis using GAP Weight of 50 and Length Weight of 3; or (iii) 80% sequence identity to SEQ ID NOS: 7, 19, 21, 23, 25, 27, 29, 31, 33, 35, 37, 39, 41, 43, 45, or 47, wherein the % sequence identity is based on the entire encoding region and is determined by GAP analysis using GAP Weight of 50 and Length Weight of 3; and (b) a polynucleotide complimentary to a polynucleotide of (a), wherein (a) or (b) encodes maize aquaporin.

19. The isolated nucleic acid of claim 18 adducted to a second nucleic acid sequence encoding a DNA-binding domain.

20. A vector comprising at least one nucleic acid of claim 18.

21. An expression cassette comprising at least one nucleic acid of claim 18 operably linked to a promoter.

22. The expression cassette of claim 21, wherein the nucleic acid is operably linked in antisense orientation to the promoter.

23. A host cell introduced with at least one expression cassette of claim 21.

24. The host cell of claim 23 which is a plant cell.

25. A transgenic plant comprising at least one expression cassette of claim 21.

26. The transgenic plant of claim 25, wherein the plant is corn, soybean, wheat, rice, alfalfa, barley, millet, sunflower, sorghum, non-vegetable brassica or cotton.

27. A seed from the transgenic plant of claim 25.

28. The seed of claim 27, wherein the seed is from corn, soybean, wheat, rice, alfalfa, barley, millet, sorghum, sunflower, canola or cotton.

29. A method of modulating the level of aquaporin in a plant, comprising:

(a) transforming a plant cell with the expression cassette of claim 21;

(b) growing the plant cell under plant growing conditions to produce a regenerated plant; and (c) inducing expression of the polynucleotide for a time sufficient to modulate aquaporin in the plant.

30. The isolated nucleic acid of claim 21 adducted to a second nucleic acid sequence encoding a DNA-binding domain.

31. A vector comprising at least one nucleic acid of claim 21.

32. An expression cassette comprising at least one nucleic acid of claim 21 operably linked to a promoter.

33. The expression cassette of claim 32, wherein the nucleic acid is operably linked in antisense orientation to the promoter.

34. A host cell introduced with at least one expression cassette of claim 32.

35. The host cell of claim 34 which is a plant cell.

36. A transgenic plant comprising at least one expression cassette of claim 32.

37. The transgenic plant of claim 36, wherein the plant is corn, soybean, wheat, rice, alfalfa, barley, millet, sunflower, sorghum, non-vegetable brassica or cotton.

38. A seed from the transgenic plant of claim 36.

39. The seed of claim 38, wherein the seed is from corn, soybean, wheat, rice, alfalfa, barley, millet, sorghum, sunflower, canola or cotton.

40. A method of modulating the level of aquaporin in a plant, comprising:

(a) transforming a plant cell with the expression cassette of claim 32;

(b) growing the plant cell under plant growing conditions to produce a regenerated plant; and (c) inducing expression of the polynucleotide for a time sufficient to modulate aquaporin in the plant.

* * * * *

UNITED STATES PATENT AND TRADEMARK OFFICE

CERTIFICATE OF CORRECTION

PATENT NO. : 6,313,375 B1
DATED : November 6, 2001
INVENTOR(S) : Rudolf Jung et al.

It is certified that error appears in the above-identified patent and that said Letters Patent is hereby corrected as shown below:

Column 141,
Line 18, delete "claim 21" and insert -- claim 17 --.
Lines 21 and 22, delete "claim 21" and insert -- claim 17 --.
Line 24, delete "claim 21" and insert -- claim 17 --.

Signed and Sealed this

Thirtieth Day of July, 2002

*Attest:*

JAMES E. ROGAN

*Attesting Officer*

*Director of the United States Patent and Trademark Office*

SEQUENCE LISTING

```
<160> NUMBER OF SEQ ID NOS: 49

<210> SEQ ID NO 1
<211> LENGTH: 1445
<212> TYPE: DNA
<213> ORGANISM: Zea mays
<220> FEATURE:
<221> NAME/KEY: CDS
<222> LOCATION: (202)...(1069)

<400> SEQUENCE: 1

cccgggtcga cccacgcgtc cgtgctcact ctcctcacca ctaccctgac ctgacctgct      60

cccaagctcc ctctgcctgc ctttataaat caccggggca gagcgcctca gtgacacacg     120

ccgctgctcc aagaaaccac cgccgagccc aaccgcacaa gcgcgcgagg caggagagag     180

agagaggcgg ggagcaaaac a atg gag ggg aaa gag gag gac gtg cgc ctg       231
                        Met Glu Gly Lys Glu Glu Asp Val Arg Leu
                         1               5                  10

ggc gcc aac aag ttc tcg gag cgc cag ccc atc ggg acg gcg gcg cag       279
Gly Ala Asn Lys Phe Ser Glu Arg Gln Pro Ile Gly Thr Ala Ala Gln
                15                  20                  25

ggc gcc gct gac gac aag gac tac aag gag ccc ccg ccg gcg ccg ctg       327
Gly Ala Ala Asp Asp Lys Asp Tyr Lys Glu Pro Pro Pro Ala Pro Leu
            30                  35                  40

ttc gag ccc ggg gag ctc aag tcc tgg tcc ttc tac cgc gcg ggc atc       375
Phe Glu Pro Gly Glu Leu Lys Ser Trp Ser Phe Tyr Arg Ala Gly Ile
        45                  50                  55

gcc gag ttc gtc gcc acc ttc ctc ttc ctc tac atc acc atc ctc acc       423
Ala Glu Phe Val Ala Thr Phe Leu Phe Leu Tyr Ile Thr Ile Leu Thr
    60                  65                  70

gtc atg ggc gtc tcc aag tcc acc tcc aag tgc gcc acc gtc ggc atc       471
Val Met Gly Val Ser Lys Ser Thr Ser Lys Cys Ala Thr Val Gly Ile
 75                  80                  85                  90

cag ggc atc gcc tgg tcc ttc gga gga atg atc ttc gcg ctc gtc tac       519
Gln Gly Ile Ala Trp Ser Phe Gly Gly Met Ile Phe Ala Leu Val Tyr
                95                 100                 105

tgc acc gcc ggc atc tcc gga gga cac atc aac cca gct gtg act ttc       567
Cys Thr Ala Gly Ile Ser Gly Gly His Ile Asn Pro Ala Val Thr Phe
            110                 115                 120

ggg ctg ttc tta gcc agg aag ctg tcc ctg act agg gcc ctc ttc tac       615
Gly Leu Phe Leu Ala Arg Lys Leu Ser Leu Thr Arg Ala Leu Phe Tyr
        125                 130                 135

atc atc atg caa tgc ctg ggt gcc atc tgt gga gct gga gtg gtg aag       663
Ile Ile Met Gln Cys Leu Gly Ala Ile Cys Gly Ala Gly Val Val Lys
    140                 145                 150

ggc ttc cag cag gga ctt tac atg ggc aac ggt ggt ggc gcc aat gtt       711
Gly Phe Gln Gln Gly Leu Tyr Met Gly Asn Gly Gly Gly Ala Asn Val
155                 160                 165                 170

gtc gca cct ggc tac acc aag ggt gat ggc ctt ggc gct gag att gtt       759
Val Ala Pro Gly Tyr Thr Lys Gly Asp Gly Leu Gly Ala Glu Ile Val
                175                 180                 185

ggc acc ttc atc cta gtc tac acc gtc ttc tca gcc acc gat gcc aag       807
Gly Thr Phe Ile Leu Val Tyr Thr Val Phe Ser Ala Thr Asp Ala Lys
            190                 195                 200

agg aat gcc agg gac tcc cat gtt cct atc ctt gcc cca ctg cca att       855
Arg Asn Ala Arg Asp Ser His Val Pro Ile Leu Ala Pro Leu Pro Ile
        205                 210                 215

ggg ttc gcg gtg ttc ctg gtc cac ctt gcc acc atc ccc att act ggc       903
Gly Phe Ala Val Phe Leu Val His Leu Ala Thr Ile Pro Ile Thr Gly
```

-continued

```
    220                 225                 230

act ggc atc aac cca gct agg agc ctt ggc gct gcc atc atc tac aac      951
Thr Gly Ile Asn Pro Ala Arg Ser Leu Gly Ala Ala Ile Ile Tyr Asn
235                 240                 245                 250

agg gat cac gcc tgg aac gac cat tgg atc ttc tgg gtc ggc ccc ttc      999
Arg Asp His Ala Trp Asn Asp His Trp Ile Phe Trp Val Gly Pro Phe
                255                 260                 265

att ggc gct gct ctg gct gcc atc tac cac cag gtg atc atc aga gcc     1047
Ile Gly Ala Ala Leu Ala Ala Ile Tyr His Gln Val Ile Ile Arg Ala
            270                 275                 280

atc ccg ttc aag agc agg tct t aagctgccgt ggccgtgccg agacatgcca      1099
Ile Pro Phe Lys Ser Arg Ser
        285

gtccgaagaa cgggcgtctt cctgtgatgt cttcttgtct gcccacgcct agtttctctg   1159

tcgattccta ttcgtcgtct cttcagggct ggtgctcact gctgcgccgt tctgttaacc   1219

gaaacaagaa ctctgtgtat tcctgtaccg agctgtgcat gtttttttct ttccatcgtg   1279

gagaatttaa gttattatcc gtttgctgca aggtttgccg tctcatttta tgcgttggga   1339

tgttggcaag aaagggcaga tgtcatgtga gaatttaagt taagtgaaat cgattcaggg   1399

ttttcttggt ttcagtttca acaaaaaaaa aaaaaaaggg cggccg                  1445


<210> SEQ ID NO 2
<211> LENGTH: 289
<212> TYPE: PRT
<213> ORGANISM: Zea mays

<400> SEQUENCE: 2

Met Glu Gly Lys Glu Glu Asp Val Arg Leu Gly Ala Asn Lys Phe Ser
 1               5                  10                  15

Glu Arg Gln Pro Ile Gly Thr Ala Ala Gln Gly Ala Ala Asp Asp Lys
            20                  25                  30

Asp Tyr Lys Glu Pro Pro Pro Ala Pro Leu Phe Glu Pro Gly Glu Leu
        35                  40                  45

Lys Ser Trp Ser Phe Tyr Arg Ala Gly Ile Ala Glu Phe Val Ala Thr
    50                  55                  60

Phe Leu Phe Leu Tyr Ile Thr Ile Leu Thr Val Met Gly Val Ser Lys
65                  70                  75                  80

Ser Thr Ser Lys Cys Ala Thr Val Gly Ile Gln Gly Ile Ala Trp Ser
                85                  90                  95

Phe Gly Gly Met Ile Phe Ala Leu Val Tyr Cys Thr Ala Gly Ile Ser
            100                 105                 110

Gly Gly His Ile Asn Pro Ala Val Thr Phe Gly Leu Phe Leu Ala Arg
        115                 120                 125

Lys Leu Ser Leu Thr Arg Ala Leu Phe Tyr Ile Ile Met Gln Cys Leu
    130                 135                 140

Gly Ala Ile Cys Gly Ala Gly Val Val Lys Gly Phe Gln Gln Gly Leu
145                 150                 155                 160

Tyr Met Gly Asn Gly Gly Gly Ala Asn Val Val Ala Pro Gly Tyr Thr
                165                 170                 175

Lys Gly Asp Gly Leu Gly Ala Glu Ile Val Gly Thr Phe Ile Leu Val
            180                 185                 190

Tyr Thr Val Phe Ser Ala Thr Asp Ala Lys Arg Asn Ala Arg Asp Ser
        195                 200                 205

His Val Pro Ile Leu Ala Pro Leu Pro Ile Gly Phe Ala Val Phe Leu
    210                 215                 220
```

```
Val His Leu Ala Thr Ile Pro Ile Thr Gly Thr Gly Ile Asn Pro Ala
225                 230                 235                 240

Arg Ser Leu Gly Ala Ala Ile Ile Tyr Asn Arg Asp His Ala Trp Asn
                245                 250                 255

Asp His Trp Ile Phe Trp Val Gly Pro Phe Ile Gly Ala Ala Leu Ala
            260                 265                 270

Ala Ile Tyr His Gln Val Ile Ile Arg Ala Ile Pro Phe Lys Ser Arg
        275                 280                 285

Ser


<210> SEQ ID NO 3
<211> LENGTH: 1204
<212> TYPE: DNA
<213> ORGANISM: Zea mays
<220> FEATURE:
<221> NAME/KEY: CDS
<222> LOCATION: (123)...(999)

<400> SEQUENCE: 3

cccgggtcga cccacgcgtc cggacacaca ccgctgcttc aagaaaccac cgagagccca     60

accgcacagg caggagagag agcagggagc cagggacagt agcgtggggc cggggagcaa    120

ag atg gag ggg aag gag gag gac gtg cgc ctg ggc gcc aac aag ttc       167
   Met Glu Gly Lys Glu Glu Asp Val Arg Leu Gly Ala Asn Lys Phe
    1               5                  10                  15

tcg gag cgg cag ccc atc ggc acg gcg gcg cag ggc gcc ggg gcc ggg      215
Ser Glu Arg Gln Pro Ile Gly Thr Ala Ala Gln Gly Ala Gly Ala Gly
                 20                  25                  30

gac gac gac aag gac tac aag gag ccc ccg ccg gcg ccg ctg ttc gag      263
Asp Asp Asp Lys Asp Tyr Lys Glu Pro Pro Pro Ala Pro Leu Phe Glu
             35                  40                  45

ccc ggg gag ctc aag tcc tgg tcc ttc tac cgc gcg ggc atc gcc gag      311
Pro Gly Glu Leu Lys Ser Trp Ser Phe Tyr Arg Ala Gly Ile Ala Glu
         50                  55                  60

ttc gtc gcc acc ttc ctc ttc ctc tac atc acc gtc ctc acc gtc atg      359
Phe Val Ala Thr Phe Leu Phe Leu Tyr Ile Thr Val Leu Thr Val Met
     65                  70                  75

ggc gtc tcc aag tcc acc tcc aag tgc gcc acc gtc ggc atc cag ggc      407
Gly Val Ser Lys Ser Thr Ser Lys Cys Ala Thr Val Gly Ile Gln Gly
 80                  85                  90                  95

atc gcc tgg tcc ttc gga ggg atg atc ttc gcg ctc gtc tac tgc acc      455
Ile Ala Trp Ser Phe Gly Gly Met Ile Phe Ala Leu Val Tyr Cys Thr
                100                 105                 110

gcc ggc atc tcc gga gga cac atc aac cca gct gtg acc ttc ggg ctg      503
Ala Gly Ile Ser Gly Gly His Ile Asn Pro Ala Val Thr Phe Gly Leu
            115                 120                 125

ttc ttg gcc agg aag ctg tcc ctg act agg gcc atc ttc tac att atc      551
Phe Leu Ala Arg Lys Leu Ser Leu Thr Arg Ala Ile Phe Tyr Ile Ile
        130                 135                 140

atg caa tgc ctg ggt gcc atc tgt gga gct gga gtg gtg aag ggc ttc      599
Met Gln Cys Leu Gly Ala Ile Cys Gly Ala Gly Val Val Lys Gly Phe
    145                 150                 155

cag cag ggg ctt tac atg ggc aac ggc ggt ggc gcc aat gtt gtc gcc      647
Gln Gln Gly Leu Tyr Met Gly Asn Gly Gly Gly Ala Asn Val Val Ala
160                 165                 170                 175

cct gga tac acc aag ggg gac ggc ctt ggc gca gag atc gtt ggc acc      695
Pro Gly Tyr Thr Lys Gly Asp Gly Leu Gly Ala Glu Ile Val Gly Thr
                180                 185                 190

ttc atc cta gtc tac acc gtc ttc tcg gcc acc gat gcc aag agg aac      743
```

-continued

```
Phe Ile Leu Val Tyr Thr Val Phe Ser Ala Thr Asp Ala Lys Arg Asn
            195                 200                 205

gcc agg gac tcc cat gtc ccc atc ctt gcc cca ctg cca att ggg ttc      791
Ala Arg Asp Ser His Val Pro Ile Leu Ala Pro Leu Pro Ile Gly Phe
        210                 215                 220

gcg gtg ttc ctg gtc cac ctt gcc acc atc ccc atc acc ggc acc ggc      839
Ala Val Phe Leu Val His Leu Ala Thr Ile Pro Ile Thr Gly Thr Gly
    225                 230                 235

atc aac ccg gct agg agc ctt ggc gcc gcc atc atc tac aac cgg gat      887
Ile Asn Pro Ala Arg Ser Leu Gly Ala Ala Ile Ile Tyr Asn Arg Asp
240                 245                 250                 255

cat gcg tgg agc gac cat tgg atc ttc tgg gtc ggc ccc ttc atc ggc      935
His Ala Trp Ser Asp His Trp Ile Phe Trp Val Gly Pro Phe Ile Gly
                260                 265                 270

gcc gcc ctg gct gcc atc tac cac cag gtg atc atc agg gcc atc ccg      983
Ala Ala Leu Ala Ala Ile Tyr His Gln Val Ile Ile Arg Ala Ile Pro
            275                 280                 285

ttc aag agc agg tct t aagctgccgc gggtgtgctg agacatgtgg ggaatgtatt   1039
Phe Lys Ser Arg Ser
        290

gtctgcccac gcctagtttc tctgctgaat cttccatctc tcttcccttc aagactgctc   1099

actgctgcac tgctctgtta tctgaaccca gaacttcgtg tactcctgta ccgagctgtg   1159

tgtatgtttt tttttcaaaa aaaaaaaaaa aaaaaagggc ggccg                    1204


<210> SEQ ID NO 4
<211> LENGTH: 292
<212> TYPE: PRT
<213> ORGANISM: Zea mays

<400> SEQUENCE: 4

Met Glu Gly Lys Glu Glu Asp Val Arg Leu Gly Ala Asn Lys Phe Ser
 1               5                  10                  15

Glu Arg Gln Pro Ile Gly Thr Ala Ala Gln Gly Ala Gly Ala Gly Asp
            20                  25                  30

Asp Asp Lys Asp Tyr Lys Glu Pro Pro Pro Ala Pro Leu Phe Glu Pro
        35                  40                  45

Gly Glu Leu Lys Ser Trp Ser Phe Tyr Arg Ala Gly Ile Ala Glu Phe
    50                  55                  60

Val Ala Thr Phe Leu Phe Leu Tyr Ile Thr Val Leu Thr Val Met Gly
65                  70                  75                  80

Val Ser Lys Ser Thr Ser Lys Cys Ala Thr Val Gly Ile Gln Gly Ile
                85                  90                  95

Ala Trp Ser Phe Gly Gly Met Ile Phe Ala Leu Val Tyr Cys Thr Ala
            100                 105                 110

Gly Ile Ser Gly Gly His Ile Asn Pro Ala Val Thr Phe Gly Leu Phe
        115                 120                 125

Leu Ala Arg Lys Leu Ser Leu Thr Arg Ala Ile Phe Tyr Ile Ile Met
    130                 135                 140

Gln Cys Leu Gly Ala Ile Cys Gly Ala Gly Val Val Lys Gly Phe Gln
145                 150                 155                 160

Gln Gly Leu Tyr Met Gly Asn Gly Gly Gly Ala Asn Val Val Ala Pro
                165                 170                 175

Gly Tyr Thr Lys Gly Asp Gly Leu Gly Ala Glu Ile Val Gly Thr Phe
            180                 185                 190

Ile Leu Val Tyr Thr Val Phe Ser Ala Thr Asp Ala Lys Arg Asn Ala
        195                 200                 205
```

-continued

```
Arg Asp Ser His Val Pro Ile Leu Ala Pro Leu Pro Ile Gly Phe Ala
    210                 215                 220

Val Phe Leu Val His Leu Ala Thr Ile Pro Ile Thr Gly Thr Gly Ile
225                 230                 235                 240

Asn Pro Ala Arg Ser Leu Gly Ala Ala Ile Ile Tyr Asn Arg Asp His
                245                 250                 255

Ala Trp Ser Asp His Trp Ile Phe Trp Val Gly Pro Phe Ile Gly Ala
            260                 265                 270

Ala Leu Ala Ala Ile Tyr His Gln Val Ile Ile Arg Ala Ile Pro Phe
        275                 280                 285

Lys Ser Arg Ser
    290


<210> SEQ ID NO 5
<211> LENGTH: 702
<212> TYPE: DNA
<213> ORGANISM: Zea mays
<220> FEATURE:
<221> NAME/KEY: CDS
<222> LOCATION: (326)...(702)

<400> SEQUENCE: 5

cccgggtcga cccacgcgtc cgcaagaaac caccgccgag cccaaccgca caagcgcgcg      60

aggcaggaga gagagagaga gagaggcggg gagcaaaaca atggagggga aagaggagga     120

cgtgcgcctg ggcgccaaca agttctcgga gcgccagccc atcgggacgg cggcgcaggg     180

cgccgctgac gacaaggact acaaggagcc cccgccggcg ccgctgttcg agcccgggga     240

gctcaagtcc tggtccttct accgcgcggg catcgccgag ttcgtcgcca ccttcctctt     300

cctctacatc accatcctca ccgtc atg ggc gtc tcc aag tcc acc tcc aag      352
                            Met Gly Val Ser Lys Ser Thr Ser Lys
                             1               5

tgc gcc acc gtc ggc atc cag ggc atc gcc tgg tcc ttc gga gga atg      400
Cys Ala Thr Val Gly Ile Gln Gly Ile Ala Trp Ser Phe Gly Gly Met
 10                  15                  20                  25

atc ttc gcg ctc gtc tac tgc acc gcc ggc atc tcc gga gga cac atc      448
Ile Phe Ala Leu Val Tyr Cys Thr Ala Gly Ile Ser Gly Gly His Ile
                 30                  35                  40

aac cca gct gtg act ttc ggg ctg ttc tta gcc agg aag ctg tcc ctg      496
Asn Pro Ala Val Thr Phe Gly Leu Phe Leu Ala Arg Lys Leu Ser Leu
             45                  50                  55

act agg gcc ctc ttc tac att atc atg caa tgc ctg ggt gcc atc tgt      544
Thr Arg Ala Leu Phe Tyr Ile Ile Met Gln Cys Leu Gly Ala Ile Cys
         60                  65                  70

gga gct gga gtg gtg aag ggc ttc cag cag gga ctt tac atg ggc aac      592
Gly Ala Gly Val Val Lys Gly Phe Gln Gln Gly Leu Tyr Met Gly Asn
     75                  80                  85

ggt ggt ggc gcc aat gtt gtc gca cct ggc tac acc aag ggt gat ggc      640
Gly Gly Gly Ala Asn Val Val Ala Pro Gly Tyr Thr Lys Gly Asp Gly
 90                  95                 100                 105

ctt ggc gct gag att gtt ggc acc ttc atc cta gtc tac acc gtc ttc      688
Leu Gly Ala Glu Ile Val Gly Thr Phe Ile Leu Val Tyr Thr Val Phe
                110                 115                 120

tcg gca acg atg ca                                                   702
Ser Ala Thr Met
            125


<210> SEQ ID NO 6
<211> LENGTH: 125
```

```
<212> TYPE: PRT
<213> ORGANISM: Zea mays

<400> SEQUENCE: 6

Met Gly Val Ser Lys Ser Thr Ser Lys Cys Ala Thr Val Gly Ile Gln
 1               5                  10                  15

Gly Ile Ala Trp Ser Phe Gly Gly Met Ile Phe Ala Leu Val Tyr Cys
            20                  25                  30

Thr Ala Gly Ile Ser Gly Gly His Ile Asn Pro Ala Val Thr Phe Gly
        35                  40                  45

Leu Phe Leu Ala Arg Lys Leu Ser Leu Thr Arg Ala Leu Phe Tyr Ile
    50                  55                  60

Ile Met Gln Cys Leu Gly Ala Ile Cys Gly Ala Gly Val Val Lys Gly
65                  70                  75                  80

Phe Gln Gln Gly Leu Tyr Met Gly Asn Gly Gly Gly Ala Asn Val Val
                85                  90                  95

Ala Pro Gly Tyr Thr Lys Gly Asp Gly Leu Gly Ala Glu Ile Val Gly
            100                 105                 110

Thr Phe Ile Leu Val Tyr Thr Val Phe Ser Ala Thr Met
        115                 120                 125


<210> SEQ ID NO 7
<211> LENGTH: 1069
<212> TYPE: DNA
<213> ORGANISM: Zea mays
<220> FEATURE:
<221> NAME/KEY: CDS
<222> LOCATION: (100)...(946)

<400> SEQUENCE: 7

cccgggtcga cccacgcgtc cgatcatccc ctttgcaagt atagtctctc tgctaagcga      60

agcgaagctt caagctagtc tcggcggctc tagaagacg atg ggc aag gac gac       114
                                           Met Gly Lys Asp Asp
                                            1               5

gtg atc gag agc ggc gct ggc ggc ggc gag ttc gct gcc aag gac tac      162
Val Ile Glu Ser Gly Ala Gly Gly Gly Glu Phe Ala Ala Lys Asp Tyr
                10                  15                  20

acg gac cct ccc ccg gcg ccg ctg atc gac gcg gcg gag ctg ggg tcc      210
Thr Asp Pro Pro Pro Ala Pro Leu Ile Asp Ala Ala Glu Leu Gly Ser
            25                  30                  35

tgg tcg ctg tac cgc gcc gtg atc gcc gag ttc atc gcc acg ctg ctg      258
Trp Ser Leu Tyr Arg Ala Val Ile Ala Glu Phe Ile Ala Thr Leu Leu
        40                  45                  50

ttc ctg tac atc acg gtg gcc acc gtg atc ggg tac aag cac cag acg      306
Phe Leu Tyr Ile Thr Val Ala Thr Val Ile Gly Tyr Lys His Gln Thr
     55                  60                  65

gac gcg tcg gcg tcg ggc gcc gac gcg gcg tgc ggc ggc gtg ggc gtg      354
Asp Ala Ser Ala Ser Gly Ala Asp Ala Ala Cys Gly Gly Val Gly Val
 70                  75                  80                  85

ctg ggc atc gcc tgg gcc ttc ggc ggc atg atc ttc gtc ctc gtc tac      402
Leu Gly Ile Ala Trp Ala Phe Gly Gly Met Ile Phe Val Leu Val Tyr
                90                  95                  100

tgc acc gcc ggc atc tcg ggg ggc cac atc aac ccc gcc gtc acc ttc      450
Cys Thr Ala Gly Ile Ser Gly Gly His Ile Asn Pro Ala Val Thr Phe
            105                 110                 115

ggc ctc ttc ctg gcg cgc aag gtc tcc ctg gtg cgc gcg ctg ctc tac      498
Gly Leu Phe Leu Ala Arg Lys Val Ser Leu Val Arg Ala Leu Leu Tyr
        120                 125                 130

atc gtg gcg cag tgc ctc ggc gcc atc tgc ggc gtc ggc ctc gtc aag      546
```

-continued

```
Ile Val Ala Gln Cys Leu Gly Ala Ile Cys Gly Val Gly Leu Val Lys
    135                 140                 145

gcg ttc cag agc gcc tac ttc gac agg tac ggc ggc ggc gcc aac tcg      594
Ala Phe Gln Ser Ala Tyr Phe Asp Arg Tyr Gly Gly Gly Ala Asn Ser
150                 155                 160                 165

ctc gcc tcc ggc tac tcc cgc ggc acc ggc ctc ggc gcc gag atc atc      642
Leu Ala Ser Gly Tyr Ser Arg Gly Thr Gly Leu Gly Ala Glu Ile Ile
                170                 175                 180

ggc acc ttc gtg ctc gtc tac acc gtc ttc tcc gcc acc gac ccc aag      690
Gly Thr Phe Val Leu Val Tyr Thr Val Phe Ser Ala Thr Asp Pro Lys
            185                 190                 195

cgc aac gcc cgc gac tcc cac gtc ccg gtt ctg gct cct tca gga gca      738
Arg Asn Ala Arg Asp Ser His Val Pro Val Leu Ala Pro Ser Gly Ala
        200                 205                 210

acg cgt gat gag cgg ggc ttg gct gtg gag caa tgg cgg gcg acc tac      786
Thr Arg Asp Glu Arg Gly Leu Ala Val Glu Gln Trp Arg Ala Thr Tyr
    215                 220                 225

ggg cgg ggg gcc gtg agc gag gag aat gcc atc att cat cga tcg act      834
Gly Arg Gly Ala Val Ser Glu Glu Asn Ala Ile Ile His Arg Ser Thr
230                 235                 240                 245

tgg gtg ccg gtg gtt ggt tcg ggt cgc ctt ttt ttt gtt tca gca gct      882
Trp Val Pro Val Val Gly Ser Gly Arg Leu Phe Phe Val Ser Ala Ala
                250                 255                 260

gct gcg ttg cgc gcg tgc gtg aga ttt ggt ttg gtt tcg ttc ccc tgc      930
Ala Ala Leu Arg Ala Cys Val Arg Phe Gly Leu Val Ser Phe Pro Cys
            265                 270                 275

aat gta atc atg tcg t gactctcaag ggattattcc gctctgctct taaaaaaaaa    986
Asn Val Ile Met Ser
        280

aaaaaaaaaa aaaaaaaaaa aaaaaaaaaa aaaaaaaaaa aaaaaaaaaa aaaaaaaaaa   1046

aaaaaaaaaa aaaagggcgg ccg                                           1069


<210> SEQ ID NO 8
<211> LENGTH: 282
<212> TYPE: PRT
<213> ORGANISM: Zea mays

<400> SEQUENCE: 8

Met Gly Lys Asp Asp Val Ile Glu Ser Gly Ala Gly Gly Gly Glu Phe
 1               5                  10                  15

Ala Ala Lys Asp Tyr Thr Asp Pro Pro Pro Ala Pro Leu Ile Asp Ala
            20                  25                  30

Ala Glu Leu Gly Ser Trp Ser Leu Tyr Arg Ala Val Ile Ala Glu Phe
        35                  40                  45

Ile Ala Thr Leu Leu Phe Leu Tyr Ile Thr Val Ala Thr Val Ile Gly
    50                  55                  60

Tyr Lys His Gln Thr Asp Ala Ser Ala Ser Gly Ala Asp Ala Ala Cys
65                  70                  75                  80

Gly Gly Val Gly Val Leu Gly Ile Ala Trp Ala Phe Gly Gly Met Ile
                85                  90                  95

Phe Val Leu Val Tyr Cys Thr Ala Gly Ile Ser Gly Gly His Ile Asn
            100                 105                 110

Pro Ala Val Thr Phe Gly Leu Phe Leu Ala Arg Lys Val Ser Leu Val
        115                 120                 125

Arg Ala Leu Leu Tyr Ile Val Ala Gln Cys Leu Gly Ala Ile Cys Gly
    130                 135                 140

Val Gly Leu Val Lys Ala Phe Gln Ser Ala Tyr Phe Asp Arg Tyr Gly
```

-continued

```
145                 150                 155                 160

Gly Gly Ala Asn Ser Leu Ala Ser Gly Tyr Ser Arg Gly Thr Gly Leu
                165                 170                 175

Gly Ala Glu Ile Ile Gly Thr Phe Val Leu Val Tyr Thr Val Phe Ser
            180                 185                 190

Ala Thr Asp Pro Lys Arg Asn Ala Arg Asp Ser His Val Pro Val Leu
        195                 200                 205

Ala Pro Ser Gly Ala Thr Arg Asp Glu Arg Gly Leu Ala Val Glu Gln
    210                 215                 220

Trp Arg Ala Thr Tyr Gly Arg Gly Ala Val Ser Glu Glu Asn Ala Ile
225                 230                 235                 240

Ile His Arg Ser Thr Trp Val Pro Val Val Gly Ser Gly Arg Leu Phe
                245                 250                 255

Phe Val Ser Ala Ala Ala Ala Leu Arg Ala Cys Val Arg Phe Gly Leu
            260                 265                 270

Val Ser Phe Pro Cys Asn Val Ile Met Ser
        275                 280


<210> SEQ ID NO 9
<211> LENGTH: 1333
<212> TYPE: DNA
<213> ORGANISM: Zea mays
<220> FEATURE:
<221> NAME/KEY: CDS
<222> LOCATION: (142)...(1018)

<400> SEQUENCE: 9

cccgggtcga cccacgcgtc cgatccattc ggccattcct taacatcctt gttgcaagcg     60

gcgccagctt gctcgcgctc tctcgcagct gctacgctaa agcaagtcta gtctctagag    120

gaggaggcgg agggggaggc c atg ggc aag gac gac gtg gtc cag agc ggc      171
                        Met Gly Lys Asp Asp Val Val Gln Ser Gly
                         1               5                  10

gcg ggc ggc ggg gag ttc gcc gcc aag gac tac acg gac ccg ccg ccg      219
Ala Gly Gly Gly Glu Phe Ala Ala Lys Asp Tyr Thr Asp Pro Pro Pro
                15                  20                  25

gcg ccg ctg gtg gac gcg gcg gag ctg ggt tcg tgg tcg ctg tac cgc      267
Ala Pro Leu Val Asp Ala Ala Glu Leu Gly Ser Trp Ser Leu Tyr Arg
            30                  35                  40

gcg gtg atc gcg gag ttc atc gcg acg ctg ctg ttc ctg tac gtg acg      315
Ala Val Ile Ala Glu Phe Ile Ala Thr Leu Leu Phe Leu Tyr Val Thr
        45                  50                  55

gtg gcg acg gtg atc ggg tac aag cac cag acg gac gcg tct gcg tcg      363
Val Ala Thr Val Ile Gly Tyr Lys His Gln Thr Asp Ala Ser Ala Ser
     60                  65                  70

ggg gcc ggg gcg gac gcg gcg tgc ggc ggc gtg ggc gtg ctg ggc atc      411
Gly Ala Gly Ala Asp Ala Ala Cys Gly Gly Val Gly Val Leu Gly Ile
 75                  80                  85                  90

gcg tgg gcc ttc ggc ggc atg atc ttc gtg ctg gtc tac tgc acc gcc      459
Ala Trp Ala Phe Gly Gly Met Ile Phe Val Leu Val Tyr Cys Thr Ala
                95                 100                 105

ggc atc tcg ggg ggc cac atc aac ccg gcc gtc acc ttc ggc ctc ttc      507
Gly Ile Ser Gly Gly His Ile Asn Pro Ala Val Thr Phe Gly Leu Phe
            110                 115                 120

ctg gcg cgc aag gtg tcg ctg gtg cgc gcg ctg ctg tac atg gtg gcg      555
Leu Ala Arg Lys Val Ser Leu Val Arg Ala Leu Leu Tyr Met Val Ala
        125                 130                 135

cag tgc ctc ggc gcc gtc tgc ggc gtc ggc ctc gtc aag gcg ttc cag      603
Gln Cys Leu Gly Ala Val Cys Gly Val Gly Leu Val Lys Ala Phe Gln
```

```
    140                 145                 150

agc gcc tac ttc gac cgg tac ggc ggc ggc gcc aac tcg ctc gcg tcc      651
Ser Ala Tyr Phe Asp Arg Tyr Gly Gly Gly Ala Asn Ser Leu Ala Ser
155                 160                 165                 170

ggc tac tcc cgc ggc gcg ggg ctc ggc gcc gag atc gtc ggc acc ttc      699
Gly Tyr Ser Arg Gly Ala Gly Leu Gly Ala Glu Ile Val Gly Thr Phe
                175                 180                 185

gtg ctc gtg tac acc gtc ttc tcc gcc acc gac ccc aag cgc aac gcc      747
Val Leu Val Tyr Thr Val Phe Ser Ala Thr Asp Pro Lys Arg Asn Ala
            190                 195                 200

cgc gac tcc cac gtc ccg gtt ctg gct ccc ctc ccc atc ggc ttc gcc      795
Arg Asp Ser His Val Pro Val Leu Ala Pro Leu Pro Ile Gly Phe Ala
        205                 210                 215

gtg ttc atg gtc cac ctg gcc acc atc ccc gtc acc ggc acc ggc atc      843
Val Phe Met Val His Leu Ala Thr Ile Pro Val Thr Gly Thr Gly Ile
    220                 225                 230

aac ccg gcc agg agc ctg ggc gcc gcc gtc gtc tac aac aag gac aag      891
Asn Pro Ala Arg Ser Leu Gly Ala Ala Val Val Tyr Asn Lys Asp Lys
235                 240                 245                 250

cca tgg gat gac cac tgg att ttc tgg gtg ggc ccg ctc ctg ggc gct      939
Pro Trp Asp Asp His Trp Ile Phe Trp Val Gly Pro Leu Leu Gly Ala
                255                 260                 265

gcc atc gcg gcc ttc tac cac cag tac atc ctc cgg gcg ggc gcc atc      987
Ala Ile Ala Ala Phe Tyr His Gln Tyr Ile Leu Arg Ala Gly Ala Ile
            270                 275                 280

aag gct ctc ggc tcc ttc agg agc aac gcg t gatgagcaga gctaaagaaa     1038
Lys Ala Leu Gly Ser Phe Arg Ser Asn Ala
        285                 290

ggccttcgct ggactgcgtg ctggagcaac ggcgatcgat cgatctagcg tggggagagg   1098

cggataggcg ggcgcgcgag ggaggagaat aagtttgtgc cggtggcccg gtctcgtcgg   1158

tcgcttttgt tccagcatgc agctgcgtcg cgttcgtgtg cgtgcgtggg ggtctcctta   1218

atttccccgg cccctgtaat catcaatcac catgtgtgcg tataatatct gctgccaagg   1278

gatcgattat tccccccaaa aaaaaaaaaa aaaaaaaaaa aaaaaagggc ggccg        1333


<210> SEQ ID NO 10
<211> LENGTH: 292
<212> TYPE: PRT
<213> ORGANISM: Zea mays

<400> SEQUENCE: 10

Met Gly Lys Asp Asp Val Val Gln Ser Gly Ala Gly Gly Gly Glu Phe
 1               5                  10                  15

Ala Ala Lys Asp Tyr Thr Asp Pro Pro Pro Ala Pro Leu Val Asp Ala
            20                  25                  30

Ala Glu Leu Gly Ser Trp Ser Leu Tyr Arg Ala Val Ile Ala Glu Phe
        35                  40                  45

Ile Ala Thr Leu Leu Phe Leu Tyr Val Thr Val Ala Thr Val Ile Gly
    50                  55                  60

Tyr Lys His Gln Thr Asp Ala Ser Ala Ser Gly Ala Gly Ala Asp Ala
65                  70                  75                  80

Ala Cys Gly Gly Val Gly Val Leu Gly Ile Ala Trp Ala Phe Gly Gly
                85                  90                  95

Met Ile Phe Val Leu Val Tyr Cys Thr Ala Gly Ile Ser Gly Gly His
            100                 105                 110

Ile Asn Pro Ala Val Thr Phe Gly Leu Phe Leu Ala Arg Lys Val Ser
        115                 120                 125
```

```
Leu Val Arg Ala Leu Leu Tyr Met Val Ala Gln Cys Leu Gly Ala Val
    130                 135                 140

Cys Gly Val Gly Leu Val Lys Ala Phe Gln Ser Ala Tyr Phe Asp Arg
145                 150                 155                 160

Tyr Gly Gly Gly Ala Asn Ser Leu Ala Ser Gly Tyr Ser Arg Gly Ala
                165                 170                 175

Gly Leu Gly Ala Glu Ile Val Gly Thr Phe Val Leu Val Tyr Thr Val
            180                 185                 190

Phe Ser Ala Thr Asp Pro Lys Arg Asn Ala Arg Asp Ser His Val Pro
        195                 200                 205

Val Leu Ala Pro Leu Pro Ile Gly Phe Ala Val Phe Met Val His Leu
    210                 215                 220

Ala Thr Ile Pro Val Thr Gly Thr Gly Ile Asn Pro Ala Arg Ser Leu
225                 230                 235                 240

Gly Ala Ala Val Val Tyr Asn Lys Asp Lys Pro Trp Asp Asp His Trp
                245                 250                 255

Ile Phe Trp Val Gly Pro Leu Leu Gly Ala Ala Ile Ala Ala Phe Tyr
            260                 265                 270

His Gln Tyr Ile Leu Arg Ala Gly Ala Ile Lys Ala Leu Gly Ser Phe
        275                 280                 285

Arg Ser Asn Ala
    290


<210> SEQ ID NO 11
<211> LENGTH: 1217
<212> TYPE: DNA
<213> ORGANISM: Zea mays
<220> FEATURE:
<221> NAME/KEY: CDS
<222> LOCATION: (110)...(974)

<400> SEQUENCE: 11

cccgggtcga cccacgcgtc cgcacaccgc aaccgcaagc aagcgaagcg cagagcctgc      60

ctgaccagag ctagctgagc tacagccaac agcagctggt ctgactgac atg gcg aag     118
                                                      Met Ala Lys
                                                       1

gac atc gag gca tcg ggg ccc gag gcg ggc gag ttc tcg gcc aag gac       166
Asp Ile Glu Ala Ser Gly Pro Glu Ala Gly Glu Phe Ser Ala Lys Asp
     5                  10                  15

tac acc gac cct ccg ccg gcg ccg ctg atc gac gcg gag gag ctc acc       214
Tyr Thr Asp Pro Pro Pro Ala Pro Leu Ile Asp Ala Glu Glu Leu Thr
 20                  25                  30                  35

cag tgg tca ctg tac cgc gcg gtc atc gcc gag ttc atc gcc acg ctg       262
Gln Trp Ser Leu Tyr Arg Ala Val Ile Ala Glu Phe Ile Ala Thr Leu
                 40                  45                  50

ctc ttc ctc tac atc acc gtg gcc acc gtg atc ggg tac aag cac cag       310
Leu Phe Leu Tyr Ile Thr Val Ala Thr Val Ile Gly Tyr Lys His Gln
             55                  60                  65

acg gac gcg tcg gcg tcg ggc ccc gac gcg gcg tgc ggc ggc gtc ggc       358
Thr Asp Ala Ser Ala Ser Gly Pro Asp Ala Ala Cys Gly Gly Val Gly
         70                  75                  80

atc ctc ggc atc gct tgg gcc ttc ggc ggc atg atc ttc atc ctc gtc       406
Ile Leu Gly Ile Ala Trp Ala Phe Gly Gly Met Ile Phe Ile Leu Val
     85                  90                  95

tac tgc acc gcc ggc atc tca ggt ggg cac atc aac ccg gcc gtg acc       454
Tyr Cys Thr Ala Gly Ile Ser Gly Gly His Ile Asn Pro Ala Val Thr
100                 105                 110                 115
```

-continued

```
ttc ggc ctg ttc ctg gcc agg aag gtg tcc ctc gtc cgc gcg ctg ctc      502
Phe Gly Leu Phe Leu Ala Arg Lys Val Ser Leu Val Arg Ala Leu Leu
                120                 125                 130

tac atc atc gcg cag tgc ctg ggc gcc atc tgc ggc gtg ggc ctc gtc      550
Tyr Ile Ile Ala Gln Cys Leu Gly Ala Ile Cys Gly Val Gly Leu Val
            135                 140                 145

aag ggc ttc cag agc gcc tac tac gtg cgc tac ggc ggc ggc gcc aac      598
Lys Gly Phe Gln Ser Ala Tyr Tyr Val Arg Tyr Gly Gly Gly Ala Asn
        150                 155                 160

gag ctc agc gac ggc tac tcc aag ggc acc ggc ctc gcc gcc gag atc      646
Glu Leu Ser Asp Gly Tyr Ser Lys Gly Thr Gly Leu Ala Ala Glu Ile
    165                 170                 175

atc ggc acg ttc gtg ctc gtc tac acc gtc ttc tcc gcc acc gac ccc      694
Ile Gly Thr Phe Val Leu Val Tyr Thr Val Phe Ser Ala Thr Asp Pro
180                 185                 190                 195

aag cgc agt gcc cgt gac tcc cac gtt ccg gtg cta gct cct ctc cca      742
Lys Arg Ser Ala Arg Asp Ser His Val Pro Val Leu Ala Pro Leu Pro
                200                 205                 210

att ggg ttc gcc gtg ttc atg gtg cac ctg gcc acc atc ccc atc acc      790
Ile Gly Phe Ala Val Phe Met Val His Leu Ala Thr Ile Pro Ile Thr
            215                 220                 225

ggc acc ggc atc aac ccg gcg agg agc ctg gga gcc gcg gtc atc tac      838
Gly Thr Gly Ile Asn Pro Ala Arg Ser Leu Gly Ala Ala Val Ile Tyr
        230                 235                 240

aac aag gac aag gcc tgg gac gac caa tgg atc ttc tgg gtg ggc cca      886
Asn Lys Asp Lys Ala Trp Asp Asp Gln Trp Ile Phe Trp Val Gly Pro
    245                 250                 255

ctg att ggc gcc gcc atc gcc gcc gcc tac cac cag tac gtg ctg agg      934
Leu Ile Gly Ala Ala Ile Ala Ala Ala Tyr His Gln Tyr Val Leu Arg
260                 265                 270                 275

gcc agc gcc acc aag ctc ggg tcc tac cgg agc aac gcc t aagttccgcc     984
Ala Ser Ala Thr Lys Leu Gly Ser Tyr Arg Ser Asn Ala
                280                 285

cggacgcgcc aggagctggg caccgttccg attctgttcc tccacatgac gccctgttct   1044

gtttccgtgt ggccaggact ccgctcgctc gctgctgttt tctacttcgg accaaagtgt   1104

gacatatctt tgctttctgt atatgtatgt aggaatgcat catgtaagga gaatttggaa   1164

tacaattgcg tgagttttta tccgatcaca aaaaaaaaaa aaaagggcgg ccg          1217


<210> SEQ ID NO 12
<211> LENGTH: 288
<212> TYPE: PRT
<213> ORGANISM: Zea mays

<400> SEQUENCE: 12

Met Ala Lys Asp Ile Glu Ala Ser Gly Pro Glu Ala Gly Glu Phe Ser
 1               5                  10                  15

Ala Lys Asp Tyr Thr Asp Pro Pro Pro Ala Pro Leu Ile Asp Ala Glu
            20                  25                  30

Glu Leu Thr Gln Trp Ser Leu Tyr Arg Ala Val Ile Ala Glu Phe Ile
        35                  40                  45

Ala Thr Leu Leu Phe Leu Tyr Ile Thr Val Ala Thr Val Ile Gly Tyr
    50                  55                  60

Lys His Gln Thr Asp Ala Ser Ala Ser Gly Pro Asp Ala Ala Cys Gly
65                  70                  75                  80

Gly Val Gly Ile Leu Gly Ile Ala Trp Ala Phe Gly Gly Met Ile Phe
                85                  90                  95

Ile Leu Val Tyr Cys Thr Ala Gly Ile Ser Gly Gly His Ile Asn Pro
```

```
            100                 105                 110

Ala Val Thr Phe Gly Leu Phe Leu Ala Arg Lys Val Ser Leu Val Arg
        115                 120                 125

Ala Leu Leu Tyr Ile Ile Ala Gln Cys Leu Gly Ala Ile Cys Gly Val
    130                 135                 140

Gly Leu Val Lys Gly Phe Gln Ser Ala Tyr Tyr Val Arg Tyr Gly Gly
145                 150                 155                 160

Gly Ala Asn Glu Leu Ser Asp Gly Tyr Ser Lys Gly Thr Gly Leu Ala
                165                 170                 175

Ala Glu Ile Ile Gly Thr Phe Val Leu Val Tyr Thr Val Phe Ser Ala
            180                 185                 190

Thr Asp Pro Lys Arg Ser Ala Arg Asp Ser His Val Pro Val Leu Ala
        195                 200                 205

Pro Leu Pro Ile Gly Phe Ala Val Phe Met Val His Leu Ala Thr Ile
    210                 215                 220

Pro Ile Thr Gly Thr Gly Ile Asn Pro Ala Arg Ser Leu Gly Ala Ala
225                 230                 235                 240

Val Ile Tyr Asn Lys Asp Lys Ala Trp Asp Asp Gln Trp Ile Phe Trp
                245                 250                 255

Val Gly Pro Leu Ile Gly Ala Ala Ile Ala Ala Ala Tyr His Gln Tyr
            260                 265                 270

Val Leu Arg Ala Ser Ala Thr Lys Leu Gly Ser Tyr Arg Ser Asn Ala
        275                 280                 285
```

<210> SEQ ID NO 13
<211> LENGTH: 1206
<212> TYPE: DNA
<213> ORGANISM: Zea mays
<220> FEATURE:
<221> NAME/KEY: CDS
<222> LOCATION: (97)...(964)

<400> SEQUENCE: 13

```
cccgggtcga cccacgcgtc cgagcaaagc gaagcgcgcg cacagagatc tagctgagct     60

actagctata gcagcagctg ctgcaggtct cctgac atg gcg aag cag gac atc      114
                                        Met Ala Lys Gln Asp Ile
                                          1               5

gaa gca tcg ggg ccc gag gcc ggc gag ttc tcg gcc aag gac tac acg      162
Glu Ala Ser Gly Pro Glu Ala Gly Glu Phe Ser Ala Lys Asp Tyr Thr
             10                  15                  20

gac cct ccg ccg gcg ccg ctc atc gac gcg gat gag ctc acc aag tgg      210
Asp Pro Pro Pro Ala Pro Leu Ile Asp Ala Asp Glu Leu Thr Lys Trp
         25                  30                  35

tcc ctc tac cgc gcg gtc atc gcc gag ttc atc gcc acg ctg ctc ttc      258
Ser Leu Tyr Arg Ala Val Ile Ala Glu Phe Ile Ala Thr Leu Leu Phe
     40                  45                  50

ctc tac atc acc gtg gcc acc gtc atc ggg tac aag cac cag acg gac      306
Leu Tyr Ile Thr Val Ala Thr Val Ile Gly Tyr Lys His Gln Thr Asp
 55                  60                  65                  70

gcg gcg gcg tcg ggc ccc gac gcg gcg tgc ggc ggc gtg ggc atc ctc      354
Ala Ala Ala Ser Gly Pro Asp Ala Ala Cys Gly Gly Val Gly Ile Leu
                 75                  80                  85

ggc atc gcg tgg gcc ttc ggc ggc atg atc ttc atc ctc gtc tac tgc      402
Gly Ile Ala Trp Ala Phe Gly Gly Met Ile Phe Ile Leu Val Tyr Cys
             90                  95                 100

acc gcc ggc atc tca ggt ggg cac atc aac ccg gcc gtg acc ttc ggc      450
Thr Ala Gly Ile Ser Gly Gly His Ile Asn Pro Ala Val Thr Phe Gly
        105                 110                 115
```

```
ctg ttc ctg gcg agg aag gtg tcc ctc gtc cgc gcc ctg ctc tac atc      498
Leu Phe Leu Ala Arg Lys Val Ser Leu Val Arg Ala Leu Leu Tyr Ile
    120                 125                 130

atc gcg cag tgc ctg ggc gcc atc tgc ggc gtc ggc ctc gtc aag ggc      546
Ile Ala Gln Cys Leu Gly Ala Ile Cys Gly Val Gly Leu Val Lys Gly
135                 140                 145                 150

ttc cag agc gcc tac tac gtg cgc tac ggc ggc ggc gcc aac gag ctc      594
Phe Gln Ser Ala Tyr Tyr Val Arg Tyr Gly Gly Gly Ala Asn Glu Leu
                155                 160                 165

agc gac ggc tac tcc aag ggc acc ggc ctc gcc gcc gag atc atc ggc      642
Ser Asp Gly Tyr Ser Lys Gly Thr Gly Leu Ala Ala Glu Ile Ile Gly
            170                 175                 180

acc ttc gtg ctc gtc tac acc gtc ttc tcc gcc acc gac ccc aag cgc      690
Thr Phe Val Leu Val Tyr Thr Val Phe Ser Ala Thr Asp Pro Lys Arg
        185                 190                 195

agt gcc cgt gac tcc cac gtc ccg gtg ttg gcc cct ctt ccg att ggg      738
Ser Ala Arg Asp Ser His Val Pro Val Leu Ala Pro Leu Pro Ile Gly
    200                 205                 210

ttc gcc gtg ttc atg gtg cac ctg gcc acc atc ccc atc acc ggc acc      786
Phe Ala Val Phe Met Val His Leu Ala Thr Ile Pro Ile Thr Gly Thr
215                 220                 225                 230

ggc atc aac ccg gcg agg agc ttg gga gcc gcg gtc atc tac aac aag      834
Gly Ile Asn Pro Ala Arg Ser Leu Gly Ala Ala Val Ile Tyr Asn Lys
                235                 240                 245

gac aag gcc tgg gac gac caa tgg atc ttc tgg gtg ggc cca ctg atc      882
Asp Lys Ala Trp Asp Asp Gln Trp Ile Phe Trp Val Gly Pro Leu Ile
            250                 255                 260

ggc gcc gcc atc gcc gcc gcc tac cac cag tac gtg ctg aga gcc agc      930
Gly Ala Ala Ile Ala Ala Ala Tyr His Gln Tyr Val Leu Arg Ala Ser
        265                 270                 275

gcc acc aag ctc ggg tcc tac cgg agc aac gcc t aataagtccg             974
Ala Thr Lys Leu Gly Ser Tyr Arg Ser Asn Ala
    280                 285

gcggcgggag ctgtgggcgc caccgatcga tccaagtgta gatacgtacg ctcccccgac   1034

tccgtccagt atatgacgcc ctgtggtcgt ccacatctgc caccacagtc ccgtccgctt   1094

ggtgctgttt tctttctttc cttgacgggg aaaaaaagtg tgatatatct ttgctttctg   1154

tatatgtgac aaaatgcatt ctgtaaaaaa aaaaaaaaaa aaagggcggc cg           1206


<210> SEQ ID NO 14
<211> LENGTH: 289
<212> TYPE: PRT
<213> ORGANISM: Zea mays

<400> SEQUENCE: 14

Met Ala Lys Gln Asp Ile Glu Ala Ser Gly Pro Glu Ala Gly Glu Phe
 1               5                  10                  15

Ser Ala Lys Asp Tyr Thr Asp Pro Pro Pro Ala Pro Leu Ile Asp Ala
            20                  25                  30

Asp Glu Leu Thr Lys Trp Ser Leu Tyr Arg Ala Val Ile Ala Glu Phe
        35                  40                  45

Ile Ala Thr Leu Leu Phe Leu Tyr Ile Thr Val Ala Thr Val Ile Gly
    50                  55                  60

Tyr Lys His Gln Thr Asp Ala Ala Ala Ser Gly Pro Asp Ala Ala Cys
65                  70                  75                  80

Gly Gly Val Gly Ile Leu Gly Ile Ala Trp Ala Phe Gly Gly Met Ile
                85                  90                  95
```

-continued

```
Phe Ile Leu Val Tyr Cys Thr Ala Gly Ile Ser Gly Gly His Ile Asn
            100                 105                 110

Pro Ala Val Thr Phe Gly Leu Phe Leu Ala Arg Lys Val Ser Leu Val
        115                 120                 125

Arg Ala Leu Leu Tyr Ile Ile Ala Gln Cys Leu Gly Ala Ile Cys Gly
    130                 135                 140

Val Gly Leu Val Lys Gly Phe Gln Ser Ala Tyr Tyr Val Arg Tyr Gly
145                 150                 155                 160

Gly Gly Ala Asn Glu Leu Ser Asp Gly Tyr Ser Lys Gly Thr Gly Leu
                165                 170                 175

Ala Ala Glu Ile Ile Gly Thr Phe Val Leu Val Tyr Thr Val Phe Ser
            180                 185                 190

Ala Thr Asp Pro Lys Arg Ser Ala Arg Asp Ser His Val Pro Val Leu
        195                 200                 205

Ala Pro Leu Pro Ile Gly Phe Ala Val Phe Met Val His Leu Ala Thr
    210                 215                 220

Ile Pro Ile Thr Gly Thr Gly Ile Asn Pro Ala Arg Ser Leu Gly Ala
225                 230                 235                 240

Ala Val Ile Tyr Asn Lys Asp Lys Ala Trp Asp Asp Gln Trp Ile Phe
                245                 250                 255

Trp Val Gly Pro Leu Ile Gly Ala Ala Ile Ala Ala Ala Tyr His Gln
            260                 265                 270

Tyr Val Leu Arg Ala Ser Ala Thr Lys Leu Gly Ser Tyr Arg Ser Asn
        275                 280                 285

Ala


<210> SEQ ID NO 15
<211> LENGTH: 1304
<212> TYPE: DNA
<213> ORGANISM: Zea mays
<220> FEATURE:
<221> NAME/KEY: CDS
<222> LOCATION: (110)...(974)

<400> SEQUENCE: 15

cccgggtcga cccacgcgtc cgcgcaagca agcaattgtc aaccgactct atcttagctc      60

tctttgcaag ccagtaggtc accactcaaa agcttgtgaa gcaggtgag atg ggc aag     118
                                                      Met Gly Lys
                                                        1

gag gtg gat gtg tcc act cta gag gcc ggc ggc gtc cgt gac cgt gac       166
Glu Val Asp Val Ser Thr Leu Glu Ala Gly Gly Val Arg Asp Arg Asp
    5                  10                  15

tac gcg gac cct ccg ccg gca ccg ctg atc gac atc gac gag ctc ggc       214
Tyr Ala Asp Pro Pro Pro Ala Pro Leu Ile Asp Ile Asp Glu Leu Gly
 20                  25                  30                  35

aag tgg tcc ctg tac cgc gcc gtg atc gcc gag ttc gtg gcc acg ctg       262
Lys Trp Ser Leu Tyr Arg Ala Val Ile Ala Glu Phe Val Ala Thr Leu
                 40                  45                  50

ctg ttc ctg tac atc acg gtt gcc acg gtg atc ggg tac aag cac cag       310
Leu Phe Leu Tyr Ile Thr Val Ala Thr Val Ile Gly Tyr Lys His Gln
             55                  60                  65

acg gac gcg tcg gcg tcg ggg ccc gac gcg gcg tgc agc ggc gtg ggc       358
Thr Asp Ala Ser Ala Ser Gly Pro Asp Ala Ala Cys Ser Gly Val Gly
         70                  75                  80

atc ctg ggc atc gcg tgg gcg ttc ggc ggc atg atc ttc atc ctc gtc       406
Ile Leu Gly Ile Ala Trp Ala Phe Gly Gly Met Ile Phe Ile Leu Val
    85                  90                  95
```

-continued

```
tac tgc acc gcc ggc atc tcg ggc ggc cac atc aac ccg gcc gtc acg      454
Tyr Cys Thr Ala Gly Ile Ser Gly Gly His Ile Asn Pro Ala Val Thr
100                 105                 110                 115

ttc ggc ctc ttc ctg gcg cgc aag gtc tcc ctg gtg cgc gct ctg ctg      502
Phe Gly Leu Phe Leu Ala Arg Lys Val Ser Leu Val Arg Ala Leu Leu
                120                 125                 130

tac atg gcc gcg cag agc ctc ggt gct atc tgc ggc gtc gcg ctc gtc      550
Tyr Met Ala Ala Gln Ser Leu Gly Ala Ile Cys Gly Val Ala Leu Val
            135                 140                 145

aag ggc ttc cag agc ggg ttc tac gcg cgc tac ggc ggc ggc gcc aat      598
Lys Gly Phe Gln Ser Gly Phe Tyr Ala Arg Tyr Gly Gly Gly Ala Asn
        150                 155                 160

gag gtc agc gcc ggg tac tcc acc ggc acg ggg ctc gcc gcc gag atc      646
Glu Val Ser Ala Gly Tyr Ser Thr Gly Thr Gly Leu Ala Ala Glu Ile
    165                 170                 175

atc ggt acc ttc gtg ctc gtc tac acc gtc ttc tcc gcc acc gac ccc      694
Ile Gly Thr Phe Val Leu Val Tyr Thr Val Phe Ser Ala Thr Asp Pro
180                 185                 190                 195

aag cgc aac gct cgc gac tcc cac gtt ccg gtg ctg gcg ccg ctt ccg      742
Lys Arg Asn Ala Arg Asp Ser His Val Pro Val Leu Ala Pro Leu Pro
                200                 205                 210

atc ggg ttc gct gtg ttc atg gtg cac ctg gcg acg atc ccg atc act      790
Ile Gly Phe Ala Val Phe Met Val His Leu Ala Thr Ile Pro Ile Thr
            215                 220                 225

ggc acc ggt atc aac ccg gcg agg agc ctc ggc gcc gcc gtc gtg tac      838
Gly Thr Gly Ile Asn Pro Ala Arg Ser Leu Gly Ala Ala Val Val Tyr
        230                 235                 240

aac aac agc aaa gcc tgg agc gac cag tgg atc ttc tgg gtg ggc ccg      886
Asn Asn Ser Lys Ala Trp Ser Asp Gln Trp Ile Phe Trp Val Gly Pro
    245                 250                 255

ttc atc gga gcg gcg atc gca gcg cta tac cac cag atc gtc ctc cgc      934
Phe Ile Gly Ala Ala Ile Ala Ala Leu Tyr His Gln Ile Val Leu Arg
260                 265                 270                 275

gcc agc gcc agg ggg tac ggc tcc ttc cgg agc aac gcc t aggaccatct     984
Ala Ser Ala Arg Gly Tyr Gly Ser Phe Arg Ser Asn Ala
                280                 285

cgtcggcggg ctattcagct cttcctcctc cgcagtttaa ggtgaacgga gaaggagagc   1044

gcaaggggt acggagcaac gtctaggctc acctcgcctt tgccccgcc catccacagc   1104

agcagtagct ttcattcagg tcaagtgttg cagctgccgg caacggtagc tagcgcaggc   1164

gtttgtgagt ttgtgtgcgg tgtggaaagc aagtgtgact tggtcagcgt ctgtgtgtcc   1224

tgttgggttg cagtcaatct aacttaataa agatggacga atgcaagtga ttattaaaaa   1284

aaaaaaaaaa agggcggccg                                               1304


<210> SEQ ID NO 16
<211> LENGTH: 288
<212> TYPE: PRT
<213> ORGANISM: Zea mays

<400> SEQUENCE: 16

Met Gly Lys Glu Val Asp Val Ser Thr Leu Glu Ala Gly Gly Val Arg
 1               5                  10                  15

Asp Arg Asp Tyr Ala Asp Pro Pro Pro Ala Pro Leu Ile Asp Ile Asp
            20                  25                  30

Glu Leu Gly Lys Trp Ser Leu Tyr Arg Ala Val Ile Ala Glu Phe Val
        35                  40                  45

Ala Thr Leu Leu Phe Leu Tyr Ile Thr Val Ala Thr Val Ile Gly Tyr
    50                  55                  60
```

```
Lys His Gln Thr Asp Ala Ser Ala Ser Gly Pro Asp Ala Ala Cys Ser
65                  70                  75                  80

Gly Val Gly Ile Leu Gly Ile Ala Trp Ala Phe Gly Gly Met Ile Phe
                85                  90                  95

Ile Leu Val Tyr Cys Thr Ala Gly Ile Ser Gly Gly His Ile Asn Pro
            100                 105                 110

Ala Val Thr Phe Gly Leu Phe Leu Ala Arg Lys Val Ser Leu Val Arg
        115                 120                 125

Ala Leu Leu Tyr Met Ala Ala Gln Ser Leu Gly Ala Ile Cys Gly Val
    130                 135                 140

Ala Leu Val Lys Gly Phe Gln Ser Gly Phe Tyr Ala Arg Tyr Gly Gly
145                 150                 155                 160

Gly Ala Asn Glu Val Ser Ala Gly Tyr Ser Thr Gly Thr Gly Leu Ala
                165                 170                 175

Ala Glu Ile Ile Gly Thr Phe Val Leu Val Tyr Thr Val Phe Ser Ala
            180                 185                 190

Thr Asp Pro Lys Arg Asn Ala Arg Asp Ser His Val Pro Val Leu Ala
        195                 200                 205

Pro Leu Pro Ile Gly Phe Ala Val Phe Met Val His Leu Ala Thr Ile
    210                 215                 220

Pro Ile Thr Gly Thr Gly Ile Asn Pro Ala Arg Ser Leu Gly Ala Ala
225                 230                 235                 240

Val Val Tyr Asn Asn Ser Lys Ala Trp Ser Asp Gln Trp Ile Phe Trp
                245                 250                 255

Val Gly Pro Phe Ile Gly Ala Ala Ile Ala Ala Leu Tyr His Gln Ile
            260                 265                 270

Val Leu Arg Ala Ser Ala Arg Gly Tyr Gly Ser Phe Arg Ser Asn Ala
        275                 280                 285


<210> SEQ ID NO 17
<211> LENGTH: 1384
<212> TYPE: DNA
<213> ORGANISM: Zea mays
<220> FEATURE:
<221> NAME/KEY: CDS
<222> LOCATION: (95)...(959)

<400> SEQUENCE: 17

cccgggtcga cccacgcgtc cgcccacgcg tccgccagtg tcccagctca gcttagcaat     60

ccgtctctct atctacaggc gggggaatta atag atg gag ggc aag gag gag gac    115
                                      Met Glu Gly Lys Glu Glu Asp
                                        1               5

gtt cgc ctg ggc gcc aac cgc tac tcg gag cgc cag cca atc ggc acg      163
Val Arg Leu Gly Ala Asn Arg Tyr Ser Glu Arg Gln Pro Ile Gly Thr
        10                  15                  20

gcg gcg cag ggc acg gag gag aag gac tac aag gag cct ccg ccg gcg      211
Ala Ala Gln Gly Thr Glu Glu Lys Asp Tyr Lys Glu Pro Pro Pro Ala
    25                  30                  35

ccg ctg ttc gag gcg gag gag ctg acg tcg tgg tcc ttc tac cgg gcc      259
Pro Leu Phe Glu Ala Glu Glu Leu Thr Ser Trp Ser Phe Tyr Arg Ala
 40                  45                  50                  55

ggg atc gcc gag ttc gtg gcc acc ttc ctg ttc ctg tac atc agc atc      307
Gly Ile Ala Glu Phe Val Ala Thr Phe Leu Phe Leu Tyr Ile Ser Ile
                 60                  65                  70

ctg act gtg atg ggc gtg agc aag tcg tcc agc aag tgc gcc acc gtg      355
Leu Thr Val Met Gly Val Ser Lys Ser Ser Ser Lys Cys Ala Thr Val
             75                  80                  85
```

-continued

```
ggc atc cag ggc atc gcg tgg tcc ttc ggc ggc atg atc ttc gcg ctg      403
Gly Ile Gln Gly Ile Ala Trp Ser Phe Gly Gly Met Ile Phe Ala Leu
        90                  95                 100

gtg tac tgc acg gcg ggc atc tcc ggc ggc cac atc aac ccg gcc gtc      451
Val Tyr Cys Thr Ala Gly Ile Ser Gly Gly His Ile Asn Pro Ala Val
    105                 110                 115

acc ttc ggc ctc ttc ctg gcg cgg aag ctg tcg ctc acg cgc gcg ctc      499
Thr Phe Gly Leu Phe Leu Ala Arg Lys Leu Ser Leu Thr Arg Ala Leu
120                 125                 130                 135

ttc tac atg gtc atg cag tgc ctg ggc gcc atc tgc ggc gcc ggc gtc      547
Phe Tyr Met Val Met Gln Cys Leu Gly Ala Ile Cys Gly Ala Gly Val
                140                 145                 150

gtc aag ggc ttc cag gag ggc ctc tac atg ggc gcc ggc ggc ggc gcc      595
Val Lys Gly Phe Gln Glu Gly Leu Tyr Met Gly Ala Gly Gly Gly Ala
            155                 160                 165

aac gcc gtc aac ccc ggg tac acc aag ggc gac ggg ctc ggg gcg gag      643
Asn Ala Val Asn Pro Gly Tyr Thr Lys Gly Asp Gly Leu Gly Ala Glu
        170                 175                 180

atc gtc ggc acc ttc gtg ctc gtc tac acc gtc ttc tcc gcc acc gac      691
Ile Val Gly Thr Phe Val Leu Val Tyr Thr Val Phe Ser Ala Thr Asp
    185                 190                 195

gcc aag cgc agc gcc cgc gac tcc cac gtg ccc atc ctc gcg ccg ctc      739
Ala Lys Arg Ser Ala Arg Asp Ser His Val Pro Ile Leu Ala Pro Leu
200                 205                 210                 215

ccc ata ggc ttc gcc gtc ttc ctc gtg cac ctg gcg acc atc ccc atc      787
Pro Ile Gly Phe Ala Val Phe Leu Val His Leu Ala Thr Ile Pro Ile
                220                 225                 230

acc ggc acc ggc atc aac ccc gcg cgc agc ctc ggc gcc gcc atc gtc      835
Thr Gly Thr Gly Ile Asn Pro Ala Arg Ser Leu Gly Ala Ala Ile Val
            235                 240                 245

tac aac agg tcc cac gca tgg aac gac cac tgg atc ttc tgg gtt ggc      883
Tyr Asn Arg Ser His Ala Trp Asn Asp His Trp Ile Phe Trp Val Gly
        250                 255                 260

ccc ttc atc ggt gct gct ctt gcc gcc atc tac cac gtg gtc atc atc      931
Pro Phe Ile Gly Ala Ala Leu Ala Ala Ile Tyr His Val Val Ile Ile
    265                 270                 275

agg gcc ctc ccc ttc aag agc cgt gac t gattatacgt acattgttta          979
Arg Ala Leu Pro Phe Lys Ser Arg Asp
280                 285

ttaccaacag caaccatgca gcatacgaat catcgttatt aagctatata tgtataatat   1039

ccagcatgtc ttgttaatta ctagtatatg tgctagtaag tggtgcgtgc tcgctcttcc   1099

atcgctgtcg tcgtctcatc tgctattgtt cgtcatatat atatgtccat gtgagctagc   1159

tagtgtgtat cacgcgcgga ggccagttca gctagccatc agtctgcaat gcactttgtg   1219

acttctctgt ttagtcctct ctcgcttggg ttttggtacg gtgaagtata taaactaagc   1279

atgcatatgt gtaaaaattc aaattcaagt gtatgcatgc atgccaataa tgaaagttaa   1339

gaagaagact ccctgtttat gaaaaaaaaa aaaaaagggc ggccg                   1384


<210> SEQ ID NO 18
<211> LENGTH: 288
<212> TYPE: PRT
<213> ORGANISM: Zea mays

<400> SEQUENCE: 18

Met Glu Gly Lys Glu Glu Asp Val Arg Leu Gly Ala Asn Arg Tyr Ser
 1               5                  10                  15

Glu Arg Gln Pro Ile Gly Thr Ala Ala Gln Gly Thr Glu Glu Lys Asp
```

-continued

```
            20                  25                  30

Tyr Lys Glu Pro Pro Pro Ala Pro Leu Phe Glu Ala Glu Glu Leu Thr
        35                  40                  45

Ser Trp Ser Phe Tyr Arg Ala Gly Ile Ala Glu Phe Val Ala Thr Phe
    50                  55                  60

Leu Phe Leu Tyr Ile Ser Ile Leu Thr Val Met Gly Val Ser Lys Ser
65                  70                  75                  80

Ser Ser Lys Cys Ala Thr Val Gly Ile Gln Gly Ile Ala Trp Ser Phe
                85                  90                  95

Gly Gly Met Ile Phe Ala Leu Val Tyr Cys Thr Ala Gly Ile Ser Gly
            100                 105                 110

Gly His Ile Asn Pro Ala Val Thr Phe Gly Leu Phe Leu Ala Arg Lys
        115                 120                 125

Leu Ser Leu Thr Arg Ala Leu Phe Tyr Met Val Met Gln Cys Leu Gly
    130                 135                 140

Ala Ile Cys Gly Ala Gly Val Val Lys Gly Phe Gln Glu Gly Leu Tyr
145                 150                 155                 160

Met Gly Ala Gly Gly Gly Ala Asn Ala Val Asn Pro Gly Tyr Thr Lys
                165                 170                 175

Gly Asp Gly Leu Gly Ala Glu Ile Val Gly Thr Phe Val Leu Val Tyr
            180                 185                 190

Thr Val Phe Ser Ala Thr Asp Ala Lys Arg Ser Ala Arg Asp Ser His
        195                 200                 205

Val Pro Ile Leu Ala Pro Leu Pro Ile Gly Phe Ala Val Phe Leu Val
    210                 215                 220

His Leu Ala Thr Ile Pro Ile Thr Gly Thr Gly Ile Asn Pro Ala Arg
225                 230                 235                 240

Ser Leu Gly Ala Ala Ile Val Tyr Asn Arg Ser His Ala Trp Asn Asp
                245                 250                 255

His Trp Ile Phe Trp Val Gly Pro Phe Ile Gly Ala Ala Leu Ala Ala
            260                 265                 270

Ile Tyr His Val Val Ile Ile Arg Ala Leu Pro Phe Lys Ser Arg Asp
        275                 280                 285


<210> SEQ ID NO 19
<211> LENGTH: 1454
<212> TYPE: DNA
<213> ORGANISM: Zea mays
<220> FEATURE:
<221> NAME/KEY: CDS
<222> LOCATION: (224)...(1112)

<400> SEQUENCE: 19

cccgggtcga cccacgcgtc cgccgaatcg atttgtccat ttgctgcacg catgactcga      60

catgcatgga attggatggg tcctactaat gctgtggcgc tgcagcctat ataagaacac     120

tacacacata gctcttgaca cgtcgcttca tctagtccca gcactactca ctcacttcca     180

gtctctagag ccatcaagat cgtagctgag cgagttagta ttc atg gca gga ggc       235
                                                Met Ala Gly Gly
                                                 1

acg ctg cag gac aga tcg gag gaa gag gac gtg cgc gtg ggc gtg gac       283
Thr Leu Gln Asp Arg Ser Glu Glu Glu Asp Val Arg Val Gly Val Asp
 5                  10                  15                  20

cgt ttc ccg gag cgg cag ccc atc ggc acg gcg gcg gac gac ctg ggc       331
Arg Phe Pro Glu Arg Gln Pro Ile Gly Thr Ala Ala Asp Asp Leu Gly
                25                  30                  35
```

-continued

```
cgc gac tac agc gag ccc ccg gcg gcg ccg ctg ttc gag gcg tcg gag      379
Arg Asp Tyr Ser Glu Pro Pro Ala Ala Pro Leu Phe Glu Ala Ser Glu
             40                  45                  50

ctc tcc tcg tgg tcc ttc tac cgc gcc ggc atc gcc gag ttc gtg gcc      427
Leu Ser Ser Trp Ser Phe Tyr Arg Ala Gly Ile Ala Glu Phe Val Ala
         55                  60                  65

acg ttc ctc ttc ctg tac gtg acc gtg ctg acg gtg atg ggc gtg agc      475
Thr Phe Leu Phe Leu Tyr Val Thr Val Leu Thr Val Met Gly Val Ser
     70                  75                  80

aag tcc ccc tcc aag tgc ggc acc gtg ggc atc cag ggc atc gcg tgg      523
Lys Ser Pro Ser Lys Cys Gly Thr Val Gly Ile Gln Gly Ile Ala Trp
 85                  90                  95                 100

gcg ttc ggc ggc atg atc ttc gcg ctc gtg tac tgc acc gcg ggc gtg      571
Ala Phe Gly Gly Met Ile Phe Ala Leu Val Tyr Cys Thr Ala Gly Val
                105                 110                 115

tcg ggc ggc cac atc aac ccg gcc gtc acg ttc ggc ctc ctc ctc gcc      619
Ser Gly Gly His Ile Asn Pro Ala Val Thr Phe Gly Leu Leu Leu Ala
            120                 125                 130

cgg aag ctg tcg ctg acg cgg gcg gtc tac tac gtg gtg atg cag tgc      667
Arg Lys Leu Ser Leu Thr Arg Ala Val Tyr Tyr Val Val Met Gln Cys
        135                 140                 145

ctg ggc gcc gtc tgc ggc gcc ggc gtc gtg aag gcg ttc ggc agc gcg      715
Leu Gly Ala Val Cys Gly Ala Gly Val Val Lys Ala Phe Gly Ser Ala
    150                 155                 160

ctg tac gag tcc gcg ggc ggc ggc gcc aac gcc gtc agc ccc ggg tac      763
Leu Tyr Glu Ser Ala Gly Gly Gly Ala Asn Ala Val Ser Pro Gly Tyr
165                 170                 175                 180

acc aag ggc gac ggc ctc ggc gcc gag gtc gtg ggc acg ttc gtg ctc      811
Thr Lys Gly Asp Gly Leu Gly Ala Glu Val Val Gly Thr Phe Val Leu
                185                 190                 195

gtg tac acc gtc ttc tcc gcc acc gac gcc aag cgc acc gcc agg gac      859
Val Tyr Thr Val Phe Ser Ala Thr Asp Ala Lys Arg Thr Ala Arg Asp
            200                 205                 210

tcc cac gtc ccc gcg ctg gcc ccg ctg ccc atc ggc ttc gcc gta ttc      907
Ser His Val Pro Ala Leu Ala Pro Leu Pro Ile Gly Phe Ala Val Phe
        215                 220                 225

ctg gtg cac ctc gcc acc atc ccc atc acc ggc acc ggc atc aac ccc      955
Leu Val His Leu Ala Thr Ile Pro Ile Thr Gly Thr Gly Ile Asn Pro
    230                 235                 240

gcc agg agc ctc ggc gcc gcc atc atc tac gac aac ccg cac ggg tgg     1003
Ala Arg Ser Leu Gly Ala Ala Ile Ile Tyr Asp Asn Pro His Gly Trp
245                 250                 255                 260

cac ggc cac tgg atc ttc tgg gtg ggc ccg ttc gcc gga gcg gcg ctt     1051
His Gly His Trp Ile Phe Trp Val Gly Pro Phe Ala Gly Ala Ala Leu
                265                 270                 275

gcg gcg gtg tac cac cag gtc gtc ctc agg gcc atc ccc ttc aag tcc     1099
Ala Ala Val Tyr His Gln Val Val Leu Arg Ala Ile Pro Phe Lys Ser
            280                 285                 290

agc gct cac tac t agtgttgctt gccttgccgt catacacgga gttctgctgc       1152
Ser Ala His Tyr
        295

cacatcggcc gctcaatggg ccatcactcc gcgaatgtat gatgtgtgta actcgaatgt   1212

gtggttaatt ttcgttttct tacgtgtttg catccacgga atgtgtcatc agtgtacaaa   1272

tcaactgtat gtggctgtac gtgtcccaat tatgataatg ctaataaggc cataatatac   1332

caaggcccat ttactaaaaa aaaaaaaaaa aaaaaaaaaa aaaaaaaaaa aaaaaaaaaa   1392

aaaaaaaaaa aaaaaaaaaa aaaaaaaaaa aaaaaaaaaa aaaaaaaaaa aaagggcggc   1452

cg                                                                  1454
```

<210> SEQ ID NO 20
<211> LENGTH: 296
<212> TYPE: PRT
<213> ORGANISM: Zea mays

<400> SEQUENCE: 20

```
Met Ala Gly Gly Thr Leu Gln Asp Arg Ser Glu Glu Glu Asp Val Arg
 1               5                  10                  15

Val Gly Val Asp Arg Phe Pro Glu Arg Gln Pro Ile Gly Thr Ala Ala
            20                  25                  30

Asp Asp Leu Gly Arg Asp Tyr Ser Glu Pro Pro Ala Ala Pro Leu Phe
        35                  40                  45

Glu Ala Ser Glu Leu Ser Ser Trp Ser Phe Tyr Arg Ala Gly Ile Ala
    50                  55                  60

Glu Phe Val Ala Thr Phe Leu Phe Leu Tyr Val Thr Val Leu Thr Val
65                  70                  75                  80

Met Gly Val Ser Lys Ser Pro Ser Lys Cys Gly Thr Val Gly Ile Gln
                85                  90                  95

Gly Ile Ala Trp Ala Phe Gly Gly Met Ile Phe Ala Leu Val Tyr Cys
            100                 105                 110

Thr Ala Gly Val Ser Gly Gly His Ile Asn Pro Ala Val Thr Phe Gly
        115                 120                 125

Leu Leu Leu Ala Arg Lys Leu Ser Leu Thr Arg Ala Val Tyr Tyr Val
    130                 135                 140

Val Met Gln Cys Leu Gly Ala Val Cys Gly Ala Gly Val Val Lys Ala
145                 150                 155                 160

Phe Gly Ser Ala Leu Tyr Glu Ser Ala Gly Gly Gly Ala Asn Ala Val
                165                 170                 175

Ser Pro Gly Tyr Thr Lys Gly Asp Gly Leu Gly Ala Glu Val Val Gly
            180                 185                 190

Thr Phe Val Leu Val Tyr Thr Val Phe Ser Ala Thr Asp Ala Lys Arg
        195                 200                 205

Thr Ala Arg Asp Ser His Val Pro Ala Leu Ala Pro Leu Pro Ile Gly
    210                 215                 220

Phe Ala Val Phe Leu Val His Leu Ala Thr Ile Pro Ile Thr Gly Thr
225                 230                 235                 240

Gly Ile Asn Pro Ala Arg Ser Leu Gly Ala Ala Ile Ile Tyr Asp Asn
                245                 250                 255

Pro His Gly Trp His Gly His Trp Ile Phe Trp Val Gly Pro Phe Ala
            260                 265                 270

Gly Ala Ala Leu Ala Ala Val Tyr His Gln Val Val Leu Arg Ala Ile
        275                 280                 285

Pro Phe Lys Ser Ser Ala His Tyr
    290                 295
```

<210> SEQ ID NO 21
<211> LENGTH: 1158
<212> TYPE: DNA
<213> ORGANISM: Zea mays
<220> FEATURE:
<221> NAME/KEY: CDS
<222> LOCATION: (250)...(997)

<400> SEQUENCE: 21

```
cccgggtcga cccacgcgtc cgaaatgttt tgtgacgatt atccccgcac cgtccagagt     60
```

-continued

```
actctaaccc acaagttgag gccgccctgc agcccatcag acgaggacgc gcgcgtgtat    120

aaaagctgac tggactccca gcgtctgtca gcgaagccga agcagcagcc aattcgctcg    180

agttcagatc gagcgcgcgc caagcaagtc ttccggccgg ccgcgaagag cgcaatcaag    240

caagacaag atg gtg aag ctc gcc ttc gga agc gtc ggc gac tcc ttc agc    291
          Met Val Lys Leu Ala Phe Gly Ser Val Gly Asp Ser Phe Ser
           1               5                  10

gcc acc tcc atc aag gcc tac gtg gcc gag ttc atc gcc acc ctc ctc      339
Ala Thr Ser Ile Lys Ala Tyr Val Ala Glu Phe Ile Ala Thr Leu Leu
 15                  20                  25                  30

ttc gtc ttc gcc ggc gtc ggt tcc gcc atc gcc tac ggg caa ctg acg      387
Phe Val Phe Ala Gly Val Gly Ser Ala Ile Ala Tyr Gly Gln Leu Thr
                 35                  40                  45

aat ggc ggc gcg ctg gac ccg gcg ggc ctg gtg gcg atc gcg atc gcg      435
Asn Gly Gly Ala Leu Asp Pro Ala Gly Leu Val Ala Ile Ala Ile Ala
             50                  55                  60

cac gcg ctg gcg ctg ttc gtg ggc gtg tcc gtc gcg gcg aac atc tcg      483
His Ala Leu Ala Leu Phe Val Gly Val Ser Val Ala Ala Asn Ile Ser
         65                  70                  75

ggc ggc cac ctg aac ccg gcc gtg acg ttc ggg ctg gcc gtg ggc ggc      531
Gly Gly His Leu Asn Pro Ala Val Thr Phe Gly Leu Ala Val Gly Gly
     80                  85                  90

cac atc acc atc ctg acg ggc gtc ttc tac tgg gtg gcc cag ctg ctg      579
His Ile Thr Ile Leu Thr Gly Val Phe Tyr Trp Val Ala Gln Leu Leu
 95                 100                 105                 110

ggc gcc acc gtg gcg tgc ctg ctc ctc ggg ttc gtc acc cac ggc aag      627
Gly Ala Thr Val Ala Cys Leu Leu Leu Gly Phe Val Thr His Gly Lys
                115                 120                 125

gcc atc ccg acg cac gcc gtc gcg ggc atc agc gag ctg gaa ggc gtc      675
Ala Ile Pro Thr His Ala Val Ala Gly Ile Ser Glu Leu Glu Gly Val
            130                 135                 140

gtg ttc gag gtc gtc atc acc ttc gcg ctc gtc tac acc gtg tac gcc      723
Val Phe Glu Val Val Ile Thr Phe Ala Leu Val Tyr Thr Val Tyr Ala
        145                 150                 155

acc gcc gcc gac ccc aag aag ggc tcg ctc ggc acc atc gcg ccc atc      771
Thr Ala Ala Asp Pro Lys Lys Gly Ser Leu Gly Thr Ile Ala Pro Ile
    160                 165                 170

gcc atc ggc ttc atc gtc ggc gcc aac atc ctc gcc gcg ggg ccc ttc      819
Ala Ile Gly Phe Ile Val Gly Ala Asn Ile Leu Ala Ala Gly Pro Phe
175                 180                 185                 190

agc ggc ggc tcc atg aac ccc gcc cgc tcc ttc ggc ccc gcc gtc gcc      867
Ser Gly Gly Ser Met Asn Pro Ala Arg Ser Phe Gly Pro Ala Val Ala
                195                 200                 205

gcg ggc gac ttc gcc gga aac tgg gtc tac tgg gtc ggc ccg ctc gtc      915
Ala Gly Asp Phe Ala Gly Asn Trp Val Tyr Trp Val Gly Pro Leu Val
            210                 215                 220

ggc ggc ggc ctc gct ggc ctc gtc tac ggc gac gtc ttc att ggc ggc      963
Gly Gly Gly Leu Ala Gly Leu Val Tyr Gly Asp Val Phe Ile Gly Gly
        225                 230                 235

tcc tac cag cag gtc gcg gac cag gac tac gcc t aatttattca            1007
Ser Tyr Gln Gln Val Ala Asp Gln Asp Tyr Ala
    240                 245

ccactccatc tccgctctgg atgaatggat tcaaaaccgt cgtcgtttgc ttttgctcct   1067

cgccacgttc aattaatggt tgtgtatgca tgtatgtgcc aatatgatgt gcctttgccc   1127

tggtcaaaaa aaaaaaaaaa aagggcggcc g                                   1158


<210> SEQ ID NO 22
<211> LENGTH: 249
```

```
<212> TYPE: PRT
<213> ORGANISM: Zea mays

<400> SEQUENCE: 22

Met Val Lys Leu Ala Phe Gly Ser Val Gly Asp Ser Phe Ser Ala Thr
 1               5                  10                  15

Ser Ile Lys Ala Tyr Val Ala Glu Phe Ile Ala Thr Leu Leu Phe Val
            20                  25                  30

Phe Ala Gly Val Gly Ser Ala Ile Ala Tyr Gly Gln Leu Thr Asn Gly
        35                  40                  45

Gly Ala Leu Asp Pro Ala Gly Leu Val Ala Ile Ala Ile Ala His Ala
    50                  55                  60

Leu Ala Leu Phe Val Gly Val Ser Val Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Val Phe Tyr Trp Val Ala Gln Leu Leu Gly Ala
            100                 105                 110

Thr Val Ala Cys Leu Leu Leu Gly Phe Val Thr His Gly Lys Ala Ile
        115                 120                 125

Pro Thr His Ala Val Ala Gly Ile Ser Glu Leu Glu Gly Val Val Phe
    130                 135                 140

Glu Val Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asp Phe Ala Gly Asn Trp Val Tyr Trp Val Gly Pro Leu Val Gly Gly
    210                 215                 220

Gly Leu Ala Gly Leu Val Tyr Gly Asp Val Phe Ile Gly Gly Ser Tyr
225                 230                 235                 240

Gln Gln Val Ala Asp Gln Asp Tyr Ala
                245


<210> SEQ ID NO 23
<211> LENGTH: 1193
<212> TYPE: DNA
<213> ORGANISM: Zea mays
<220> FEATURE:
<221> NAME/KEY: CDS
<222> LOCATION: (88)...(838)

<400> SEQUENCE: 23

cccgggtcga cccacgcgtc cgatatcaag ctcagagcct cagagcgcca gccaagtctt      60

gcggttcgcg aagagcaacg caacaag atg gtg aag ctc gca ttc gga agc gtc    114
                              Met Val Lys Leu Ala Phe Gly Ser Val
                               1               5

ggc gac tcc ttc agc gtc acc tcc atc aag ggc cta cgt tgg cgg agt      162
Gly Asp Ser Phe Ser Val Thr Ser Ile Lys Gly Leu Arg Trp Arg Ser
 10                  15                  20                  25

ttc atc gca ccc tcc tct tcg tct tcg ccg gcg tgg ttc cgc atc gcc      210
Phe Ile Ala Pro Ser Ser Ser Ser Ser Pro Ala Trp Phe Arg Ile Ala
                30                  35                  40

ttc ggg caa ctg acg aat ggc ggc gcg ctg gac cct gcg gga ctg gtg      258
```

-continued

```
Phe Gly Gln Leu Thr Asn Gly Gly Ala Leu Asp Pro Ala Gly Leu Val
             45                  50                  55

gcg atc gcg gtg gcg cac gcg ctg gcc ctc ttc gtg ggc gtc tcc gtg      306
Ala Ile Ala Val Ala His Ala Leu Ala Leu Phe Val Gly Val Ser Val
         60                  65                  70

gcc gcg aac acc tcc ggc ggc cac ctg aac ccc gcc gtg acg ttc ggc      354
Ala Ala Asn Thr Ser Gly Gly His Leu Asn Pro Ala Val Thr Phe Gly
     75                  80                  85

ctg gcc gtg ggc ggc cac atc acc gtc ctc acc ggc ctc ttc tac tgg      402
Leu Ala Val Gly Gly His Ile Thr Val Leu Thr Gly Leu Phe Tyr Trp
 90                  95                 100                 105

gtg gcc cag ctg ctg ggc gcg tcc gtg gcg tgc ctg ctc ctc agg ttc      450
Val Ala Gln Leu Leu Gly Ala Ser Val Ala Cys Leu Leu Leu Arg Phe
                110                 115                 120

gtg acc cac ggc aag gcc atc ccg acc cac ggc gtc tcc ggc ggc acc      498
Val Thr His Gly Lys Ala Ile Pro Thr His Gly Val Ser Gly Gly Thr
            125                 130                 135

acc gag ctg gag ggc gtc gtg ttc gag atc gtc atc acc ttc gcg ctc      546
Thr Glu Leu Glu Gly Val Val Phe Glu Ile Val Ile Thr Phe Ala Leu
        140                 145                 150

gtc tac acc gtg tac gcc acc gcc gcc gac ccc aag aag ggc tcc ctc      594
Val Tyr Thr Val Tyr Ala Thr Ala Ala Asp Pro Lys Lys Gly Ser Leu
    155                 160                 165

ggc acc atc gcg ccc atc gcc atc ggc ttc atc gtc ggc gcc aac atc      642
Gly Thr Ile Ala Pro Ile Ala Ile Gly Phe Ile Val Gly Ala Asn Ile
170                 175                 180                 185

ctc gcc gcg ggg ccc ttc agc ggc ggc tcc atg aac ccc gcc cgc tcc      690
Leu Ala Ala Gly Pro Phe Ser Gly Gly Ser Met Asn Pro Ala Arg Ser
                190                 195                 200

ttc ggc ccc gcc gtc gcc gcg gcc gac ttc gcc ggc aac tgg gtc tac      738
Phe Gly Pro Ala Val Ala Ala Ala Asp Phe Ala Gly Asn Trp Val Tyr
            205                 210                 215

tgg gtc ggc ccg ctc atc ggc ggc gga ctc gct ggc ctc gtc tac ggc      786
Trp Val Gly Pro Leu Ile Gly Gly Gly Leu Ala Gly Leu Val Tyr Gly
        220                 225                 230

gac gtc ttc atc ggc ggc tcc tac cag cag gtc gcc gac cag gac tac      834
Asp Val Phe Ile Gly Gly Ser Tyr Gln Gln Val Ala Asp Gln Asp Tyr
    235                 240                 245

gcc t aagtagtgtg ctccgttcgt ctggattcag ctcatccaac gcaggcgcgc        888
Ala
250

gtttcgatcg gcgtcgtcat ttgctttgct cttcatttca tcacgttatg taacgtgcca    948

atgatgtgtg tcgtcctggt ctgttccatt ccgtccttgt attcatttcc cttctttttt   1008

cggggtaaaa tcgatgtaaa gatctcatcc gatctgccgt tttcgatcgc cttggagtgg   1068

gaaaaaacag gtgattttcg tttcgaaaaa aaaaaaaaaa aaaaaaaaaa aaaaaaaaaa   1128

aaaaaaaaaa aaaaaaaaaa aaaaaaaaaa aaaaaaaaaa aaaaaaaaaa aaaagggcgg   1188

ccgcc                                                               1193


<210> SEQ ID NO 24
<211> LENGTH: 250
<212> TYPE: PRT
<213> ORGANISM: Zea mays

<400> SEQUENCE: 24

Met Val Lys Leu Ala Phe Gly Ser Val Gly Asp Ser Phe Ser Val Thr
 1               5                  10                  15

Ser Ile Lys Gly Leu Arg Trp Arg Ser Phe Ile Ala Pro Ser Ser Ser
```

-continued

```
            20                  25                  30

Ser Ser Pro Ala Trp Phe Arg Ile Ala Phe Gly Gln Leu Thr Asn Gly
        35                  40                  45

Gly Ala Leu Asp Pro Ala Gly Leu Val Ala Ile Ala Val Ala His Ala
    50                  55                  60

Leu Ala Leu Phe Val Gly Val Ser Val Ala Ala Asn Thr Ser Gly Gly
65                  70                  75                  80

His Leu Asn Pro Ala Val Thr Phe Gly Leu Ala Val Gly Gly His Ile
                85                  90                  95

Thr Val Leu Thr Gly Leu Phe Tyr Trp Val Ala Gln Leu Leu Gly Ala
            100                 105                 110

Ser Val Ala Cys Leu Leu Leu Arg Phe Val Thr His Gly Lys Ala Ile
        115                 120                 125

Pro Thr His Gly Val Ser Gly Gly Thr Thr Glu Leu Glu Gly Val Val
    130                 135                 140

Phe Glu Ile Val Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Ala Asp Phe Ala Gly Asn Trp Val Tyr Trp Val Gly Pro Leu Ile Gly
    210                 215                 220

Gly Gly Leu Ala Gly Leu Val Tyr Gly Asp Val Phe Ile Gly Gly Ser
225                 230                 235                 240

Tyr Gln Gln Val Ala Asp Gln Asp Tyr Ala
                245                 250


<210> SEQ ID NO 25
<211> LENGTH: 1176
<212> TYPE: DNA
<213> ORGANISM: Zea mays
<220> FEATURE:
<221> NAME/KEY: CDS
<222> LOCATION: (159)...(975)

<400> SEQUENCE: 25

cccgggtcga cccacgcgtc cgcaaaatag gcgtatctcc ctgcgctttt cctagccctt     60

tgtcatccaa ggaaacaata aacaaccggc gcttttacac cccgccaag aacaggagca    120

acaacaacaa ggctcctcgc aacaatccat tctcatcc atg gcg aag ctc atg aac    176
                                          Met Ala Lys Leu Met Asn
                                           1               5

aag ttg gtc gat tcg ttc gag cac gac gag ata ccg gac gtc ggc tgc      224
Lys Leu Val Asp Ser Phe Glu His Asp Glu Ile Pro Asp Val Gly Cys
            10                  15                  20

gtg cgc gcc gtg ctg gcc gag ctc gtc ctc acc ttc ctc ttc gtc ttc      272
Val Arg Ala Val Leu Ala Glu Leu Val Leu Thr Phe Leu Phe Val Phe
        25                  30                  35

acc ggc gtc tcc gcc gcc atg gcc gcc gga tcc gac ggg aag ccc ggc      320
Thr Gly Val Ser Ala Ala Met Ala Ala Gly Ser Asp Gly Lys Pro Gly
     40                  45                  50

gac gct atg ccg atg gcg acg ctg gcg gcg gtg gca atc gcg cac gcg      368
Asp Ala Met Pro Met Ala Thr Leu Ala Ala Val Ala Ile Ala His Ala
 55                  60                  65                  70
```

-continued

```
ctg gcc gct ggc gtc ctg gtg acg gcc ggg ttc cac gtc tcc ggc ggc      416
Leu Ala Ala Gly Val Leu Val Thr Ala Gly Phe His Val Ser Gly Gly
                75                  80                  85

cac ctg aac ccc gcg gtg acg gtg ggg ctc atg gtg cgc ggc cac atc      464
His Leu Asn Pro Ala Val Thr Val Gly Leu Met Val Arg Gly His Ile
            90                  95                  100

acc aag ctc cgg gcg gtg ctg tac gtc gcc gcc cag ctg ctg gcc tcc      512
Thr Lys Leu Arg Ala Val Leu Tyr Val Ala Ala Gln Leu Leu Ala Ser
        105                 110                 115

tcc gcc gcc tgc gtc ctc ctc cgc ttc ctc agc ggc ggc atg gtg acc      560
Ser Ala Ala Cys Val Leu Leu Arg Phe Leu Ser Gly Gly Met Val Thr
    120                 125                 130

ccg gtg cac gcc ctg ggc agg ggc atc agc ccg atg cag ggc ctg gtg      608
Pro Val His Ala Leu Gly Arg Gly Ile Ser Pro Met Gln Gly Leu Val
135                 140                 145                 150

atg gag gtg atc ctc acc ttc tcc ctg ctc ttc gtc acc tac gcc atg      656
Met Glu Val Ile Leu Thr Phe Ser Leu Leu Phe Val Thr Tyr Ala Met
                155                 160                 165

atc ctg gac ccg cgg agc cag gtc cgc gcc atc ggc ccg ctg ctg acg      704
Ile Leu Asp Pro Arg Ser Gln Val Arg Ala Ile Gly Pro Leu Leu Thr
            170                 175                 180

ggc ctc atc gtc ggc gcc aac agc ctc gcc ggc ggc aac ttc acc ggc      752
Gly Leu Ile Val Gly Ala Asn Ser Leu Ala Gly Gly Asn Phe Thr Gly
        185                 190                 195

gcg tcc atg aac ccg gca cgc tcc ttc ggc ccg gcc ctg gcc acc ggg      800
Ala Ser Met Asn Pro Ala Arg Ser Phe Gly Pro Ala Leu Ala Thr Gly
    200                 205                 210

gac tgg aca aac cac tgg gtc tac tgg atc ggc ccg ctg ctc ggc ggg      848
Asp Trp Thr Asn His Trp Val Tyr Trp Ile Gly Pro Leu Leu Gly Gly
215                 220                 225                 230

ccc ctg gca ggc ttc gtg tac gag tcg ctg ttc ctg gtg cag aag atg      896
Pro Leu Ala Gly Phe Val Tyr Glu Ser Leu Phe Leu Val Gln Lys Met
                235                 240                 245

cac gaa gcc gct gct caa tgg gga agt ctg acg acc atc agc ccc tgt      944
His Glu Ala Ala Ala Gln Trp Gly Ser Leu Thr Thr Ile Ser Pro Cys
            250                 255                 260

gtt gtg gcg cat gct tca tgc ttg ttt ctg t aaaacaggtc attctctgca      995
Val Val Ala His Ala Ser Cys Leu Phe Leu
        265                 270

agcatggtac atacattggc caaggtaatt agagaggctt gctgtaaagc agtaggattg   1055

ctggctgtag aaattgttga tggggctttt ttgggggttt cctgccaagg aattcttttct   1115

tttatataat ctcaaaaaag tttttttttt ggtaaaaaaa aaaaaaaaaa aagggcggcc   1175

g                                                                   1176
```

```
<210> SEQ ID NO 26
<211> LENGTH: 272
<212> TYPE: PRT
<213> ORGANISM: Zea mays

<400> SEQUENCE: 26

Met Ala Lys Leu Met Asn Lys Leu Val Asp Ser Phe Glu His Asp Glu
 1               5                  10                  15

Ile Pro Asp Val Gly Cys Val Arg Ala Val Leu Ala Glu Leu Val Leu
            20                  25                  30

Thr Phe Leu Phe Val Phe Thr Gly Val Ser Ala Ala Met Ala Ala Gly
        35                  40                  45

Ser Asp Gly Lys Pro Gly Asp Ala Met Pro Met Ala Thr Leu Ala Ala
    50                  55                  60
```

```
Val Ala Ile Ala His Ala Leu Ala Ala Gly Val Leu Val Thr Ala Gly
65                  70                  75                  80

Phe His Val Ser Gly Gly His Leu Asn Pro Ala Val Thr Val Gly Leu
                85                  90                  95

Met Val Arg Gly His Ile Thr Lys Leu Arg Ala Val Leu Tyr Val Ala
            100                 105                 110

Ala Gln Leu Leu Ala Ser Ser Ala Ala Cys Val Leu Leu Arg Phe Leu
        115                 120                 125

Ser Gly Gly Met Val Thr Pro Val His Ala Leu Gly Arg Gly Ile Ser
    130                 135                 140

Pro Met Gln Gly Leu Val Met Glu Val Ile Leu Thr Phe Ser Leu Leu
145                 150                 155                 160

Phe Val Thr Tyr Ala Met Ile Leu Asp Pro Arg Ser Gln Val Arg Ala
                165                 170                 175

Ile Gly Pro Leu Leu Thr Gly Leu Ile Val Gly Ala Asn Ser Leu Ala
            180                 185                 190

Gly Gly Asn Phe Thr Gly Ala Ser Met Asn Pro Ala Arg Ser Phe Gly
        195                 200                 205

Pro Ala Leu Ala Thr Gly Asp Trp Thr Asn His Trp Val Tyr Trp Ile
    210                 215                 220

Gly Pro Leu Leu Gly Gly Pro Leu Ala Gly Phe Val Tyr Glu Ser Leu
225                 230                 235                 240

Phe Leu Val Gln Lys Met His Glu Ala Ala Ala Gln Trp Gly Ser Leu
                245                 250                 255

Thr Thr Ile Ser Pro Cys Val Val Ala His Ala Ser Cys Leu Phe Leu
            260                 265                 270


<210> SEQ ID NO 27
<211> LENGTH: 1302
<212> TYPE: DNA
<213> ORGANISM: Zea mays
<220> FEATURE:
<221> NAME/KEY: CDS
<222> LOCATION: (152)...(923)

<400> SEQUENCE: 27

cccgggtcga cccacgcgtc cgcaaaatat ctccctgcgc ttttccgagt ccttttccct     60

ccaaggaaca gaaacaaccg gagcttttac ccacccgct ttcccctccc cgccaggaac     120

aacagggctc ctcgcaataa ttcatccatc c atg gcg aag ctc gtg aac aag      172
                                   Met Ala Lys Leu Val Asn Lys
                                   1               5

ctg gtc gat tcg ttc gac cac gat gag gcg cca gcg ccg gac gtc ggc      220
Leu Val Asp Ser Phe Asp His Asp Glu Ala Pro Ala Pro Asp Val Gly
        10                  15                  20

tgc gtg cgc gcc gtg ctg gct gag ctc gtc ctc acc ttc ctc ttc gtc      268
Cys Val Arg Ala Val Leu Ala Glu Leu Val Leu Thr Phe Leu Phe Val
    25                  30                  35

ttc acc ggc gtc tcc gcc tcc atg gcc gcc ggg gcc ggc ggg aag ccc      316
Phe Thr Gly Val Ser Ala Ser Met Ala Ala Gly Ala Gly Gly Lys Pro
40                  45                  50                  55

ggg gag gct atg ccg atg gcg acg ctg gcg gcg gtg gct atc gcg cac      364
Gly Glu Ala Met Pro Met Ala Thr Leu Ala Ala Val Ala Ile Ala His
                60                  65                  70

gcg ctg gcc gct ggc gtc ctg gtg acg gcc ggc ttc cac gtc tcc ggc      412
Ala Leu Ala Ala Gly Val Leu Val Thr Ala Gly Phe His Val Ser Gly
            75                  80                  85
```

-continued

```
ggc cac ctc aac ccc gcg gtg acg gtg ggg atc ttg gtt cgc ggc cac      460
Gly His Leu Asn Pro Ala Val Thr Val Gly Ile Leu Val Arg Gly His
         90                  95                 100

atc acc aag ctc cgg gcg ctg ctg tac gtc gcc gcc cag ctg ctg gcg      508
Ile Thr Lys Leu Arg Ala Leu Leu Tyr Val Ala Ala Gln Leu Leu Ala
    105                 110                 115

tcc tcc ctc gcc tgc atc ctc ctc cgc tac ctc agc ggc ggc atg gtg      556
Ser Ser Leu Ala Cys Ile Leu Leu Arg Tyr Leu Ser Gly Gly Met Val
120                 125                 130                 135

acc ccg gtg cac gcc ctg ggc gct ggc atc agg ccg atg cag ggc ctg      604
Thr Pro Val His Ala Leu Gly Ala Gly Ile Arg Pro Met Gln Gly Leu
                140                 145                 150

gtg atg gag gtg atc ctc acc ttc tcg ctg ctc ttc gtc acc tac gcc      652
Val Met Glu Val Ile Leu Thr Phe Ser Leu Leu Phe Val Thr Tyr Ala
            155                 160                 165

atg atc ctg gac ccg cgg agc cag gtc cgc acc atc ggc ccg ctg ctg      700
Met Ile Leu Asp Pro Arg Ser Gln Val Arg Thr Ile Gly Pro Leu Leu
        170                 175                 180

acg ggg ctc ata gtc ggc gcc aac agc ctc gcc ggc ggc aac ttc acc      748
Thr Gly Leu Ile Val Gly Ala Asn Ser Leu Ala Gly Gly Asn Phe Thr
    185                 190                 195

ggc gcg tcc atg aac ccg gcg cgg tcc ttc ggt ccc gcc atg gcc acc      796
Gly Ala Ser Met Asn Pro Ala Arg Ser Phe Gly Pro Ala Met Ala Thr
200                 205                 210                 215

ggg gtc tgg acc aac cac tgg gtc tac tgg atc ggc ccg ctg ctc ggc      844
Gly Val Trp Thr Asn His Trp Val Tyr Trp Ile Gly Pro Leu Leu Gly
                220                 225                 230

ggg tcc ctg gcc ggc ttc gtg tac gag tcg ctg ttc atg gtg aac aag      892
Gly Ser Leu Ala Gly Phe Val Tyr Glu Ser Leu Phe Met Val Asn Lys
            235                 240                 245

acg cac gag ccg ctg ctc aat gga gac atc t gacgaccgtc gggcccccag      943
Thr His Glu Pro Leu Leu Asn Gly Asp Ile
        250                 255

ggcagtgagc acggttcatg cttgttttct gtaaaatagt tcgttaccta caagcatgat   1003

gcatatattg accaaggtaa ttaattagag agggttgctg ttaaatagtt accctggtgg   1063

gattgtggga tgtagaaatt gttgctgggc tttgcttttc tttttctttt ttacttttcc   1123

tcccaaggaa ttttttaaga gggttgggtt ctgtaaagga tttgtttagg ctattagtta   1183

gctatgtagt agaaaactag agaatgctat acgttggacg tgattttttt cacgtatatt   1243

gttgtacgat atggtatttt ttatcttccg gatgaaaaaa aaaaaaaaaa gggcggccg    1302


<210> SEQ ID NO 28
<211> LENGTH: 257
<212> TYPE: PRT
<213> ORGANISM: Zea mays

<400> SEQUENCE: 28

Met Ala Lys Leu Val Asn Lys Leu Val Asp Ser Phe Asp His Asp Glu
 1               5                  10                  15

Ala Pro Ala Pro Asp Val Gly Cys Val Arg Ala Val Leu Ala Glu Leu
            20                  25                  30

Val Leu Thr Phe Leu Phe Val Phe Thr Gly Val Ser Ala Ser Met Ala
        35                  40                  45

Ala Gly Ala Gly Gly Lys Pro Gly Glu Ala Met Pro Met Ala Thr Leu
    50                  55                  60

Ala Ala Val Ala Ile Ala His Ala Leu Ala Ala Gly Val Leu Val Thr
65                  70                  75                  80
```

-continued

```
Ala Gly Phe His Val Ser Gly Gly His Leu Asn Pro Ala Val Thr Val
                85                  90                  95

Gly Ile Leu Val Arg Gly His Ile Thr Lys Leu Arg Ala Leu Leu Tyr
            100                 105                 110

Val Ala Ala Gln Leu Leu Ala Ser Ser Leu Ala Cys Ile Leu Leu Arg
        115                 120                 125

Tyr Leu Ser Gly Gly Met Val Thr Pro Val His Ala Leu Gly Ala Gly
    130                 135                 140

Ile Arg Pro Met Gln Gly Leu Val Met Glu Val Ile Leu Thr Phe Ser
145                 150                 155                 160

Leu Leu Phe Val Thr Tyr Ala Met Ile Leu Asp Pro Arg Ser Gln Val
                165                 170                 175

Arg Thr Ile Gly Pro Leu Leu Thr Gly Leu Ile Val Gly Ala Asn Ser
            180                 185                 190

Leu Ala Gly Gly Asn Phe Thr Gly Ala Ser Met Asn Pro Ala Arg Ser
        195                 200                 205

Phe Gly Pro Ala Met Ala Thr Gly Val Trp Thr Asn His Trp Val Tyr
    210                 215                 220

Trp Ile Gly Pro Leu Leu Gly Gly Ser Leu Ala Gly Phe Val Tyr Glu
225                 230                 235                 240

Ser Leu Phe Met Val Asn Lys Thr His Glu Pro Leu Leu Asn Gly Asp
                245                 250                 255

Ile


<210> SEQ ID NO 29
<211> LENGTH: 1087
<212> TYPE: DNA
<213> ORGANISM: Zea mays
<220> FEATURE:
<221> NAME/KEY: CDS
<222> LOCATION: (125)...(872)

<400> SEQUENCE: 29

gaattcggca cgagcagtca cacagcgttg cgcgagagag cttattgcaa attactctgt     60

ggaccgaacc ggtcggtcgg aagtcggaac aataagcagc agatagagag agagagagag    120

agag atg ggg aag ctg acg ctg ggg cac cgc ggc gag gcg tca gag ccg     169
     Met Gly Lys Leu Thr Leu Gly His Arg Gly Glu Ala Ser Glu Pro
      1               5                  10                  15

gac ttc ttc agg ggc gtc ctc ggc gag ctc gtc ctc acc ttc ctc ttc      217
Asp Phe Phe Arg Gly Val Leu Gly Glu Leu Val Leu Thr Phe Leu Phe
                 20                  25                  30

gtc ttc atc ggc gtc gga gcc gcc atg acc gac gga gcg acg acg aag      265
Val Phe Ile Gly Val Gly Ala Ala Met Thr Asp Gly Ala Thr Thr Lys
             35                  40                  45

ggt agc acc gct gga ggc gac ctg acg gcg gtg gcg ttg ggg cag gcg      313
Gly Ser Thr Ala Gly Gly Asp Leu Thr Ala Val Ala Leu Gly Gln Ala
         50                  55                  60

ctg gtg gtg gcg gtg atc gcg acg gcg ggg ttc cac atc tcc ggc ggc      361
Leu Val Val Ala Val Ile Ala Thr Ala Gly Phe His Ile Ser Gly Gly
     65                  70                  75

cac gtc aac ccg gcc gtg acg ctg tcg ctg gcc gtc ggc ggg cac gtc      409
His Val Asn Pro Ala Val Thr Leu Ser Leu Ala Val Gly Gly His Val
 80                  85                  90                  95

acg ctg ttc cgc tcc tcc ctg tac atc gcc gcc cag atg ctc gcc tcc      457
Thr Leu Phe Arg Ser Ser Leu Tyr Ile Ala Ala Gln Met Leu Ala Ser
                100                 105                 110

tcc gcg gcc tgc ttc ctg ctc agg tgg ctc acg ggc ggg ctg gcc acg      505
```

-continued

```
Ser Ala Ala Cys Phe Leu Leu Arg Trp Leu Thr Gly Gly Leu Ala Thr
            115                 120                 125

ccg gtg cac gcg ctg gcg gag ggc gtg ggc ccg ctg cag ggc gtg gtg      553
Pro Val His Ala Leu Ala Glu Gly Val Gly Pro Leu Gln Gly Val Val
        130                 135                 140

gcg gag gcc gtc ttc acc ttc agc ctg ctc ttc gtc atc tac gcc acc      601
Ala Glu Ala Val Phe Thr Phe Ser Leu Leu Phe Val Ile Tyr Ala Thr
    145                 150                 155

atc ctg gac ccg cgg aag ctg ctc ccg ggc gcc ggc ccg ctg ctc acc      649
Ile Leu Asp Pro Arg Lys Leu Leu Pro Gly Ala Gly Pro Leu Leu Thr
160                 165                 170                 175

ggc ctc ctc gtc ggg gcc aac tcc gtc gcc ggc gcc gcc ctg tcc ggc      697
Gly Leu Leu Val Gly Ala Asn Ser Val Ala Gly Ala Ala Leu Ser Gly
                180                 185                 190

gcc tcc atg aac ccg gcc agg tcc ttc ggg ccc gcc gtc gcc tcg ggc      745
Ala Ser Met Asn Pro Ala Arg Ser Phe Gly Pro Ala Val Ala Ser Gly
            195                 200                 205

gtc tgg acg cac cac tgg gtg tac tgg gtt ggc ccg ctc gcc gga ggc      793
Val Trp Thr His His Trp Val Tyr Trp Val Gly Pro Leu Ala Gly Gly
        210                 215                 220

ccg ctc gcc gtg ctc gtc tac gag tgc tgc ttc atg gcg gcc gct ccc      841
Pro Leu Ala Val Leu Val Tyr Glu Cys Cys Phe Met Ala Ala Ala Pro
    225                 230                 235

acg cac gac ctt ctg ccc cag cag gac cca t gatcagcgtg catcgtgcgt      892
Thr His Asp Leu Leu Pro Gln Gln Asp Pro
240                 245

tggatcgatc ggagtgtgac ttggtttgag ctggcgacgg attgtgtttg attcgtgtgt    952

gtgcagtgtg tgcacagttg caaacgactt atgggttgtt tttacctcat gttttccttt   1012

gtttgagaag gctacttctc aagaacaaaa ctgcagaatt tcttgtgggt ctaaaaaaaa   1072

aaaaaaaaaa ctcga                                                    1087


<210> SEQ ID NO 30
<211> LENGTH: 249
<212> TYPE: PRT
<213> ORGANISM: Zea mays

<400> SEQUENCE: 30

Met Gly Lys Leu Thr Leu Gly His Arg Gly Glu Ala Ser Glu Pro Asp
 1               5                  10                  15

Phe Phe Arg Gly Val Leu Gly Glu Leu Val Leu Thr Phe Leu Phe Val
            20                  25                  30

Phe Ile Gly Val Gly Ala Ala Met Thr Asp Gly Ala Thr Thr Lys Gly
        35                  40                  45

Ser Thr Ala Gly Gly Asp Leu Thr Ala Val Ala Leu Gly Gln Ala Leu
    50                  55                  60

Val Val Ala Val Ile Ala Thr Ala Gly Phe His Ile Ser Gly Gly His
65                  70                  75                  80

Val Asn Pro Ala Val Thr Leu Ser Leu Ala Val Gly Gly His Val Thr
                85                  90                  95

Leu Phe Arg Ser Ser Leu Tyr Ile Ala Ala Gln Met Leu Ala Ser Ser
            100                 105                 110

Ala Ala Cys Phe Leu Leu Arg Trp Leu Thr Gly Gly Leu Ala Thr Pro
        115                 120                 125

Val His Ala Leu Ala Glu Gly Val Gly Pro Leu Gln Gly Val Val Ala
    130                 135                 140

Glu Ala Val Phe Thr Phe Ser Leu Leu Phe Val Ile Tyr Ala Thr Ile
```

-continued

```
145                 150                 155                 160

Leu Asp Pro Arg Lys Leu Leu Pro Gly Ala Gly Pro Leu Leu Thr Gly
                165                 170                 175

Leu Leu Val Gly Ala Asn Ser Val Ala Gly Ala Ala Leu Ser Gly Ala
            180                 185                 190

Ser Met Asn Pro Ala Arg Ser Phe Gly Pro Ala Val Ala Ser Gly Val
        195                 200                 205

Trp Thr His His Trp Val Tyr Trp Val Gly Pro Leu Ala Gly Gly Pro
    210                 215                 220

Leu Ala Val Leu Val Tyr Glu Cys Cys Phe Met Ala Ala Ala Pro Thr
225                 230                 235                 240

His Asp Leu Leu Pro Gln Gln Asp Pro
                245


<210> SEQ ID NO 31
<211> LENGTH: 1015
<212> TYPE: DNA
<213> ORGANISM: Zea mays
<220> FEATURE:
<221> NAME/KEY: CDS
<222> LOCATION: (77)...(863)

<400> SEQUENCE: 31

gaattcggca cgaggctact gcaagctact ccgtctccgt agctaaagga gaggtaggtt      60

tttatttggc gacgac atg agc acg ggc gtg cga ccg ggg cgg cgg ttc acg     112
                  Met Ser Thr Gly Val Arg Pro Gly Arg Arg Phe Thr
                   1               5                  10

gtg ggg cgg agc gag gac gcc acg cac ccg gac acc atc cgc gcc gcc       160
Val Gly Arg Ser Glu Asp Ala Thr His Pro Asp Thr Ile Arg Ala Ala
         15                  20                  25

atc tcc gag ttc atc gcc acc gcc atc ttc gtc ttc gcc gcc gag gga       208
Ile Ser Glu Phe Ile Ala Thr Ala Ile Phe Val Phe Ala Ala Glu Gly
     30                  35                  40

tcc gtc ctc tcg ctc ggg aag atg tac cac gac atg agc acg gcg ggc       256
Ser Val Leu Ser Leu Gly Lys Met Tyr His Asp Met Ser Thr Ala Gly
 45                  50                  55                  60

ggc ctg gtg gct gtg gcg ctg gcg cac gcg ctg gcc ctg gcc gtg gcc       304
Gly Leu Val Ala Val Ala Leu Ala His Ala Leu Ala Leu Ala Val Ala
                 65                  70                  75

gtg gca gtg gcc gtc aac atc tcg ggc ggg cac gtg aac ccg gcg gtc       352
Val Ala Val Ala Val Asn Ile Ser Gly Gly His Val Asn Pro Ala Val
             80                  85                  90

acc ttc ggc gcg ctc gtc ggc ggc cgc gtc tcc ctc gtc cgc gcg gtc       400
Thr Phe Gly Ala Leu Val Gly Gly Arg Val Ser Leu Val Arg Ala Val
         95                 100                 105

ttg tac tgg gtc gcg cag ctg ctg ggc gcc gtc gcc gcc acg ctg ctc       448
Leu Tyr Trp Val Ala Gln Leu Leu Gly Ala Val Ala Ala Thr Leu Leu
    110                 115                 120

ctg cgg ctc gcc acg ggg ggc atg cgg ccg ccg ggg ttc gcg ctc gcg       496
Leu Arg Leu Ala Thr Gly Gly Met Arg Pro Pro Gly Phe Ala Leu Ala
125                 130                 135                 140

tcc ggg gtc ggg gac tgg cac gcc gtg ctg ctg gag gcc gtc atg acg       544
Ser Gly Val Gly Asp Trp His Ala Val Leu Leu Glu Ala Val Met Thr
                145                 150                 155

ttc ggc ctc atg tac gcc tac tac gcc acg gtg atc gac ccg aag cgg       592
Phe Gly Leu Met Tyr Ala Tyr Tyr Ala Thr Val Ile Asp Pro Lys Arg
            160                 165                 170

ggg cac gtg ggc acc atc gcg ccg ctg gcc gtg ggc ttc ctg ctc ggc       640
Gly His Val Gly Thr Ile Ala Pro Leu Ala Val Gly Phe Leu Leu Gly
```

-continued

```
        175                 180                 185

gcc aac gtg ctg gcg gga ggg ccc ttc gac ggc gca ggg atg aac ccg      688
Ala Asn Val Leu Ala Gly Gly Pro Phe Asp Gly Ala Gly Met Asn Pro
    190                 195                 200

gcg cgg gtc ttc ggc ccg gcg ctc gtc ggg tgg cgg tgg agg cac cac      736
Ala Arg Val Phe Gly Pro Ala Leu Val Gly Trp Arg Trp Arg His His
205                 210                 215                 220

tgg gtg tac tgg ctg ggc cct ttc ctc ggc gcc ggg ctt gca ggg ctg      784
Trp Val Tyr Trp Leu Gly Pro Phe Leu Gly Ala Gly Leu Ala Gly Leu
                225                 230                 235

gtg tac gag tac ctg gtt atc ccg tcc gcc gac gcc gcc gtg ccc cac      832
Val Tyr Glu Tyr Leu Val Ile Pro Ser Ala Asp Ala Ala Val Pro His
            240                 245                 250

gcg cac cag ccg ctc gcg cca gag gac tac t agcttgaaaa ttgtattgtg      883
Ala His Gln Pro Leu Ala Pro Glu Asp Tyr
        255                 260

gggtcgtgta agtggttaat aagggggggca taggtacgta cttgtctgtc gccccagcgt    943

gtgttggaga cggtgaatca ggtgatgtgt acatgctgct tcactgtagt gtatgtgtat   1003

gtgtatgtag ta                                                      1015


<210> SEQ ID NO 32
<211> LENGTH: 262
<212> TYPE: PRT
<213> ORGANISM: Zea mays

<400> SEQUENCE: 32

Met Ser Thr Gly Val Arg Pro Gly Arg Arg Phe Thr Val Gly Arg Ser
 1               5                  10                  15

Glu Asp Ala Thr His Pro Asp Thr Ile Arg Ala Ala Ile Ser Glu Phe
            20                  25                  30

Ile Ala Thr Ala Ile Phe Val Phe Ala Ala Glu Gly Ser Val Leu Ser
        35                  40                  45

Leu Gly Lys Met Tyr His Asp Met Ser Thr Ala Gly Gly Leu Val Ala
    50                  55                  60

Val Ala Leu Ala His Ala Leu Ala Leu Ala Val Ala Val Ala Val Ala
65                  70                  75                  80

Val Asn Ile Ser Gly Gly His Val Asn Pro Ala Val Thr Phe Gly Ala
                85                  90                  95

Leu Val Gly Gly Arg Val Ser Leu Val Arg Ala Val Leu Tyr Trp Val
            100                 105                 110

Ala Gln Leu Leu Gly Ala Val Ala Ala Thr Leu Leu Leu Arg Leu Ala
        115                 120                 125

Thr Gly Gly Met Arg Pro Pro Gly Phe Ala Leu Ala Ser Gly Val Gly
    130                 135                 140

Asp Trp His Ala Val Leu Leu Glu Ala Val Met Thr Phe Gly Leu Met
145                 150                 155                 160

Tyr Ala Tyr Tyr Ala Thr Val Ile Asp Pro Lys Arg Gly His Val Gly
                165                 170                 175

Thr Ile Ala Pro Leu Ala Val Gly Phe Leu Leu Gly Ala Asn Val Leu
            180                 185                 190

Ala Gly Gly Pro Phe Asp Gly Ala Gly Met Asn Pro Ala Arg Val Phe
        195                 200                 205

Gly Pro Ala Leu Val Gly Trp Arg Trp Arg His His Trp Val Tyr Trp
    210                 215                 220

Leu Gly Pro Phe Leu Gly Ala Gly Leu Ala Gly Leu Val Tyr Glu Tyr
```

-continued

```
225                 230                 235                 240

Leu Val Ile Pro Ser Ala Asp Ala Ala Val Pro His Ala His Gln Pro
                245                 250                 255

Leu Ala Pro Glu Asp Tyr
            260


<210> SEQ ID NO 33
<211> LENGTH: 1081
<212> TYPE: DNA
<213> ORGANISM: Zea mays
<220> FEATURE:
<221> NAME/KEY: CDS
<222> LOCATION: (37)...(799)

<400> SEQUENCE: 33

cccgggtcga cccacgcgtc cggacgagac aagaga atg cct gtg agc agg atc       54
                                        Met Pro Val Ser Arg Ile
                                         1               5

gcc gtg ggt gct ccg ggc gag ctg tcc cac ccc gac acc gcc aag gcc      102
Ala Val Gly Ala Pro Gly Glu Leu Ser His Pro Asp Thr Ala Lys Ala
            10                  15                  20

gcc gtc gcc gag ttc atc tcc acg ctc atc ttc gtc ttc gcc ggc tca      150
Ala Val Ala Glu Phe Ile Ser Thr Leu Ile Phe Val Phe Ala Gly Ser
        25                  30                  35

gga tcg ggg atg gcc ttc agt aag ctc acg gac ggt ggc gcc gcc act      198
Gly Ser Gly Met Ala Phe Ser Lys Leu Thr Asp Gly Gly Ala Ala Thr
    40                  45                  50

cct gcc ggc ctc atc gcc gcg tct ctg gcg cac gcc ctc gcc ctc ttc      246
Pro Ala Gly Leu Ile Ala Ala Ser Leu Ala His Ala Leu Ala Leu Phe
 55                  60                  65                  70

gtg gcc gtc tcc gtg ggt gcc aac atc tcc ggc ggc cac gtg aac cct      294
Val Ala Val Ser Val Gly Ala Asn Ile Ser Gly Gly His Val Asn Pro
                75                  80                  85

gcc gtg acc ttc ggc gcc ttt gtg ggc ggc aac atc agc ctc ctc aag      342
Ala Val Thr Phe Gly Ala Phe Val Gly Gly Asn Ile Ser Leu Leu Lys
            90                  95                 100

gcc ctg gtc tac tgg gtg gcc cag ctc ctg ggc tcc gtc gtc gcc tgc      390
Ala Leu Val Tyr Trp Val Ala Gln Leu Leu Gly Ser Val Val Ala Cys
        105                 110                 115

ctc ctc ctc aag atc gcc acg ggc ggc gcg gcc ctt ggc gcc ttc tcg      438
Leu Leu Leu Lys Ile Ala Thr Gly Gly Ala Ala Leu Gly Ala Phe Ser
    120                 125                 130

ctg tcg gcg ggc gtc ggc gcc atg aac gcc gtg gtg ctg gag atg gtc      486
Leu Ser Ala Gly Val Gly Ala Met Asn Ala Val Val Leu Glu Met Val
135                 140                 145                 150

atg acc ttc ggc ctc gtg tac acg gtg tac gcc acg gcc gtg gac ccc      534
Met Thr Phe Gly Leu Val Tyr Thr Val Tyr Ala Thr Ala Val Asp Pro
                155                 160                 165

aag aag ggc gac ctc ggc gtc atc gcg ccc atc gcc atc ggc ttc atc      582
Lys Lys Gly Asp Leu Gly Val Ile Ala Pro Ile Ala Ile Gly Phe Ile
            170                 175                 180

gtc ggc gcc aac atc ctg gcg ggg ggc gcc ttc gac ggc gcc tcc atg      630
Val Gly Ala Asn Ile Leu Ala Gly Gly Ala Phe Asp Gly Ala Ser Met
        185                 190                 195

aac ccc gcc gtc tcc ttc ggc ccg gcc gtc gtc acc ggc gtc tgg gag      678
Asn Pro Ala Val Ser Phe Gly Pro Ala Val Val Thr Gly Val Trp Glu
    200                 205                 210

aac cac tgg gtg tac tgg gtc ggc cca ctc gcg ggc gcg gcc atc gcg      726
Asn His Trp Val Tyr Trp Val Gly Pro Leu Ala Gly Ala Ala Ile Ala
215                 220                 225                 230
```

-continued

```
gcg ctc gtc tac gac atc atc ttc atc ggg cag cgc cca cac cag cag      774
Ala Leu Val Tyr Asp Ile Ile Phe Ile Gly Gln Arg Pro His Gln Gln
                235                 240                 245

ctg cca acc acg gca gca gac tac t gatgaccatc atcatcatgc              819
Leu Pro Thr Thr Ala Ala Asp Tyr
            250

actgaataat taagaccaga ccactcaata tatatacata tgaagaataa catgccaaat    879

ctcatctcct agagctagca acttgattct ccatatattt cttaaataca aactaaactc    939

gattgagtat agcttggtat gaaaccacat gtgtgtgatg ttattttgtc cttgtggtaa    999

tttgtacatc tctatctcta ccatattaaa gcatcaattt cgacaaaaaa aaaaaataaa   1059

aaaaaaaaaa aaagggcggc cg                                            1081


<210> SEQ ID NO 34
<211> LENGTH: 254
<212> TYPE: PRT
<213> ORGANISM: Zea mays

<400> SEQUENCE: 34

Met Pro Val Ser Arg Ile Ala Val Gly Ala Pro Gly Glu Leu Ser His
 1               5                  10                  15

Pro Asp Thr Ala Lys Ala Ala Val Ala Glu Phe Ile Ser Thr Leu Ile
            20                  25                  30

Phe Val Phe Ala Gly Ser Gly Ser Gly Met Ala Phe Ser Lys Leu Thr
        35                  40                  45

Asp Gly Gly Ala Ala Thr Pro Ala Gly Leu Ile Ala Ala Ser Leu Ala
    50                  55                  60

His Ala Leu Ala Leu Phe Val Ala Val Ser Val Gly Ala Asn Ile Ser
65                  70                  75                  80

Gly Gly His Val Asn Pro Ala Val Thr Phe Gly Ala Phe Val Gly Gly
                85                  90                  95

Asn Ile Ser Leu Leu Lys Ala Leu Val Tyr Trp Val Ala Gln Leu Leu
            100                 105                 110

Gly Ser Val Val Ala Cys Leu Leu Leu Lys Ile Ala Thr Gly Gly Ala
        115                 120                 125

Ala Leu Gly Ala Phe Ser Leu Ser Ala Gly Val Gly Ala Met Asn Ala
    130                 135                 140

Val Val Leu Glu Met Val Met Thr Phe Gly Leu Val Tyr Thr Val Tyr
145                 150                 155                 160

Ala Thr Ala Val Asp Pro Lys Lys Gly Asp Leu Gly Val Ile Ala Pro
                165                 170                 175

Ile Ala Ile Gly Phe Ile Val Gly Ala Asn Ile Leu Ala Gly Gly Ala
            180                 185                 190

Phe Asp Gly Ala Ser Met Asn Pro Ala Val Ser Phe Gly Pro Ala Val
        195                 200                 205

Val Thr Gly Val Trp Glu Asn His Trp Val Tyr Trp Val Gly Pro Leu
    210                 215                 220

Ala Gly Ala Ala Ile Ala Ala Leu Val Tyr Asp Ile Ile Phe Ile Gly
225                 230                 235                 240

Gln Arg Pro His Gln Gln Leu Pro Thr Thr Ala Ala Asp Tyr
                245                 250


<210> SEQ ID NO 35
<211> LENGTH: 442
<212> TYPE: DNA
<213> ORGANISM: Zea mays
```

-continued

```
<220> FEATURE:
<221> NAME/KEY: CDS
<222> LOCATION: (2)...(257)

<400> SEQUENCE: 35

c ccg ggt cga ccc acg cgt ccg cgg acg cgt ggg tca acc tcc atc gtc      49
  Pro Gly Arg Pro Thr Arg Pro Arg Thr Arg Gly Ser Thr Ser Ile Val
   1               5                  10                  15

tcc gtc atc ctc gca ggc gca gag tac acg ggg ccg tct atg aac cca        97
Ser Val Ile Leu Ala Gly Ala Glu Tyr Thr Gly Pro Ser Met Asn Pro
            20                  25                  30

gct aat gca ttt ggc tgg gca tat gtt aac aat tgg cac aac aca tgg       145
Ala Asn Ala Phe Gly Trp Ala Tyr Val Asn Asn Trp His Asn Thr Trp
        35                  40                  45

gag cag ctg tat gtg tac tgg ata tgc ccc ttt att ggg gcc atg ctt       193
Glu Gln Leu Tyr Val Tyr Trp Ile Cys Pro Phe Ile Gly Ala Met Leu
    50                  55                  60

gct gga tgg ata ttt agg gtg gtg ttc cta cca ccg gca cct aag ccc       241
Ala Gly Trp Ile Phe Arg Val Val Phe Leu Pro Pro Ala Pro Lys Pro
 65                  70                  75                  80

aag acc aag aaa gca t gattactcgt ttatggatgc tggtttagaa gaaataagaa    297
Lys Thr Lys Lys Ala
                85

atagaggaag gtcacataag ctcatgtgtt gtacttgatt tcctcaactt cccacatact    357

gggtgttgtg ctctgttact tatttctcat caataattta tgtttacttg taaaaaaaaa    417

aaaaaaaaaa aaaaaagggc ggccg                                          442


<210> SEQ ID NO 36
<211> LENGTH: 85
<212> TYPE: PRT
<213> ORGANISM: Zea mays

<400> SEQUENCE: 36

Pro Gly Arg Pro Thr Arg Pro Arg Thr Arg Gly Ser Thr Ser Ile Val
 1               5                  10                  15

Ser Val Ile Leu Ala Gly Ala Glu Tyr Thr Gly Pro Ser Met Asn Pro
            20                  25                  30

Ala Asn Ala Phe Gly Trp Ala Tyr Val Asn Asn Trp His Asn Thr Trp
        35                  40                  45

Glu Gln Leu Tyr Val Tyr Trp Ile Cys Pro Phe Ile Gly Ala Met Leu
    50                  55                  60

Ala Gly Trp Ile Phe Arg Val Val Phe Leu Pro Pro Ala Pro Lys Pro
65                  70                  75                  80

Lys Thr Lys Lys Ala
                85


<210> SEQ ID NO 37
<211> LENGTH: 1375
<212> TYPE: DNA
<213> ORGANISM: Zea mays
<220> FEATURE:
<221> NAME/KEY: CDS
<222> LOCATION: (215)...(1100)

<400> SEQUENCE: 37

cccgggtcga cccacgcgtc cgcaggtaat acatacctgc gactgcgacg agtgagtaaa     60

gcttcatctt cttcctcctt cctccggcct cttcctgagt gctgcacgca gtgcgtagga    120

aggaactcgc gtacgtacgt gtgctagcta gctagctcga ccacgcgcag cacgcaggcg    180
```

-continued

```
cgtagtagct cgatcgatcg accgccggcc ggaa atg tcg acc aac tcg agg tcc     235
                                      Met Ser Thr Asn Ser Arg Ser
                                       1               5

aac tcc agg gcc aac ttc aac aac gag atc cat gac atc ggc acg gcg       283
Asn Ser Arg Ala Asn Phe Asn Asn Glu Ile His Asp Ile Gly Thr Ala
        10                  15                  20

cag aac tcc agc atg ccc ccc acg tac tac gac cgg tcg ctg gcg gac       331
Gln Asn Ser Ser Met Pro Pro Thr Tyr Tyr Asp Arg Ser Leu Ala Asp
    25                  30                  35

atc ttc cct ccg cac ctc ctc aag aag gtg gtc tcg gag gtg gtg tcc       379
Ile Phe Pro Pro His Leu Leu Lys Lys Val Val Ser Glu Val Val Ser
 40                  45                  50                  55

acg ttc ctg ctg gtg ttc gtc acg tgc ggg gcg gcg ggg atc tac ggc       427
Thr Phe Leu Leu Val Phe Val Thr Cys Gly Ala Ala Gly Ile Tyr Gly
                60                  65                  70

agc gac aag gac cgc atc tcg cag ctg ggg cag tcg gtc gcc ggc ggg       475
Ser Asp Lys Asp Arg Ile Ser Gln Leu Gly Gln Ser Val Ala Gly Gly
            75                  80                  85

ctc atc gtc acc gtc atg atc tac gcc gtc gga cac atc tcg ggc gcg       523
Leu Ile Val Thr Val Met Ile Tyr Ala Val Gly His Ile Ser Gly Ala
        90                  95                  100

cac atg aac ccc gcc gtc acg ctc gcg ttc gcc gtg ttc cgc cat ttc       571
His Met Asn Pro Ala Val Thr Leu Ala Phe Ala Val Phe Arg His Phe
    105                 110                 115

ccc tgg atc cag gtc ccg ttc tac tgg gcg gcg cag ttc acc ggc agc       619
Pro Trp Ile Gln Val Pro Phe Tyr Trp Ala Ala Gln Phe Thr Gly Ser
120                 125                 130                 135

atc tgc gcg tcg ttc gtg ctc aag gcc gtg ctg cac ccc atc gcc gtg       667
Ile Cys Ala Ser Phe Val Leu Lys Ala Val Leu His Pro Ile Ala Val
                140                 145                 150

ctg ggc acc acc acg ccg acg ggg ccg cac tgg cac tcg ctc gtc atc       715
Leu Gly Thr Thr Thr Pro Thr Gly Pro His Trp His Ser Leu Val Ile
            155                 160                 165

gag atc atc gtc acc ttc aac atg atg ttc gtc acc ctc gcc gtc gcc       763
Glu Ile Ile Val Thr Phe Asn Met Met Phe Val Thr Leu Ala Val Ala
        170                 175                 180

acg gac acg aga gcg gtg ggt gag ttg gcg ggg ttg gca gtt ggt tcc       811
Thr Asp Thr Arg Ala Val Gly Glu Leu Ala Gly Leu Ala Val Gly Ser
    185                 190                 195

gcg gtt tgc att acg tcc atc ttc gca ggg gca gtg tcg ggc gga tcg       859
Ala Val Cys Ile Thr Ser Ile Phe Ala Gly Ala Val Ser Gly Gly Ser
200                 205                 210                 215

atg aac ccg gcg agg acg ctg ggg ccg gcg ctg gcg agc aac ctc tac       907
Met Asn Pro Ala Arg Thr Leu Gly Pro Ala Leu Ala Ser Asn Leu Tyr
                220                 225                 230

acc ggc ctc tgg atc tac ttc ctg ggc ccc gtc ctc ggc acg ctc tcc       955
Thr Gly Leu Trp Ile Tyr Phe Leu Gly Pro Val Leu Gly Thr Leu Ser
            235                 240                 245

ggg gcc tgg acc tac acc tac atc cgc ttc gag gag gcg ccc agc cac      1003
Gly Ala Trp Thr Tyr Thr Tyr Ile Arg Phe Glu Glu Ala Pro Ser His
        250                 255                 260

aag gac atg tcg cag aag ctc tcc tcc ttc aag ctc cgc cgc ctg cag      1051
Lys Asp Met Ser Gln Lys Leu Ser Ser Phe Lys Leu Arg Arg Leu Gln
    265                 270                 275

agc cag tcc gtc gcg gtc gac gac gac gag ctc gac cac atc caa gtg      1099
Ser Gln Ser Val Ala Val Asp Asp Asp Glu Leu Asp His Ile Gln Val
280                 285                 290                 295

t gattcatgct ccatcgatca gagagtgcgc acttgtttac tcctcagtcc             1150

tctcactcta tgtatcggca acactcccta ggatatacta gtggtccgta gtcatggtct   1210
```

```
atgtctatgt gtcgctcttc tctcgatcca tgcacgtccg tggcgcggtg tggatgggct   1270

cgctctgtca aatgtgccaa tgagctggag cttaattttg ggacgaaaaa aaaaaaaaaa   1330

aaaaaaaaaa aaaaaaaaaa aaaaaaaaaa aaaaaagggc ggccg                   1375
```

```
<210> SEQ ID NO 38
<211> LENGTH: 295
<212> TYPE: PRT
<213> ORGANISM: Zea mays

<400> SEQUENCE: 38

Met Ser Thr Asn Ser Arg Ser Asn Ser Arg Ala Asn Phe Asn Asn Glu
 1               5                  10                  15

Ile His Asp Ile Gly Thr Ala Gln Asn Ser Ser Met Pro Pro Thr Tyr
            20                  25                  30

Tyr Asp Arg Ser Leu Ala Asp Ile Phe Pro Pro His Leu Leu Lys Lys
        35                  40                  45

Val Val Ser Glu Val Val Ser Thr Phe Leu Leu Val Phe Val Thr Cys
    50                  55                  60

Gly Ala Ala Gly Ile Tyr Gly Ser Asp Lys Asp Arg Ile Ser Gln Leu
65                  70                  75                  80

Gly Gln Ser Val Ala Gly Gly Leu Ile Val Thr Val Met Ile Tyr Ala
                85                  90                  95

Val Gly His Ile Ser Gly Ala His Met Asn Pro Ala Val Thr Leu Ala
            100                 105                 110

Phe Ala Val Phe Arg His Phe Pro Trp Ile Gln Val Pro Phe Tyr Trp
        115                 120                 125

Ala Ala Gln Phe Thr Gly Ser Ile Cys Ala Ser Phe Val Leu Lys Ala
    130                 135                 140

Val Leu His Pro Ile Ala Val Leu Gly Thr Thr Thr Pro Thr Gly Pro
145                 150                 155                 160

His Trp His Ser Leu Val Ile Glu Ile Ile Val Thr Phe Asn Met Met
                165                 170                 175

Phe Val Thr Leu Ala Val Ala Thr Asp Thr Arg Ala Val Gly Glu Leu
            180                 185                 190

Ala Gly Leu Ala Val Gly Ser Ala Val Cys Ile Thr Ser Ile Phe Ala
        195                 200                 205

Gly Ala Val Ser Gly Gly Ser Met Asn Pro Ala Arg Thr Leu Gly Pro
    210                 215                 220

Ala Leu Ala Ser Asn Leu Tyr Thr Gly Leu Trp Ile Tyr Phe Leu Gly
225                 230                 235                 240

Pro Val Leu Gly Thr Leu Ser Gly Ala Trp Thr Tyr Thr Tyr Ile Arg
                245                 250                 255

Phe Glu Glu Ala Pro Ser His Lys Asp Met Ser Gln Lys Leu Ser Ser
            260                 265                 270

Phe Lys Leu Arg Arg Leu Gln Ser Gln Ser Val Ala Val Asp Asp Asp
        275                 280                 285

Glu Leu Asp His Ile Gln Val
    290                 295
```

```
<210> SEQ ID NO 39
<211> LENGTH: 1485
<212> TYPE: DNA
<213> ORGANISM: Zea mays
<220> FEATURE:
<221> NAME/KEY: CDS
```

<222> LOCATION: (133)...(1015)

<400> SEQUENCE: 39

```
cccgggtcga cccacgcgtc cgacagcgag cacgcaccag catccttggc acttggcagc     60

gatctgcttg cttctcccag cgcgcgcggc caagctagta ggggtctagg ggatcgatca    120

gatatccacg cc atg gcc gcc gcc tcc acc acg tcg agg acc aac tcg cgg    171
              Met Ala Ala Ala Ser Thr Thr Ser Arg Thr Asn Ser Arg
                1               5                  10

gtg aac tac tcg aac gag atc cac gac ctc tcc acc gtg cag agc ggc      219
Val Asn Tyr Ser Asn Glu Ile His Asp Leu Ser Thr Val Gln Ser Gly
     15                  20                  25

tcc gtc gtc ccc acc ttg ttc tac ccg gac aag tcc atc gcc gac atc      267
Ser Val Val Pro Thr Leu Phe Tyr Pro Asp Lys Ser Ile Ala Asp Ile
 30                  35                  40                  45

ttc ccg ccg cac ctt ggg aag aag gtg atc tcg gag gtg gtg gcg acg      315
Phe Pro Pro His Leu Gly Lys Lys Val Ile Ser Glu Val Val Ala Thr
                50                  55                  60

ttc ctt ctg gtg ttc gtc acc tgc ggg gcg gcg tcc atc tac ggc gaa      363
Phe Leu Leu Val Phe Val Thr Cys Gly Ala Ala Ser Ile Tyr Gly Glu
            65                  70                  75

gac aac agg cgc atc tcg cag ctg ggg cag tcg gtg gcc ggc ggg ctc      411
Asp Asn Arg Arg Ile Ser Gln Leu Gly Gln Ser Val Ala Gly Gly Leu
        80                  85                  90

atc gtc acc gtc atg atc tac gcc acc ggc cac atc tcc ggc gcg cac      459
Ile Val Thr Val Met Ile Tyr Ala Thr Gly His Ile Ser Gly Ala His
     95                 100                 105

atg aac ccc gcc gtc acg ctc tcc ttc gca tgc ttc cgg cat ttc cca      507
Met Asn Pro Ala Val Thr Leu Ser Phe Ala Cys Phe Arg His Phe Pro
110                 115                 120                 125

tgg att cag gtg ccc ttc tac tgg gcg gcg cag ttc acg ggg gcg atg      555
Trp Ile Gln Val Pro Phe Tyr Trp Ala Ala Gln Phe Thr Gly Ala Met
                130                 135                 140

tgc gcg gcg ttc gtg ctc aag gcg gtg ctc cac ccc atc gcc gtg atc      603
Cys Ala Ala Phe Val Leu Lys Ala Val Leu His Pro Ile Ala Val Ile
            145                 150                 155

ggc acc acc acg ccg tcg ggg ccg cac tgg cac gcg ctc ctc atc gag      651
Gly Thr Thr Thr Pro Ser Gly Pro His Trp His Ala Leu Leu Ile Glu
        160                 165                 170

atc gtc gtc acc ttc aac atg atg ttc gtc acc tgc gcc gtc gcc acc      699
Ile Val Val Thr Phe Asn Met Met Phe Val Thr Cys Ala Val Ala Thr
    175                 180                 185

gac tcc agg gcg gtg ggt gag ttg gca ggg tta gca gtc ggt tcc gcg      747
Asp Ser Arg Ala Val Gly Glu Leu Ala Gly Leu Ala Val Gly Ser Ala
190                 195                 200                 205

gtt tgc att act tcc atc ttc gca ggg ccg gtg tcg ggc gga tcg atg      795
Val Cys Ile Thr Ser Ile Phe Ala Gly Pro Val Ser Gly Gly Ser Met
                210                 215                 220

aac ccg gcg cgg acg ctg gcg ccg gcg gtg gcc agc aac gtc ttc acg      843
Asn Pro Ala Arg Thr Leu Ala Pro Ala Val Ala Ser Asn Val Phe Thr
            225                 230                 235

ggc ctc tgg atc tac ttc ctc ggc ccc gtc atc ggc acg ctc tcc ggg      891
Gly Leu Trp Ile Tyr Phe Leu Gly Pro Val Ile Gly Thr Leu Ser Gly
        240                 245                 250

gcg tgg gtc tac acc tac atc cgc ttc gag gag gcc ccc gcc gcc aag      939
Ala Trp Val Tyr Thr Tyr Ile Arg Phe Glu Glu Ala Pro Ala Ala Lys
    255                 260                 265

gac acg cag agg ctc tcc tcc ttc aag ctc cgc cgc atg cag agc cag      987
Asp Thr Gln Arg Leu Ser Ser Phe Lys Leu Arg Arg Met Gln Ser Gln
270                 275                 280                 285
```

-continued

```
ctc gcc gcc gac gag ttc gac acc gtc t aaattaaaac gcccacacgc        1035
Leu Ala Ala Asp Glu Phe Asp Thr Val
                290

gcatccacaa cactgtcagc ctgcaggtca actcttcgcg cgtacgtacg ctggacgctg   1095

gctgagagag tgagtgagag agagagagag tactgtacta ctgtgtgctc gctcgctcgc   1155

tctgttcaaa gacctcatca tatcaggtgg gagctagaga gatagagctg cgtgtatgta   1215

tgtgtgtgtg tgtacgtgct tggtgtaccc tacctagcgg gtgagagcag ctagcgtgat   1275

gtttatgtat cttcgtcagt gttgcaaaag ttaattgata tgcagctgat gtgtctggct   1335

ttgctggttt gcaaaagatg catgcatgtg ttggaactcg gaacacaaat atatatatgg   1395

gttttttttt gtctaaaaaa aaaaaaaaaa aaaaaaaaaa aaaaaaaaaa aaaaaaaaaa   1455

aaaaaaaaaa aaaaaaaaaa agggcggccg                                    1485


<210> SEQ ID NO 40
<211> LENGTH: 294
<212> TYPE: PRT
<213> ORGANISM: Zea mays

<400> SEQUENCE: 40

Met Ala Ala Ala Ser Thr Thr Ser Arg Thr Asn Ser Arg Val Asn Tyr
 1               5                  10                  15

Ser Asn Glu Ile His Asp Leu Ser Thr Val Gln Ser Gly Ser Val Val
            20                  25                  30

Pro Thr Leu Phe Tyr Pro Asp Lys Ser Ile Ala Asp Ile Phe Pro Pro
        35                  40                  45

His Leu Gly Lys Lys Val Ile Ser Glu Val Val Ala Thr Phe Leu Leu
    50                  55                  60

Val Phe Val Thr Cys Gly Ala Ala Ser Ile Tyr Gly Glu Asp Asn Arg
65                  70                  75                  80

Arg Ile Ser Gln Leu Gly Gln Ser Val Ala Gly Gly Leu Ile Val Thr
                85                  90                  95

Val Met Ile Tyr Ala Thr Gly His Ile Ser Gly Ala His Met Asn Pro
            100                 105                 110

Ala Val Thr Leu Ser Phe Ala Cys Phe Arg His Phe Pro Trp Ile Gln
        115                 120                 125

Val Pro Phe Tyr Trp Ala Ala Gln Phe Thr Gly Ala Met Cys Ala Ala
    130                 135                 140

Phe Val Leu Lys Ala Val Leu His Pro Ile Ala Val Ile Gly Thr Thr
145                 150                 155                 160

Thr Pro Ser Gly Pro His Trp His Ala Leu Leu Ile Glu Ile Val Val
                165                 170                 175

Thr Phe Asn Met Met Phe Val Thr Cys Ala Val Ala Thr Asp Ser Arg
            180                 185                 190

Ala Val Gly Glu Leu Ala Gly Leu Ala Val Gly Ser Ala Val Cys Ile
        195                 200                 205

Thr Ser Ile Phe Ala Gly Pro Val Ser Gly Gly Ser Met Asn Pro Ala
    210                 215                 220

Arg Thr Leu Ala Pro Ala Val Ala Ser Asn Val Phe Thr Gly Leu Trp
225                 230                 235                 240

Ile Tyr Phe Leu Gly Pro Val Ile Gly Thr Leu Ser Gly Ala Trp Val
                245                 250                 255

Tyr Thr Tyr Ile Arg Phe Glu Glu Ala Pro Ala Ala Lys Asp Thr Gln
            260                 265                 270
```

```
Arg Leu Ser Ser Phe Lys Leu Arg Arg Met Gln Ser Gln Leu Ala Ala
        275                 280                 285

Asp Glu Phe Asp Thr Val
    290


<210> SEQ ID NO 41
<211> LENGTH: 1116
<212> TYPE: DNA
<213> ORGANISM: Zea mays
<220> FEATURE:
<221> NAME/KEY: CDS
<222> LOCATION: (2)...(719)

<400> SEQUENCE: 41

c ccg ggt cga ccc acg cgt ccg ggc tgc tgc acg cag ctg ggc gcg gag      49
  Pro Gly Arg Pro Thr Arg Pro Gly Cys Cys Thr Gln Leu Gly Ala Glu
   1               5                  10                  15

ttc gtg ggc acg ttc atc ctc atc ttc ttc gcg acg gcg gcg ccg atc       97
Phe Val Gly Thr Phe Ile Leu Ile Phe Phe Ala Thr Ala Ala Pro Ile
             20                  25                  30

gtg aac cag aag tac ggc ggc gcg atc agc ccg ttc ggg aac gcg gcg      145
Val Asn Gln Lys Tyr Gly Gly Ala Ile Ser Pro Phe Gly Asn Ala Ala
         35                  40                  45

tgc gcg ggg ctg gcg gtg gcg acc gtg atc ctg tcg acg ggg cac atc      193
Cys Ala Gly Leu Ala Val Ala Thr Val Ile Leu Ser Thr Gly His Ile
     50                  55                  60

tcc ggg gcg cac ctg aac ccg tcg ctc acc atc gcc ttc gcg gcg ctg      241
Ser Gly Ala His Leu Asn Pro Ser Leu Thr Ile Ala Phe Ala Ala Leu
 65                  70                  75                  80

cgc cac ttc ccc tgg ctg cag gtg ccc gcg tac gtg gcc gtc cag gcg      289
Arg His Phe Pro Trp Leu Gln Val Pro Ala Tyr Val Ala Val Gln Ala
                 85                  90                  95

ctg gca tcc gtc tgc gcc gcc ttc gcg ctc aag ggc gtc ttc cac ccg      337
Leu Ala Ser Val Cys Ala Ala Phe Ala Leu Lys Gly Val Phe His Pro
            100                 105                 110

ttc ctc tcc ggc ggc gtc acc gtg ccc gac gcc acc gtc tcc acc gcc      385
Phe Leu Ser Gly Gly Val Thr Val Pro Asp Ala Thr Val Ser Thr Ala
        115                 120                 125

cag gcg ttc ttc acc gag ttc atc atc tcc ttc aac ctc ctc ttc gtc      433
Gln Ala Phe Phe Thr Glu Phe Ile Ile Ser Phe Asn Leu Leu Phe Val
    130                 135                 140

gtc acc gcc gtc gcc acc gac acc cgc gca gtg ggt gaa ctc gcc ggg      481
Val Thr Ala Val Ala Thr Asp Thr Arg Ala Val Gly Glu Leu Ala Gly
145                 150                 155                 160

atc gcg gtg gga gcg gcc gta acg ctg aac atc ctc gtc gcc ggg ccg      529
Ile Ala Val Gly Ala Ala Val Thr Leu Asn Ile Leu Val Ala Gly Pro
                165                 170                 175

acg acg ggc ggg tcc atg aac ccg gtg agg acg ctg ggg ccg gcc gtg      577
Thr Thr Gly Gly Ser Met Asn Pro Val Arg Thr Leu Gly Pro Ala Val
            180                 185                 190

gcg gcg ggg aac tac cgg cag ctc tgg atc tac ctg ctg gcc ccg acg      625
Ala Ala Gly Asn Tyr Arg Gln Leu Trp Ile Tyr Leu Leu Ala Pro Thr
        195                 200                 205

ctg ggc gcg ttg gcg ggg gcc agc gtg tac aag gcg gtg aag ctc agg      673
Leu Gly Ala Leu Ala Gly Ala Ser Val Tyr Lys Ala Val Lys Leu Arg
    210                 215                 220

gac gag aac ggt gag acg ccg cgc acg cag cgc agc ttc cgc cgc t        719
Asp Glu Asn Gly Glu Thr Pro Arg Thr Gln Arg Ser Phe Arg Arg
225                 230                 235

gacgacgcac actggccacg ggcgcgagac attgtccggc cgtgtcacgc acgcccgcgt    779
```

```
cctcctccgc cgccgcgtaa cgcacggcca cgacgtgtcc gcggtcgtac gtgctgtgtc    839

tgtgtgtacc aataaataag ccccgttttg cttcgtccag aacggtccag tgctatgtgt    899

acgtggtctg tgttgtgatt tgcgaattgg attattgtgg gtcgtctcgt cgaggtctct    959

cgggtgtcgg gtgggtctga tgcgatccat cagcgtcgtg tccgaataaa agccacgccg   1019

atgcgccggc tgacgggcat ctggatgtgt gatttctgaa caagatttgc ttaatttcac   1079

ttgcttaaaa aaaaaaaaaa aaaaaaaagg gcggccg                            1116


<210> SEQ ID NO 42
<211> LENGTH: 239
<212> TYPE: PRT
<213> ORGANISM: Zea mays

<400> SEQUENCE: 42

Pro Gly Arg Pro Thr Arg Pro Gly Cys Cys Thr Gln Leu Gly Ala Glu
 1               5                  10                  15

Phe Val Gly Thr Phe Ile Leu Ile Phe Phe Ala Thr Ala Ala Pro Ile
            20                  25                  30

Val Asn Gln Lys Tyr Gly Gly Ala Ile Ser Pro Phe Gly Asn Ala Ala
        35                  40                  45

Cys Ala Gly Leu Ala Val Ala Thr Val Ile Leu Ser Thr Gly His Ile
    50                  55                  60

Ser Gly Ala His Leu Asn Pro Ser Leu Thr Ile Ala Phe Ala Ala Leu
65                  70                  75                  80

Arg His Phe Pro Trp Leu Gln Val Pro Ala Tyr Val Ala Val Gln Ala
                85                  90                  95

Leu Ala Ser Val Cys Ala Ala Phe Ala Leu Lys Gly Val Phe His Pro
            100                 105                 110

Phe Leu Ser Gly Gly Val Thr Val Pro Asp Ala Thr Val Ser Thr Ala
        115                 120                 125

Gln Ala Phe Phe Thr Glu Phe Ile Ile Ser Phe Asn Leu Leu Phe Val
    130                 135                 140

Val Thr Ala Val Ala Thr Asp Thr Arg Ala Val Gly Glu Leu Ala Gly
145                 150                 155                 160

Ile Ala Val Gly Ala Ala Val Thr Leu Asn Ile Leu Val Ala Gly Pro
                165                 170                 175

Thr Thr Gly Gly Ser Met Asn Pro Val Arg Thr Leu Gly Pro Ala Val
            180                 185                 190

Ala Ala Gly Asn Tyr Arg Gln Leu Trp Ile Tyr Leu Leu Ala Pro Thr
        195                 200                 205

Leu Gly Ala Leu Ala Gly Ala Ser Val Tyr Lys Ala Val Lys Leu Arg
    210                 215                 220

Asp Glu Asn Gly Glu Thr Pro Arg Thr Gln Arg Ser Phe Arg Arg
225                 230                 235


<210> SEQ ID NO 43
<211> LENGTH: 776
<212> TYPE: DNA
<213> ORGANISM: Zea mays
<220> FEATURE:
<221> NAME/KEY: CDS
<222> LOCATION: (20)...(341)

<400> SEQUENCE: 43

cccgggtcga cccacgcgt ccg cgg acg cgt ggg cgc gag ggg aaa ccg agt      52
                     Pro Arg Thr Arg Gly Arg Glu Gly Lys Pro Ser
```

-continued

```
                      1               5                   10

ggt ggt tgc agg gcg gtg tcg ggc gga tcg atg aac ccg gcg agg acg      100
Gly Gly Cys Arg Ala Val Ser Gly Gly Ser Met Asn Pro Ala Arg Thr
            15                  20                  25

ctg ggg ccg gcg ctg gcg agc aac ctc tac acc ggc ctc tgg atc tac      148
Leu Gly Pro Ala Leu Ala Ser Asn Leu Tyr Thr Gly Leu Trp Ile Tyr
        30                  35                  40

ttc ctg ggc ccc gtc ctc ggc acg ctc tcc ggc gcc tgg acc tac acc      196
Phe Leu Gly Pro Val Leu Gly Thr Leu Ser Gly Ala Trp Thr Tyr Thr
    45                  50                  55

ttc atc cgc ttc gag gag gcg ccc agc aag gac gcg tcg tcg tcg cac      244
Phe Ile Arg Phe Glu Glu Ala Pro Ser Lys Asp Ala Ser Ser Ser His
 60                  65                  70                  75

tcg cag aag ctc tcc tcc ttc aag ctc cgc cgc ctg cag agc cag tcc      292
Ser Gln Lys Leu Ser Ser Phe Lys Leu Arg Arg Leu Gln Ser Gln Ser
                80                  85                  90

gtc gcc gcc gac gcc gac gac gac gag gag ctc gac cac atc cag gtg      340
Val Ala Ala Asp Ala Asp Asp Asp Glu Glu Leu Asp His Ile Gln Val
            95                 100                 105

t gaagtgtgat gtgatgtccg gccgctccgt acgtcccgtc gatcagagag             391

tgcacacgta cgtgctactc ctaacactat gtgcctagca ggatagttag ttatggtcga    451

tggtgatgtc tgctggtctg tgcgctggtc ggttctcatg atccgatcca tgcgcgcacg    511

cacgcactcg cattgtgtgt ccggttggtg gcgcgctgtg gatacatgca tgggctcgct    571

ctgtcaatgt gccaacgagc tggcgcttct ttttgggacg aattaacact gtgccgtgtg    631

cgtacgcgtg tgcagttagc tagtcgtacg cgcgtgccaa gcgtgcgtac gtctcctgct    691

gtcactcttg ttccaaaatc agttgatggt gcttatatat acaaagatca tcaggaaggc    751

aaaaaaaaaa aaaaaagggc ggccg                                           776


<210> SEQ ID NO 44
<211> LENGTH: 107
<212> TYPE: PRT
<213> ORGANISM: Zea mays

<400> SEQUENCE: 44

Pro Arg Thr Arg Gly Arg Glu Gly Lys Pro Ser Gly Gly Cys Arg Ala
 1               5                  10                  15

Val Ser Gly Gly Ser Met Asn Pro Ala Arg Thr Leu Gly Pro Ala Leu
            20                  25                  30

Ala Ser Asn Leu Tyr Thr Gly Leu Trp Ile Tyr Phe Leu Gly Pro Val
        35                  40                  45

Leu Gly Thr Leu Ser Gly Ala Trp Thr Tyr Thr Phe Ile Arg Phe Glu
    50                  55                  60

Glu Ala Pro Ser Lys Asp Ala Ser Ser Ser His Ser Gln Lys Leu Ser
65                  70                  75                  80

Ser Phe Lys Leu Arg Arg Leu Gln Ser Gln Ser Val Ala Ala Asp Ala
                85                  90                  95

Asp Asp Asp Glu Glu Leu Asp His Ile Gln Val
            100                 105


<210> SEQ ID NO 45
<211> LENGTH: 686
<212> TYPE: DNA
<213> ORGANISM: Zea mays
<220> FEATURE:
<221> NAME/KEY: CDS
<222> LOCATION: (109)...(559)
```

-continued

```
<400> SEQUENCE: 45

cccgggctgc aggaattggc acgaggctca ttgctcacca agctgccgtt ctacgtggcg      60

gcgcagctgg caggctcgtt gctcgcctgc ctgtcagcga acggcgtc atg gag ccg      117
                                                     Met Glu Pro
                                                      1

cgg gcg gag cac ttc tac ggg acc gtc ccc atg gcc ggc ggc gac acg       165
Arg Ala Glu His Phe Tyr Gly Thr Val Pro Met Ala Gly Gly Asp Thr
     5                  10                  15

agg ctg ccg ttc ctg ctg gag ctg gtc gcc tcc gcg ctg ctc atg gtc       213
Arg Leu Pro Phe Leu Leu Glu Leu Val Ala Ser Ala Leu Leu Met Val
 20                  25                  30                  35

gtc atc gcc acc gct gcc aga ggc tcc aat cag aca gca gga ggg ctg       261
Val Ile Ala Thr Ala Ala Arg Gly Ser Asn Gln Thr Ala Gly Gly Leu
                 40                  45                  50

gcc atc ggc gcc gcc gtc ggc gcc ctg ggc ctc gtc atc ggg ccg gtg       309
Ala Ile Gly Ala Ala Val Gly Ala Leu Gly Leu Val Ile Gly Pro Val
             55                  60                  65

tcc gga ggc tcg atg aac ccg atc agg acc ctg ggc ccg gcc atc gtg       357
Ser Gly Gly Ser Met Asn Pro Ile Arg Thr Leu Gly Pro Ala Ile Val
         70                  75                  80

ctc ggc agg tac acc tcc gtc tgg atc tat ctc gtc gcg ccc gtc gcc       405
Leu Gly Arg Tyr Thr Ser Val Trp Ile Tyr Leu Val Ala Pro Val Ala
     85                  90                  95

ggg atg ctc atc ggc gcc ctc tgc aac cgc ctc gtc agg cgc tcc gac       453
Gly Met Leu Ile Gly Ala Leu Cys Asn Arg Leu Val Arg Arg Ser Asp
100                 105                 110                 115

gcc atc atc gcc ttc ctc tgc ggc gcc aag ccc aga gtg gtg gcg cca       501
Ala Ile Ile Ala Phe Leu Cys Gly Ala Lys Pro Arg Val Val Ala Pro
                120                 125                 130

ggc cag aac cgc gcc gcg cgc cgt tgg agc act tgc gtc tcc gcg cta       549
Gly Gln Asn Arg Ala Ala Arg Arg Trp Ser Thr Cys Val Ser Ala Leu
            135                 140                 145

cta gca ggc t agccgtcggg cgccgccatc gtggcctgct tgttgtaaca             599
Leu Ala Gly
        150

gttatgagtc aaaccactct tttgtgatac acgctaacac gcctacaccc aacgtttcga     659

attaaaaaaa aaaaaaaaaa aactcga                                         686


<210> SEQ ID NO 46
<211> LENGTH: 150
<212> TYPE: PRT
<213> ORGANISM: Zea mays

<400> SEQUENCE: 46

Met Glu Pro Arg Ala Glu His Phe Tyr Gly Thr Val Pro Met Ala Gly
 1               5                  10                  15

Gly Asp Thr Arg Leu Pro Phe Leu Leu Glu Leu Val Ala Ser Ala Leu
            20                  25                  30

Leu Met Val Val Ile Ala Thr Ala Ala Arg Gly Ser Asn Gln Thr Ala
        35                  40                  45

Gly Gly Leu Ala Ile Gly Ala Ala Val Gly Ala Leu Gly Leu Val Ile
    50                  55                  60

Gly Pro Val Ser Gly Gly Ser Met Asn Pro Ile Arg Thr Leu Gly Pro
65                  70                  75                  80

Ala Ile Val Leu Gly Arg Tyr Thr Ser Val Trp Ile Tyr Leu Val Ala
                85                  90                  95
```

-continued

```
Pro Val Ala Gly Met Leu Ile Gly Ala Leu Cys Asn Arg Leu Val Arg
            100                 105                 110

Arg Ser Asp Ala Ile Ile Ala Phe Leu Cys Gly Ala Lys Pro Arg Val
        115                 120                 125

Val Ala Pro Gly Gln Asn Arg Ala Ala Arg Arg Trp Ser Thr Cys Val
    130                 135                 140

Ser Ala Leu Leu Ala Gly
145                 150


<210> SEQ ID NO 47
<211> LENGTH: 1100
<212> TYPE: DNA
<213> ORGANISM: Zea mays
<220> FEATURE:
<221> NAME/KEY: CDS
<222> LOCATION: (94)...(835)

<400> SEQUENCE: 47

cccgggtcga cccacgcgtc cgatcttctt ctctgaattc cagtccaagg gccggaatac     60

cgtcagaggg agtgggagag ggggggaaaa aag atg gtg aag ctc gca ttt gga     114
                                     Met Val Lys Leu Ala Phe Gly
                                     1               5

agc ttt cgc gac tct ttg agc gcc gcg tcg ctc aag gcc tat gtg gcc      162
Ser Phe Arg Asp Ser Leu Ser Ala Ala Ser Leu Lys Ala Tyr Val Ala
        10                  15                  20

gag ttc att gcc acg ctg ctc ttc gtg ttc gcc ggc gtc ggg tcc gcc      210
Glu Phe Ile Ala Thr Leu Leu Phe Val Phe Ala Gly Val Gly Ser Ala
    25                  30                  35

att gcc tac tcg caa ttg acg aag ggc ggc gct ctg gac ccc gcc ggc      258
Ile Ala Tyr Ser Gln Leu Thr Lys Gly Gly Ala Leu Asp Pro Ala Gly
 40                  45                  50                  55

ctg gtg gcc atc gcc atc gcc cat gcg ttc gcg ctc ttc gtc ggc gtc      306
Leu Val Ala Ile Ala Ile Ala His Ala Phe Ala Leu Phe Val Gly Val
                60                  65                  70

tcc atg gcc gcc aac atc tcc ggc ggc cac ctg aac ccc gcc gtc acc      354
Ser Met Ala Ala Asn Ile Ser Gly Gly His Leu Asn Pro Ala Val Thr
            75                  80                  85

ttc ggc ctc gcc gtc ggc ggc aca tca cat cct cac cgg cat cct cta      402
Phe Gly Leu Ala Val Gly Gly Thr Ser His Pro His Arg His Pro Leu
        90                  95                  100

ctg ggt tgc cca gct tct cgg cgc ttc cgt ggc gtg ctt tct cct gca      450
Leu Gly Cys Pro Ala Ser Arg Arg Phe Arg Gly Val Leu Ser Pro Ala
    105                 110                 115

gta cgt cac cca cgg aca ggc tat ccc gac gca cgg cgt ctc cgg atc      498
Val Arg His Pro Arg Thr Gly Tyr Pro Asp Ala Arg Arg Leu Arg Ile
120                 125                 130                 135

agc gag atc gag ggc gtg gtg atg gag atc gtg atc acc ttc gcg ctg      546
Ser Glu Ile Glu Gly Val Val Met Glu Ile Val Ile Thr Phe Ala Leu
                140                 145                 150

gtg tac acc gtg tac gcc acc gcg gcc gac ccg aag aag ggg tcc ctg      594
Val Tyr Thr Val Tyr Ala Thr Ala Ala Asp Pro Lys Lys Gly Ser Leu
            155                 160                 165

ggc acc atc gcg ccc atg gcc atc ggc ttc atc gtc ggc gcc aac atc      642
Gly Thr Ile Ala Pro Met Ala Ile Gly Phe Ile Val Gly Ala Asn Ile
        170                 175                 180

ctg gcc gcc ggc ccc ttc agc ggc ggc tcc atg aac ccg gcc cgc tcc      690
Leu Ala Ala Gly Pro Phe Ser Gly Gly Ser Met Asn Pro Ala Arg Ser
    185                 190                 195

ttc ggc ccc gcc gtg gcg gcc ggt aac ttc gcc ggc aac tgg gtg tac      738
Phe Gly Pro Ala Val Ala Ala Gly Asn Phe Ala Gly Asn Trp Val Tyr
```

-continued

```
200                 205                 210                 215

tgg gtc ggc ccc ctc gtc ggc ggt ggc ctg gcg ggg ctc gtc tac ggc      786
Trp Val Gly Pro Leu Val Gly Gly Gly Leu Ala Gly Leu Val Tyr Gly
                220                 225                 230

gac gtg ttc atc gcc tcc tac cag ccg gtc ggc cag cag gag tac cca      834
Asp Val Phe Ile Ala Ser Tyr Gln Pro Val Gly Gln Gln Glu Tyr Pro
            235                 240                 245

t gaaagtccgg atgagctagc ccgatcgatc cgtctgtgtt gatttcacca             885

tcgtcgtcgt cgtgtcatct ggcgcttcgt gctgtgatca tgttttgtcc tgtttgcatt    945

tcccaacgtc tggttttcat ttccattcac caacggtgcc aagatgccgt aagcaagcga   1005

gagaagtgtt cggtctgtat ctgtataaat gcaatgcaca gttcggcgtt tccatgaaaa   1065

aaaaaaaaaa aaaaaaaaaa aaaaaggggc ggccg                              1100


<210> SEQ ID NO 48
<211> LENGTH: 247
<212> TYPE: PRT
<213> ORGANISM: Zea mays

<400> SEQUENCE: 48

Met Val Lys Leu Ala Phe Gly Ser Phe Arg Asp Ser Leu Ser Ala Ala
 1               5                  10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Leu Ala Val Gly Gly Thr Ser
                85                  90                  95

His Pro His Arg His Pro Leu Leu Gly Cys Pro Ala Ser Arg Arg Phe
            100                 105                 110

Arg Gly Val Leu Ser Pro Ala Val Arg His Pro Arg Thr Gly Tyr Pro
        115                 120                 125

Asp Ala Arg Arg Leu Arg Ile Ser Glu Ile Glu Gly Val Val Met Glu
    130                 135                 140

Ile Val Ile Thr Phe Ala Leu Val Tyr Thr Val Tyr Ala Thr Ala Ala
145                 150                 155                 160

Asp Pro Lys Lys Gly Ser Leu Gly Thr Ile Ala Pro Met Ala Ile Gly
                165                 170                 175

Phe Ile Val Gly Ala Asn Ile Leu Ala Ala Gly Pro Phe Ser Gly Gly
            180                 185                 190

Ser Met Asn Pro Ala Arg Ser Phe Gly Pro Ala Val Ala Ala Gly Asn
        195                 200                 205

Phe Ala Gly Asn Trp Val Tyr Trp Val Gly Pro Leu Val Gly Gly Gly
    210                 215                 220

Leu Ala Gly Leu Val Tyr Gly Asp Val Phe Ile Ala Ser Tyr Gln Pro
225                 230                 235                 240

Val Gly Gln Gln Glu Tyr Pro
                245


<210> SEQ ID NO 49
<211> LENGTH: 36
```

-continued

```
<212> TYPE: DNA
<213> ORGANISM: Artificial Sequence
<220> FEATURE:
<223> OTHER INFORMATION: Sal A20 oligo

<400> SEQUENCE: 49

tcgacccacg cgtccgaaaa aaaaaaaaaa aaaaaa                                36
```